United States Patent
McDonald et al.

(10) Patent No.: US 9,676,775 B2
(45) Date of Patent: *Jun. 13, 2017

(54) HETEROARYLENE-BRIDGED BENZODIAZEPINE DIMERS, CONJUGATES THEREOF, AND METHODS OF MAKING AND USING

(71) Applicant: BRISTOL-MYERS SQUIBB COMPANY, Princeton, NJ (US)

(72) Inventors: Ivar M. McDonald, East Haddam, CT (US); Naidu S. Chowdari, Sunnyvale, CA (US); Walter Lewis Johnson, San Francisco, CA (US); Yong Zhang, West Windsor, NJ (US); Robert M. Borzilleri, Carversville, PA (US); Sanjeev Gangwar, Foster City, CA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/351,955

(22) Filed: Nov. 15, 2016

(65) Prior Publication Data
US 2017/0057959 A1    Mar. 2, 2017

Related U.S. Application Data

(63) Continuation of application No. 14/994,378, filed on Jan. 13, 2016.

(60) Provisional application No. 62/103,157, filed on Jan. 14, 2015, provisional application No. 62/215,938, filed on Sep. 9, 2015.

(51) Int. Cl.
C07D 487/04  (2006.01)
C07D 519/00  (2006.01)
C07D 471/04  (2006.01)

(52) U.S. Cl.
CPC ................... *C07D 471/04* (2013.01)

(58) Field of Classification Search
CPC ................ C07D 487/04; C07D 519/00
See application file for complete search history.

(56) References Cited

U.S. PATENT DOCUMENTS

| | | |
|---|---|---|
| 7,049,311 B1 | 5/2006 | Thurston et al. |
| 7,244,724 B2 | 7/2007 | Liu et al. |
| 7,407,951 B2 | 8/2008 | Thurston et al. |
| 7,528,126 B2 | 5/2009 | Howard et al. |
| 7,557,099 B2 | 7/2009 | Howard et al. |
| 7,612,062 B2 | 11/2009 | Gregson et al. |

(Continued)

FOREIGN PATENT DOCUMENTS

| | | |
|---|---|---|
| WO | WO 2013/041606 A1 | 3/2013 |
| WO | WO 2013/177481 A1 | 11/2013 |

(Continued)

OTHER PUBLICATIONS

Scott Jeffrey et al., *Bio Conjugate Chemistry*, "A Potent Anti-CD70 Antibody—Drug Conjugate Combining a Dimeric Pyrrolobenzodiazepine Drug with Site-Specific Conjugation", vol. 24: pp. 1256-1263, 2013.

(Continued)

*Primary Examiner* — Bruck Kifle
(74) *Attorney, Agent, or Firm* — Yuan Chao

(57) ABSTRACT

Benzodiazepine dimers having a structure represented by

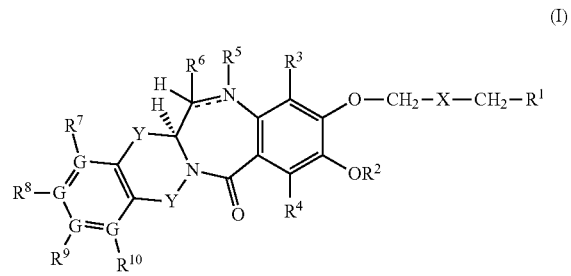

wherein X comprises a heteroaromatic moiety and is as further defined in the application; $R^1$ is

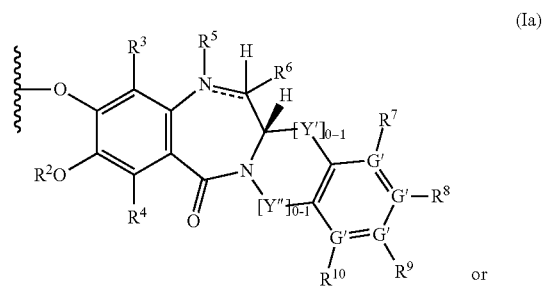

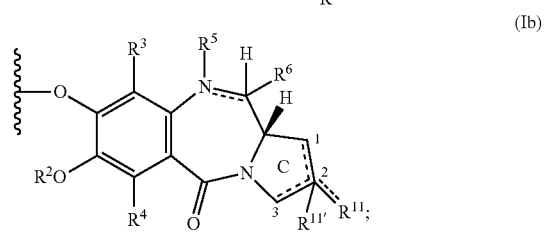

and the other variables in formulae (I), (Ia), and (Ib) are as defined in the application. Such dimers are useful as anticancer agents, especially when used in an antibody-drug conjugate (ADC).

1 Claim, 24 Drawing Sheets

(56) References Cited

U.S. PATENT DOCUMENTS

Figure 1:
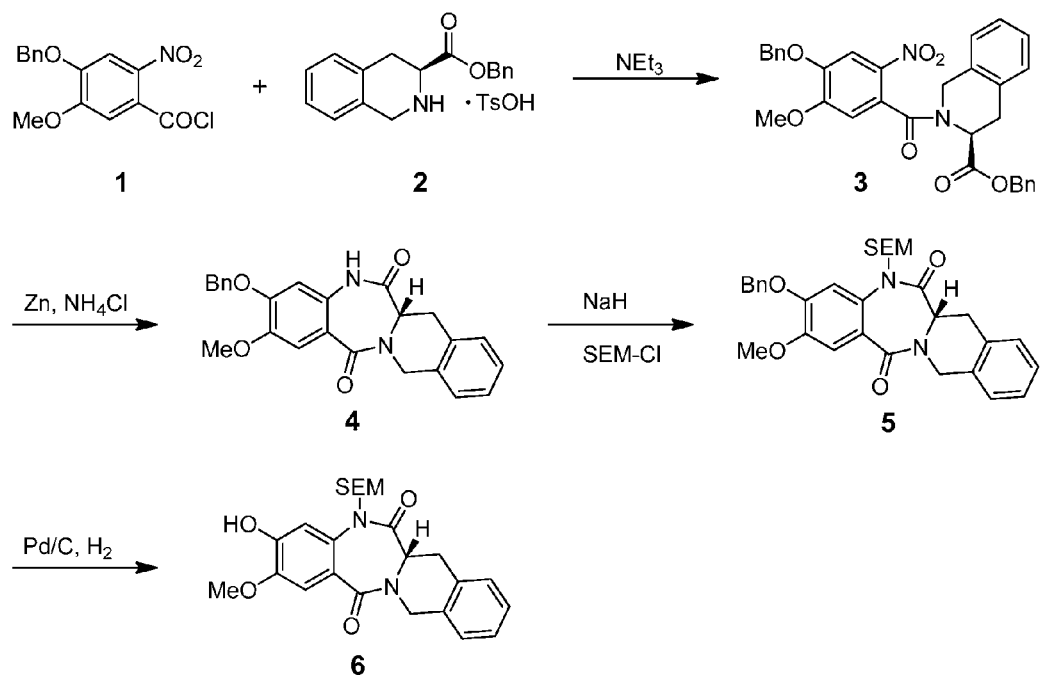

| | | |
|---|---|---|
| 7,659,241 B2 | 2/2010 | Senter et al. |
| 7,741,319 B2 | 6/2010 | Howard et al. |
| 8,124,738 B2 | 2/2012 | Terret et al. |
| 8,163,736 B2 | 4/2012 | Gauzy et al. |
| 8,268,970 B2 | 9/2012 | Terrett et al. |
| 8,383,118 B2 | 2/2013 | Vistica et al. |
| 8,404,678 B2 | 3/2013 | Bouchard et al. |
| 8,426,402 B2 | 4/2013 | Li et al. |
| 8,481,042 B2 | 7/2013 | Commercon et al. |
| 8,501,934 B2 | 8/2013 | Howard et al. |
| 8,592,576 B2 | 11/2013 | Howard et al. |
| 8,680,247 B2 | 3/2014 | Terrett et al. |
| 8,697,688 B2 | 4/2014 | Howard et al. |
| 8,765,740 B2 | 7/2014 | Li et al. |
| 2007/0191349 A1 | 8/2007 | Howard et al. |
| 2011/0256157 A1 | 10/2011 | Howard et al. |
| 2013/0028919 A1 | 1/2013 | Howard et al. |
| 2013/0137659 A1 | 5/2013 | Commercon et al. |
| 2013/0266595 A1 | 10/2013 | Elygare et al. |
| 2014/0120118 A1 | 5/2014 | Howard |
| 2014/0127239 A1 | 5/2014 | Howard |
| 2014/0234346 A1 | 8/2014 | Howard |
| 2014/0274907 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |

FOREIGN PATENT DOCUMENTS

| | | | |
|---|---|---|---|
| WO | WO 2014/031566 A1 | 2/2014 | |
| WO | WO 2014/080251 A1 | 3/2014 | |
| WO | WO 2014/096365 A1 | 6/2014 | |
| WO | WO 2014/096368 A1 | 6/2014 | |
| WO | WO 2014/140174 A1 | 9/2014 | |
| WO | WO 2014/140862 A2 | 9/2014 | |
| WO | WO 2014/174111 A1 | 10/2014 | |

OTHER PUBLICATIONS

Stephen J. Gregson, et al., *Bioorganic & Medicinal Chemistry Letters* "Synthesis of the First Example of a C2-C3/C20-C30-endo Unsaturated Pyrrolo[2,1-c][1,4]benzodiazepine Dimer",\ 11: pp. 2859-2862, 2011.

Kiran Kumar Kothakonda, et al., *Bioorganic & Medicinal Chemistry Letters*, "Synthesis of a novel tetrahydroisoquinolino[2,1-c][1,4]benzodiazepine ring system with DNA recognition potential", 14: pp. 4371-4373, 2014.

Stephen J. Gregson et al., *ChemComm*, "Synthesis of a novel C2/C2A-exo unsaturated pyrrolobenzodiazepine cross-linking agent with remarkable DNA binding affinity and cytotoxicity", pp. 797-798, 1999.

John A Hartley, *Expert Opinion Investig. Drugs*, "The development of pyrrolobenzodiazepines as antitumour agents", vol. 20: pp. 733-744. 2011.

John A. Hartley, et al., *Invest New Drugs*, "DNA interstrand cross-linking and in vivo antitumor activity of the extended pyrrolo[2,1-c][1,4]benzodiazepine dimer SG2057", vol. 30: pp. 950-958, 2012.

D. Subhas Bose, et al. *J. Am. Chem.* SOC, "Rational Design of a Highly Efficient Irreversible DNA Interstrand Cross-Linking Agent Based on the Pyrrolobenzodiazepine Wing System", vol. 114: pp. 4939-4941, 1992.

David E. Thurston, et al., *J. Med. Chem*, "Effect of A-Ring Modifications on the DNA-Binding Behavior and Cytotoxicity of Pyrrolo[2,1-c][1,4]benzodiazepines", vol. 42: pp. 1951-1964, 1999.

Stephen J. Gregson et al., *J. Med. Chem*, "Design, Synthesis, and Evaluation of a Novel Pyrrolobenzodiazepine DNA-Interactive Agent with Highly Efficient Cross-Linking Ability and Potent Cytotoxicity", vol. 44: pp. 737-748, 2001.

Stephen J. Gregson et al., *J. Med. Chem*, "Linker Length Modulates DNA Cross-Linking Reactivity and Cytotoxic Potency of C8/C8¢ Ether-Linked C2-exo-Unsaturated Pyrrolo[2,1-c][1,4]benzodiazepine (PBD) Dimers", vol. 47: pp. 1161-1174, 2004.

Dyeison Antonow, et al., *J. Med. Chem*, "Structure-Activity Relationships of Monomeric C2-Aryl Pyrrolo[2,1-c][1,4]benzodiazepine (PBD) Antitumor Agents", vol. 53: pp. 2927-2941, 2010.

David E. Thurston, et al., *J. Org. Chem.*, "Synthesis of Sequence-Selective C8-Linked Pyrrolo[2,1-c][1,4]benzodiazepine DNA Interstrand Cross-Linking", vol. 61: pp. 8141-8147, 1996.

David Schrama et al., *Nature Reviews Drug Discovery*, "Antibody targeted drugs as cancer Therapeutics", vol. 5: pp. 147-159, 2006.

International Search Report and Written Opinion, for PCT Application No. PCT/US2016/013154, mailed Mar. 16, 2016.

HETEROARYLENE-BRIDGED BENZODIAZEPINE DIMERS, CONJUGATES THEREOF, AND METHODS OF MAKING AND USING

CROSS-REFERENCE TO RELATED APPLICATIONS

This application is a continuation of U.S. application Ser. No. 14/994,378, filed Jan. 13, 2016; which claims the benefit under 35 U.S.C. §119(e) of U.S. Provisional Application Ser. No. 62/103,157, filed Jan. 14, 2015, and U.S. Provisional Application Ser. No. 62/215,938, filed Sep. 9, 2015; the disclosures of which are incorporated herein by reference.

BACKGROUND OF THE INVENTION

This invention relates to benzodiazepine dimers having a heteroaromatic group between the two dimer units, dimer-linker compounds derived therefrom, conjugates thereof, and methods for their preparation and use.

Some naturally occurring cytotoxins, such as tomaymycin and anthramycin, contain a benzodiazepine ring system. Reflecting the additional presence of a pyrrolidine ring fused to the diazepine ring, these compounds are often referred to as pyrrolobenzodiazepines, or PBDs.

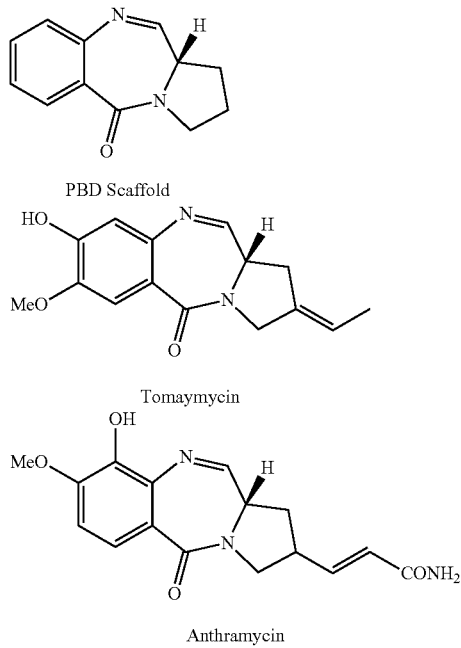

PBDs possess antibiotic and antitumor activity, the latter trait leading to interest in them as anticancer drugs. Mechanistically, PBDs bind to the minor groove of DNA in a sequence selective manner and alkylate the DNA. The structure-activity relationship (SAR) of different substituents has been studied (Antonow et al. 2010; Thurston et al. 1999).

Additional studies have shown that PBD dimers show special promise as anticancer agents. The core structure of a typical PBD dimer can be represented by formula (A-1), where X is a bridging group connecting the two dimer halves.

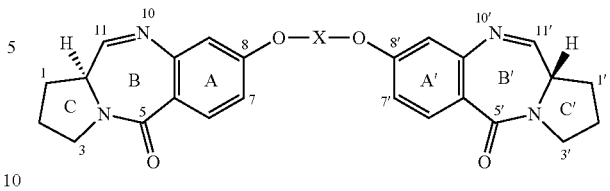

As with monomeric PBDs, the dimers are DNA minor groove binder-alkylators. Being bifunctional, alkylation by a dimer results in cross-linked DNA, making DNA repair more difficult. (DNA alkylation occurs via the imine group. PDBs having one of the imine groups reduced can still alkylate DNA, but cannot crosslink it. They are still biologically active, albeit generally less so, but their different pharmacokinetic profile may be preferable for some applications.) For a review on the evolution of PBDs as antitumor agents, from naturally occurring monomers to synthetic monomers to synthetic dimers, see Hartley 2011.

The SAR of PBD dimers has been explored via substituents on the A/A' and C/C' rings, unsaturation in the C/C' rings, the structure and length of the bridging group X, and the oxidation or reduction of the imine double bonds in rings B/B', and combinations of such features. See Bose et al. 1992, Gregson et al. 1999, Gregson et al. 2001a and 2001b, Gregson et al. 2004, Gregson et al. 2009, Hartley et al. 2012, Howard et al. 2007, Howard et al. 2009a, Howard et al. 2010, Howard et al. 2013a and 2013b, Liu et al. 2007, Thurston et al. 1996, Thurston et al. 2006, and Thurston et al. 2008. Most PBD dimers are joined via an 8/8' bridge as shown above, but a 7/7' bridge also has been disclosed (Howard et al. 2009b).

A type of anticancer agent that is generating strong interest is an antibody-drug conjugate (ADC, also referred to as an immunoconjugate). In an ADC, a therapeutic agent (also referred to as the drug, payload, or warhead) is covalently linked to an antibody whose antigen is expressed by a cancer cell (tumor associated antigen). The antibody, by binding to the antigen, delivers the ADC to the cancer site. There, cleavage of the covalent link or degradation of the antibody leads to the release of the therapeutic agent. Conversely, while the ADC is circulating in the blood system, the therapeutic agent is held inactive because of its covalent linkage to the antibody. Thus, the therapeutic agent used in an ADC can be much more potent (i.e., cytotoxic) than ordinary chemotherapy agents because of its localized release. For a review on ADCs, see Schrama et al. 2006.

PBD dimers have been proposed as the drug in an ADC. Attachment of the linker connecting to the antibody can be via a functional group located in a C/C' ring, the bridging group X, or by addition across the imine group in a B/B' ring. See Beau-Larvor et al. 2014, Bouchard et al. 2013, Commercon et al. 2013a and 2013b, Flygare et al. 2013, Gauzy et al. 2012, Howard 2104a-2014e, Howard et al. 2011, Howard et al. 2013c and 2013d, Howard et al. 2014a-2014h, Jeffrey et al. 2013, Jeffrey et al. 2014a and 2014b, and Zhao et al. 2014.

Another type of benzodiazepine dimer also has been proposed as a drug for use in ADCs. Structurally, this type may be viewed as a PBD dimer further having a phenyl ring fused to each of C/C' rings, as shown in formulae (A-2) and (A-3). See Chari et al. 2013, Li et al. 2013, Fishkin et al. 2014, Li et al. 2014.

(A-2)

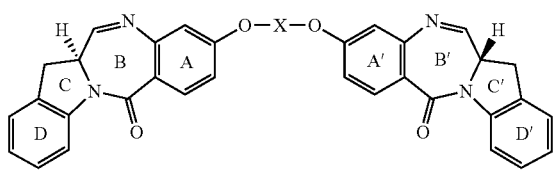

(A-3)

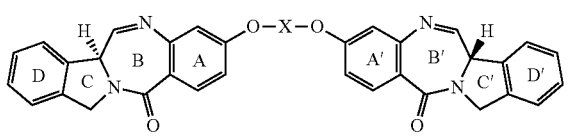

Benzodiazepine compounds having other ring systems, such as a tetrahydroisoquinolino[2,1-c][1,4]benzodiazepine, also have been disclosed. Kothakonda et al. 2004.

Full citations for the documents cited herein by first author or inventor and year are listed at the end of this specification.

BRIEF SUMMARY OF THE INVENTION

This invention provides novel benzodiazepine dimers, in which at least one of the benzodiazepine units has a tetrahydroisoquinoline (THIQ) ring system fused to a benzodiazepine ring system and further having a heteroarylene moiety in the bridge linking the two dimer units. Optionally, the imine bond in the benzodiazepine ring system can be reduced.

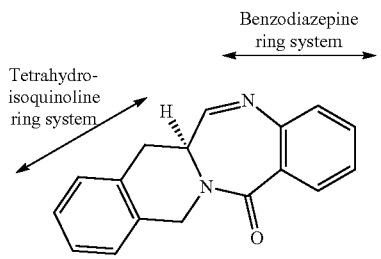 [SMILES: O=C1c2ccccc2N=C[C@@H]2Cc3ccccc3CN12]

Both units (halves) of the dimer can have a THIQ ring system ("THIQ-THIQ dimer" or "THIQ homodimer"), or one unit can have a THIQ ring system while the other unit has a different benzodiazepine ring system, such as a PBD ring system (generally, a "THIQ heterodimer" or, in this particular example, a "THIQ-PBD dimer"). In a THIQ-THIQ dimer the two units can be identical ("symmetric THIQ-THIQ dimer") or different ("asymmetric THIQ-THIQ dimer").

Thus, this invention provides a benzodiazepine dimer having a structure represented by formula (I):

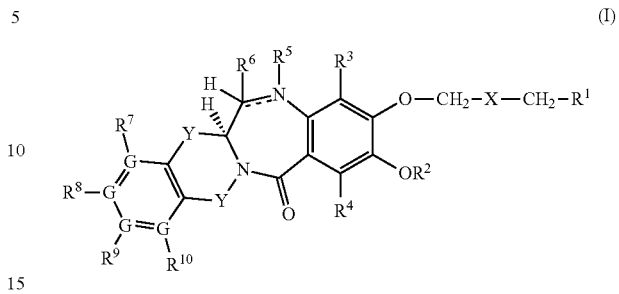

(I)

wherein
X is selected from the group consisting of

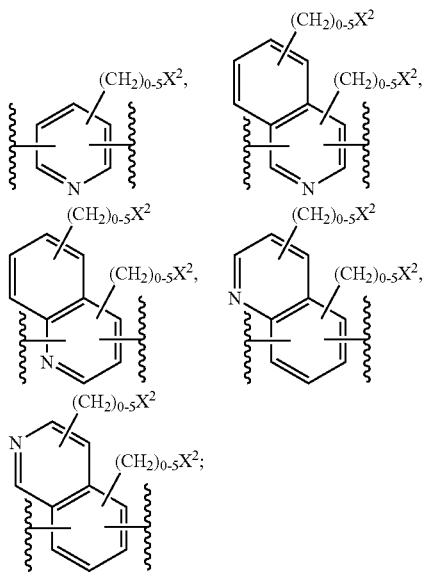

$R^1$ is according to formula (Ia) or formula (Ib):

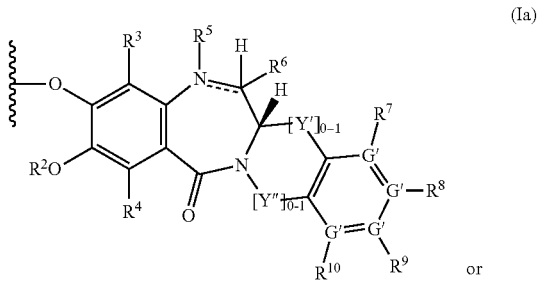

(Ia)

or

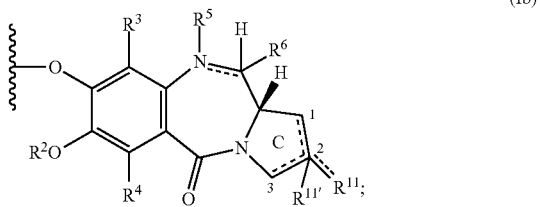

(Ib)

each G and G' is C or N, with the proviso that no more than two Gs or two G's are N;

each $R^2$ is independently H or $C_1$-$C_5$ alkyl;

each $R^3$ and $R^4$ is independently H, F, Cl, Br, OH, $C_1$-$C_3$ alkyl, O($C_1$-$C_3$ alkyl), cyano, $(CH_2)_{0-5}NH_2$, or $NO_2$;

each double line ==== in a diazepine ring system independently represents a single bond or a double bond;

each $R^5$ is H if the double line ==== to the N to which it is attached is a single bond and is absent if the double line is a double bond;

each $R^6$ is H, OH, $SO_3Na$, or $SO_3K$ if the double line ==== to the C to which it is attached is a single bond and is absent if the double line is a double bond;

each $R^7$, $R^8$, $R^9$, and $R^{10}$ is independently H, $C_1$-$C_5$ alkyl, $C\equiv C(CH_2)_{1-5}X^2$, OH, O($C_1$-$C_5$ alkyl), cyano, $NO_2$, F, Cl, Br, $O(CH_2CH_2O)_{1-8}(C_{1-3}$ alkyl), $(CH_2)_{0-5}X^2$, $O(CH_2)_{2-5}X^2$, 3- to 7-membered cycloalkyl or heterocycloalkyl unsubstituted or substituted with $(CH_2)_{0-5}X^2$ or $O(CH_2)_{2-5}X^2$, 5- to 6-membered aryl or heteroaryl unsubstituted or substituted with $(CH_2)_{0-5}X^2$ or $O(CH_2)_{2-5}X^2$,

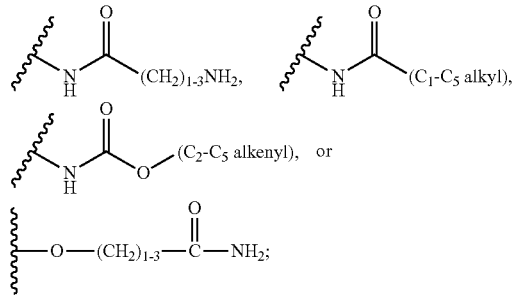

or where a $R^7$, $R^8$, $R^9$, or $R^{10}$ is attached to a G or G' that is N, such $R^7$, $R^8$, $R^9$, or $R^{10}$ is absent;

the dotted lines in ring C of formula (Ib) indicate the optional presence of a C1-C2, C2-C3, or C2-$R^{11}$ double bond;

$R^{11}$ is H, =O, =$CH_2$, =CH($C_1$-$C_5$ alkyl), CH=CH $(CH_2)_{1-5}X^2$, $C\equiv C(CH_2)_{1-5}X^2$, $C_1$-$C_5$ alkyl, OH, O($C_1$-$C_5$ alkyl), cyano, $NO_2$, F, Cl, Br, $O(CH_2CH_2O)_{1-8}(C_{1-3}$ alkyl), $(CH_2)_{0-5}X^2$, 4- to 7-membered aryl, heteroaryl, cycloalkyl, or heterocycloalkyl unsubstituted or substituted with $(CH_2)_{0-5}X^2$, $O(CH_2)_{2-5}X^2$, 3- to 7-membered cycloalkyl or heterocycloalkyl unsubstituted or substituted with $(CH_2)_{0-5}X^2$ or $O(CH_2)_{2-5}X^2$, 5- to 6-membered aryl or heteroaryl unsubstituted or substituted with $(CH_2)_{0-5}X^2$ or $O(CH_2)_{2-5}X^2$;

$R^{11'}$ is absent if a C1-C2, C2-C3, or C2-$R^{11}$ double bond is present and otherwise is H;

each $X^2$ is independently H, F, Cl, Br, OH, O($C_1$-$C_3$ alkyl), O($C_1$-$C_3$ alkylene), $CO_2H$, $N_3$, CN, $NO_2$, $CO_2(C_1$-$C_3$ alkyl), $NH_2$, NH($C_1$-$C_5$ alkyl), N($C_1$-$C_5$ alkyl)$_2$, SH, CHO, $N(CH_2CH_2)_2N(C_1$-$C_3$ alkyl), $NHNH_2$, or C(=O) $NHNH_2$;

each Y is independently $CH_2$, C=O, or $CHR^{12}$; wherein each $R^{12}$ is independently F, Cl, Br, or $C_1$-$C_3$ alkyl; and Y' and Y" are independently $CH_2$, C=O, or $CHR^{12}$; wherein each $R^{12}$ is independently F, Cl, Br, or $C_1$-$C_3$ alkyl, with the proviso that at least one of Y' and Y" is present;

or a pharmaceutically acceptable salt thereof.

In another embodiment, this invention provides a conjugate comprising a dimer of formula (I) covalently bonded to a targeting moiety that specifically or preferentially binds to a chemical entity on a target cell, which target cell preferably is a cancer cell. Preferably, the targeting moiety is an antibody—more preferably a monoclonal antibody; even more preferably a human monoclonal antibody—and the chemical entity is a tumor associated antigen. The tumor associated antigen can be one that is displayed on the surface of a cancer cell or one that is secreted by a cancer cell into the surrounding extracellular space. Preferably, the tumor associated antigen is one that is over-expressed by the cancer cell compared to normal cells or one that is expressed by cancer cells but not normal cells.

In another embodiment, there is provided a dimer according to formula (I) covalently bonded to a linker moiety having a reactive functional group, suitable for conjugation to a targeting moiety.

In another embodiment, there is provided a method for treating a cancer in a subject suffering from such cancer, comprising administering to the subject a therapeutically effective amount of a dimer of this invention or a conjugate thereof with a targeting moiety. In another embodiment, there is provided the use of a dimer of this invention or a conjugate thereof with a targeting moiety for the preparation of a medicament for the treatment of cancer in a subject suffering from such cancer. A dimer of this invention or a conjugate thereof with a targeting moiety can also be used to inhibit the proliferation, in vitro, ex vivo, or in vivo, of cancer cells. Especially, the cancer can be lung or gastric cancer.

BRIEF DESCRIPTION OF THE DRAWING(S)

FIGS. 1, 2, 3, 4, 5, 19A, 19B, and 21 show schemes for the syntheses of various intermediates useful in the preparation of dimers of this invention.

FIGS. 6, 8, 9, 11, 14, 16, 18, and 22 show schemes for the synthesis of various dimers of this invention.

FIGS. 7A, 7B, 10, 12A, 12B, 13, 15, 17, and 20 show schemes for the synthesis of various dimer-linkers of this invention.

DETAILED DESCRIPTION OF THE INVENTION

Definitions

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5\times10^{-8}$ M or less, more preferably $1\times10^{-8}$ M or less, more preferably $6\times10^{-9}$ M or less, more preferably 3×10⁻⁹ M or less, even more preferably 2×10⁻⁹ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "C3 aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein. Where a moiety is identified as being "unsubstituted or substituted" or "optionally substituted," in a preferred embodiment such moiety is unsubstituted.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, $C_1$-$C_4$alkyoxy, O(C$_2$-C$_4$ alkylene)OH, and O(C$_2$-C$_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO₂H, —C(=O)NHOH, —C(=O)O(alkyl), —C(=O)O(hydroxyalkyl), —C(=O)NH₂, —C(=O)NH(alkyl), —C(=O)N(alkyl)₂, —OC(=O)(alkyl), —OC(=O)(hydroxyalkyl), —OC(=O)O(alkyl), —OC(=O)O(hydroxyalkyl), —OC(=O)NH₂, —OC(=O)NH(alkyl), —OC(=O)N(alkyl)₂, azido, —NH₂, —NH(alkyl), —N(alkyl)₂, —NH(aryl), —NH(hydroxyalkyl), —NHC(=O)(alkyl), —NHC(=O)H, —NHC(=O)NH₂, —NHC(=O)NH(alkyl), —NHC(=O)N(alkyl)₂, —NHC(=NH)NH₂, —OSO₂(alkyl), —SH, —S(alkyl), —S(aryl), —S(cycloalkyl), —S(=O)alkyl, —SO₂(alkyl), —SO₂NH₂, —SO₂NH(alkyl), and —SO₂N(alkyl)₂. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO₂H, —C(=O)NHOH, —C(=O)O(alkyl), —C(=O)O(hydroxyalkyl), —C(=O)NH₂, —C(=O)NH(alkyl), —C(=O)N(alkyl)₂, —OC(=O)(alkyl), —OC(=O)(hydroxyalkyl), —OC(=O)O(alkyl), —OC(=O)O(hydroxyalkyl), —OC(=O)NH₂, —OC(=O)NH(alkyl), —OC(=O)N(alkyl)₂, —NH₂, —NH(alkyl), —N(alkyl)₂, —NH(aryl), —NHC(=O)(alkyl), —NHC(=O)H, —NHC(=O)NH₂, —NHC(=O)NH(alkyl), —NHC(=O)N(alkyl)₂, and —NHC(=NH)NH₂. Especially preferred are $C_1$-$C_4$ alkyl, cyano, nitro, halo, and C1-C4alkoxy.

Where a range is stated, as in "$C_1$-$C_5$ alkyl" or "5 to 10%," such range includes the end points of the range, as in $C_1$ and $C_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include $C_1$-$C_5$ alkyl, $C_2$-$C_5$ alkenyl or $C_2$-$C_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line ( ~~~~ ) transverse to a bond or an asterisk (*) at the end of the bond denotes a covalent attachment site. For instance, a statement that R is

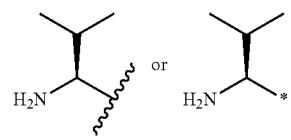

in the formula

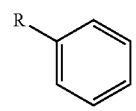

refers to

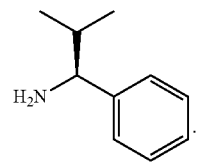

In the formulae of this specification, a bond traversing an aromatic ring between two carbons thereof means that the group attached to the bond may be located at any of the available positions of the aromatic ring. By way of illustration, the formula

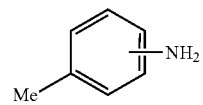

represents

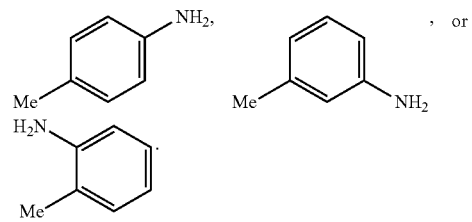

Dimers

A preferred embodiment of benzodiazepine dimers according to formula (I) has a structure represented by formula (I'), where the meaning of the variables in formula (I') are as defined in formula (I):

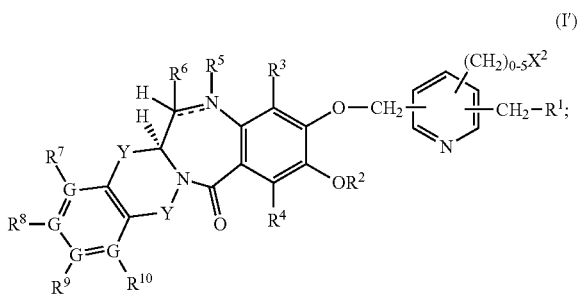

that is, formula (I') differs from formula (I) in that X is

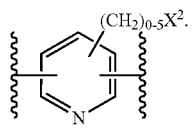

In formula (I) and subgenera thereof, and related formulae for dimer-linker compounds and conjugates, the following preferences apply unless a more specific preference is indicated in the context of a particular formula:

(a) Where a formula comprises two benzodiazepine ring systems with double line ====, no more than one double line ==== represents a single bond. Rather, preferably, both are double bonds or, alternatively, one is a single bond and the other is a double bond.

(b) Each $R^2$, where present in a formula, is Me, and, more preferably, each $R^2$ is Me and each $R^3$, $R^4$, $R^7$, $R^8$, and $R^{10}$, where present in a formula, is H.

(c) Each Y, where present in a formula, is $CH_2$.

(d) Each $R^9$, where present in a formula, is independently H, OH, OMe, $NH_2$, $NMe_2$, $O(CH_2CH_2O)_{1-8}Me$, $OCH_2CH_2OH$, or

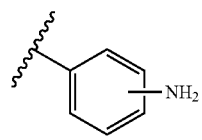

(especially the para- isomer).

(e) Where present in a formula, each G' is C and Y' and Y" are both $CH_2$ or one G' is N, Y' is $CH_2$, and Y" is absent.

(f) Where present in a formula, $R^{11}$ is H, $=CH_2$, $CH=CHMe$, $=CHMe$, $C\equiv CCH_2NH_2$,

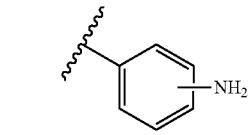

(especially the para- isomer), or

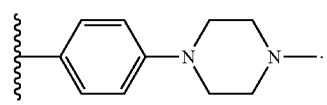

(h) The bridging group

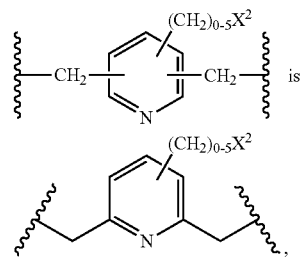

and more preferably is

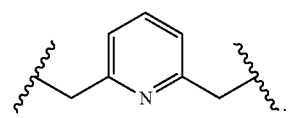 [SMILES: *Cc1cccc(C*)n1]

(i) The moiety $(CH_2)_{0-5}X^2$ in the bridging group

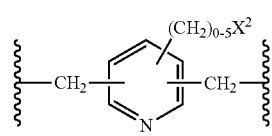

preferably is H, OH, OMe, Me, or $CH_2OH$.

A dimer of this invention can be a THIQ-THIQ dimer; that is, in formula (I) $R^1$ is according to formula (Ia). Such a dimer can be represented by formula (IIa)

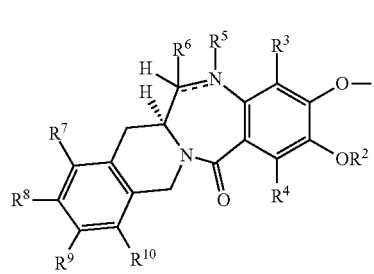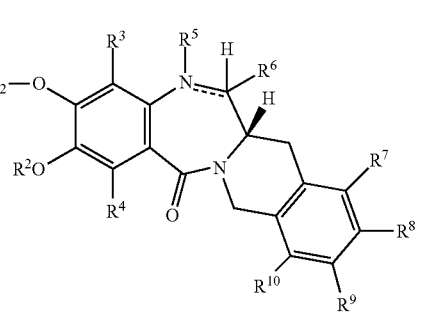

wherein
X, $R^2$, $R^3$, $R^4$, $R^5$, $R^6$, $R^7$, $R^8$, $R^9$, $R^{10}$, the double line ====, and $X^2$ are as defined in respect of formula (I) in the BRIEF SUMMARY OF THE INVENTION section hereinabove.

Preferred THIQ-THIQ dimers according to formula (IIa) have a structure represented by formula (IIa'), where the variables in formula (IIa') are as defined in respect of formula (I) in the BRIEF SUMMARY OF THE INVENTION section hereinabove:

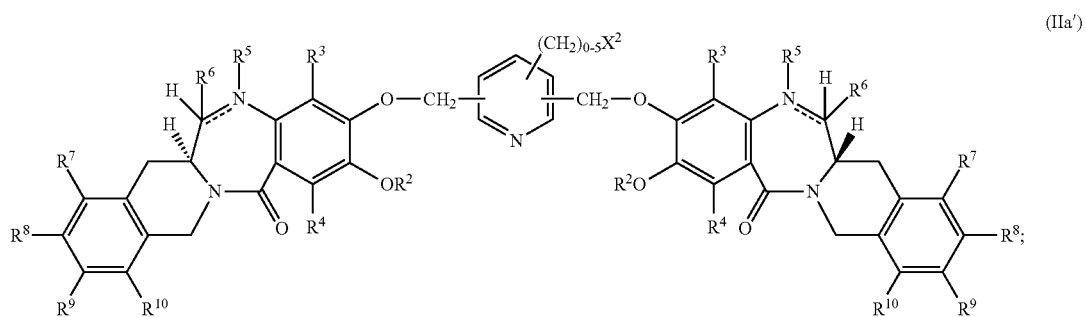

(IIa')

That is, formula (IIa') differs from in formula (IIa) in that X is

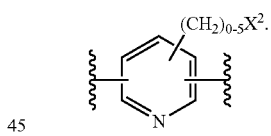

In another preferred embodiment according the formula (IIa), THIQ-THIQ dimers are represented by formula (IIa"):

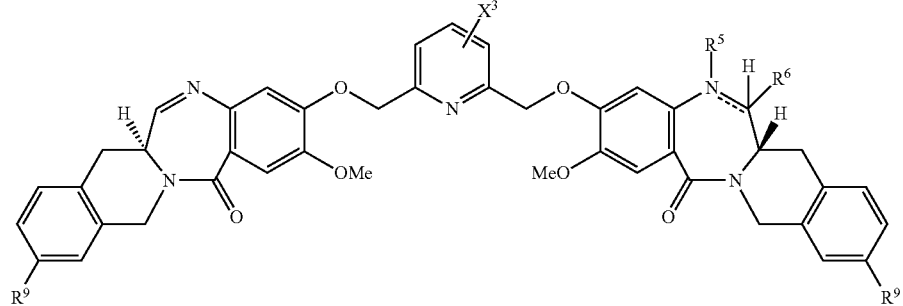

(IIa")

wherein
- R⁵ is H if the double line ==== to the N to which it is bonded is a single bond and absent if the double line ==== is a double bond;
- R⁶ is H if the double line ==== to the C to which it is bonded is a single bond and absent if the double line ==== is a double bond;
- each R⁹ is independently H, OH, OMe, NH₂, NMe₂, O(CH₂CH₂O)₁₋₈Me, OCH₂CH₂OH, or

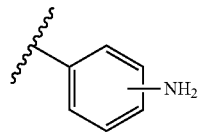

(especially the para- isomer); and
X³ is H, OH, OMe, Me, CH₂OH, O(allyl), Cl, or CO₂Me.

Specific examples of THIQ-THIQ dimers include:

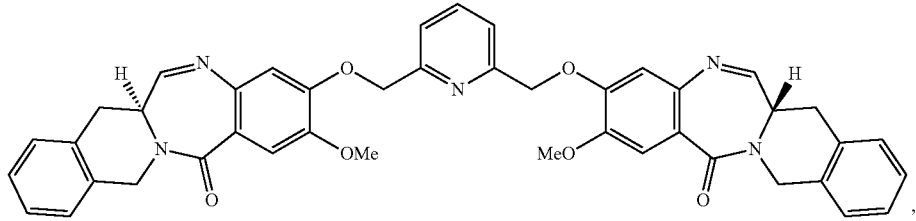

(IIa-01)

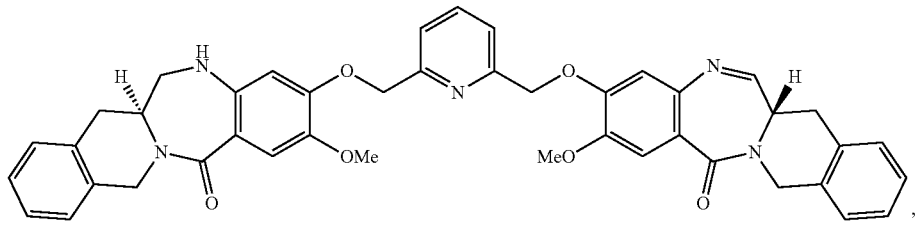

(IIa-02)

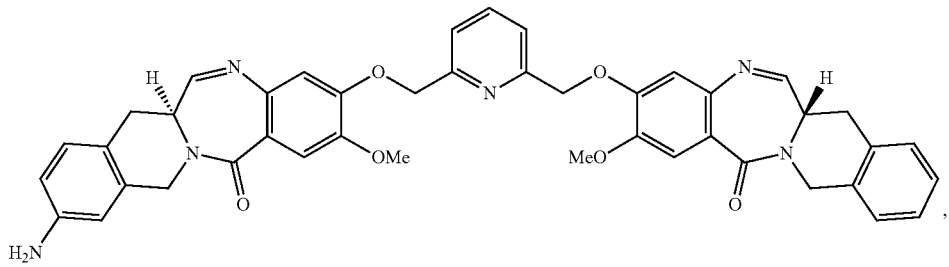

(IIa-03)

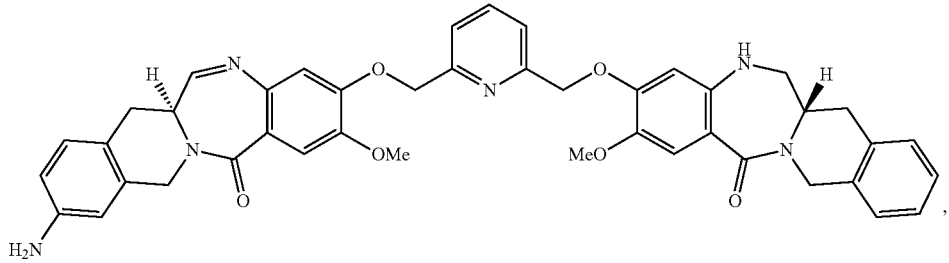

(IIa-04)

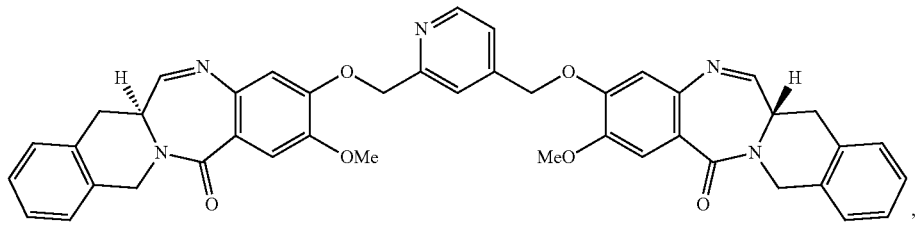

(IIa-05)

-continued
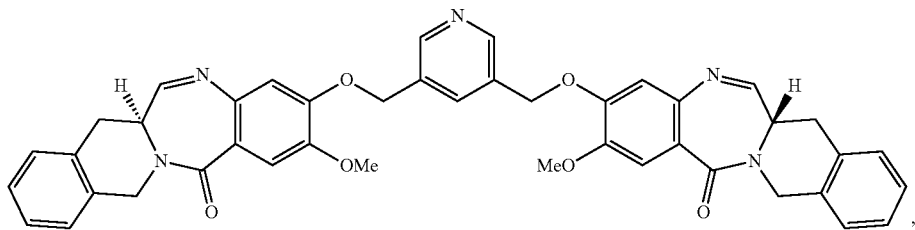
(IIa-06)
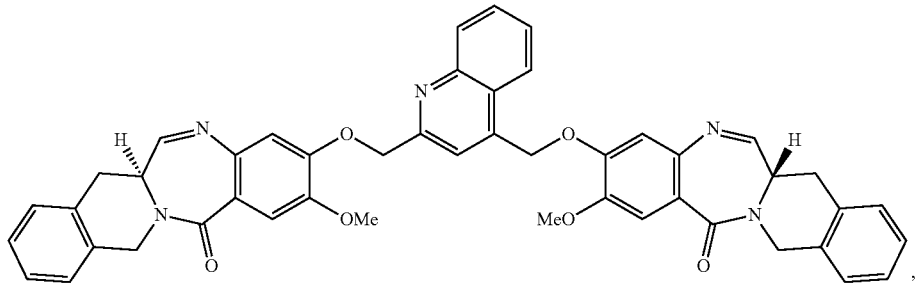
(IIa-07)
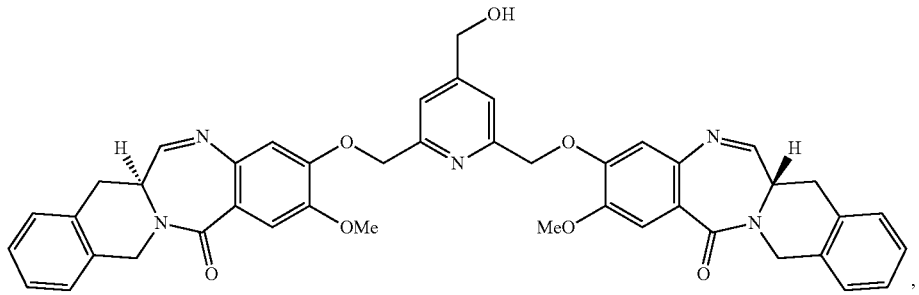
(IIa-08)
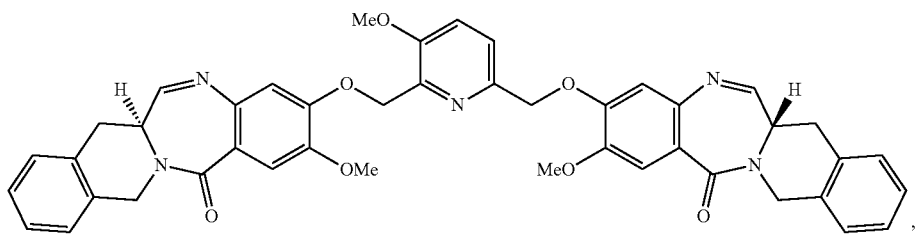
(IIa-09)
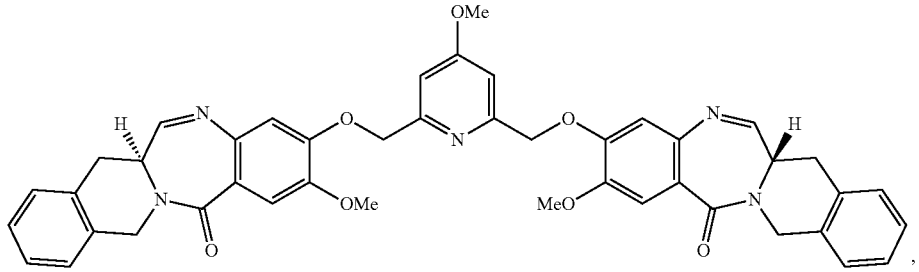
(IIa-10)
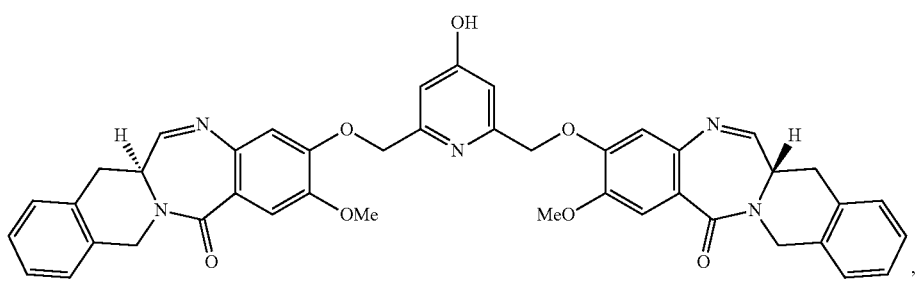
(IIa-11)

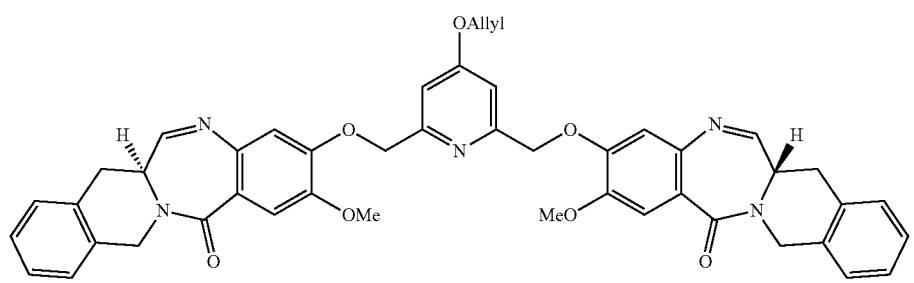
(IIa-12)
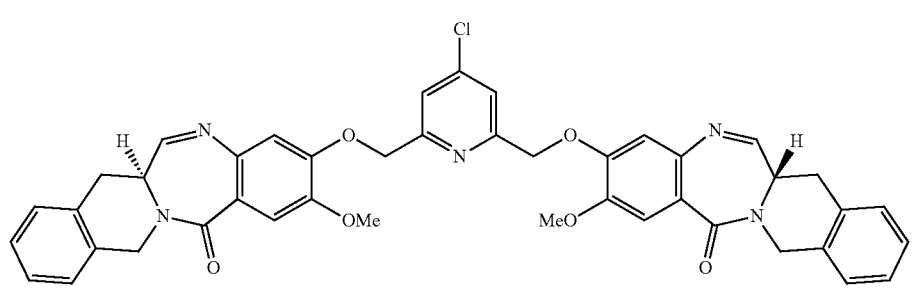
(IIa-13)
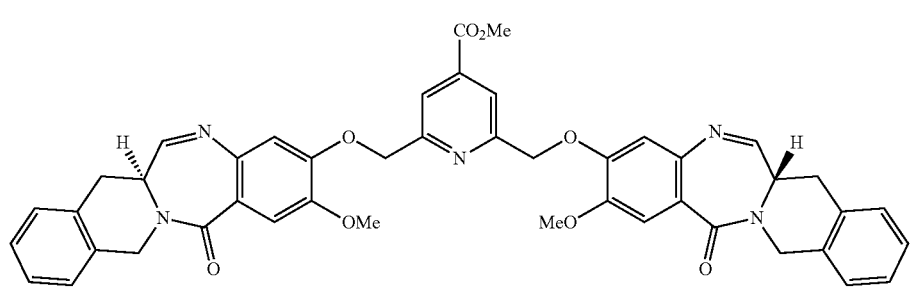
(IIa-14)
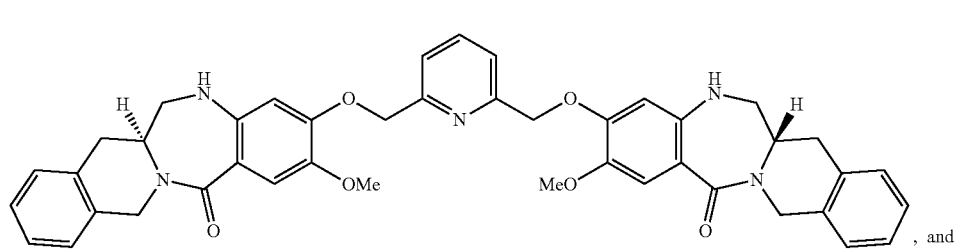
, and
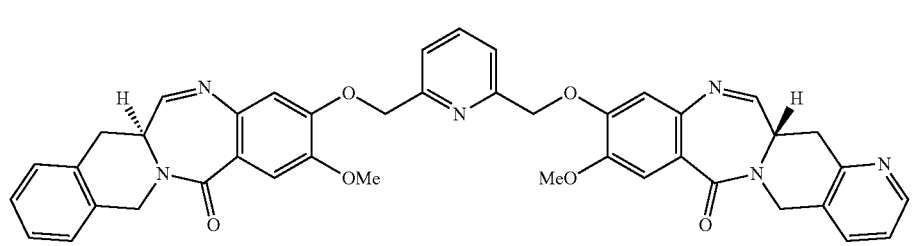
(IIa-16)

In another embodiment, a dimer of this invention is a THIQ-PBD dimer; that is, in formula (I), $R^1$ is according to formula (Ib). Such a dimer can be represented by formula (IIb):

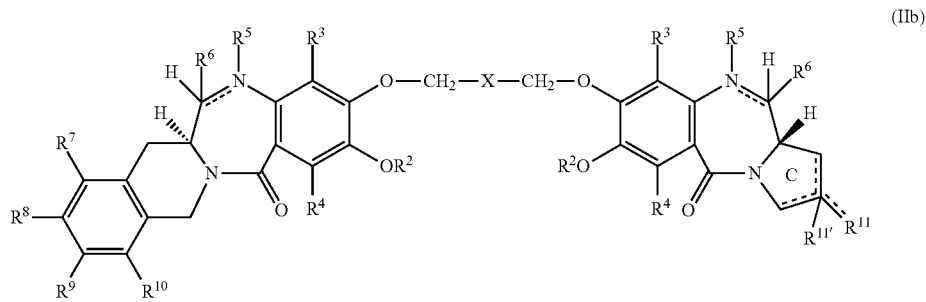

(IIb)

wherein
X, $R^2$, $R^3$, $R^4$, $R^5$, $R^6$, $R^7$, $R^8$, $R^9$, $R^{10}$, $R^{11}$, $R^{11'}$, the double line ==== the dotted lines in ring C, and $X^2$ are as defined in respect of formula (I) in the BRIEF SUMMARY OF THE INVENTION section hereinabove.

A preferred THIQ-PBD dimer according to formula (IIb) has a structure represented by formula (IIb'), wherein the variables in formula (IIb') are as defined in respect of formula (I) in the BRIEF SUMMARY OF THE INVENTION section hereinabove.

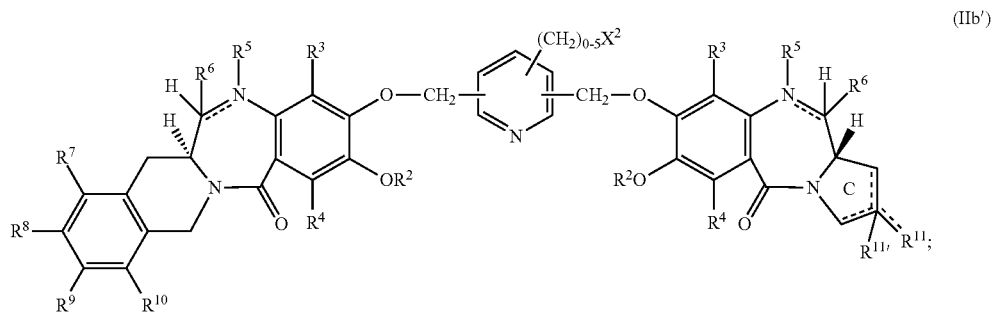

(IIb')

That is, formula (IIb') differs from formula (IIb) in that X is

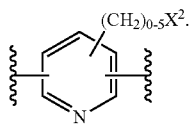

Another preferred THIQ-PBD dimer according to formula (IIb) is represented by formula (IIb"):

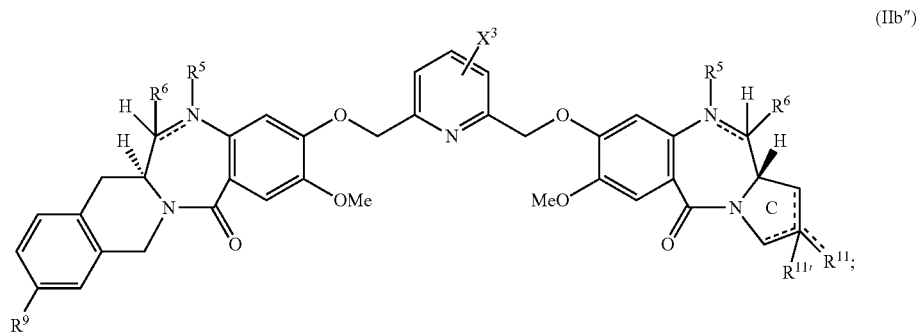

(IIb")

wherein
R⁹ is H, OH, OMe, NH₂, NMe₂, O(CH₂CH₂O)₁₋₈Me, OCH₂CH₂OH, or

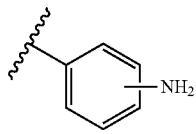

(especially the para- isomer);
R¹¹ is H, =CH₂, CH=CHMe, =CHMe, C≡CCH₂NH₂,

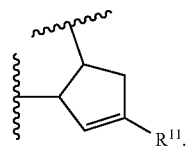

In another embodiment, a dimer of this invention comprises a benzodiazepine unit having a THIQ ring system and a benzodiazepine unit having an azaindoline (AZI) ring system ("THIQ-AZI dimer"). Such a dimer can be represented by formula (IIc):

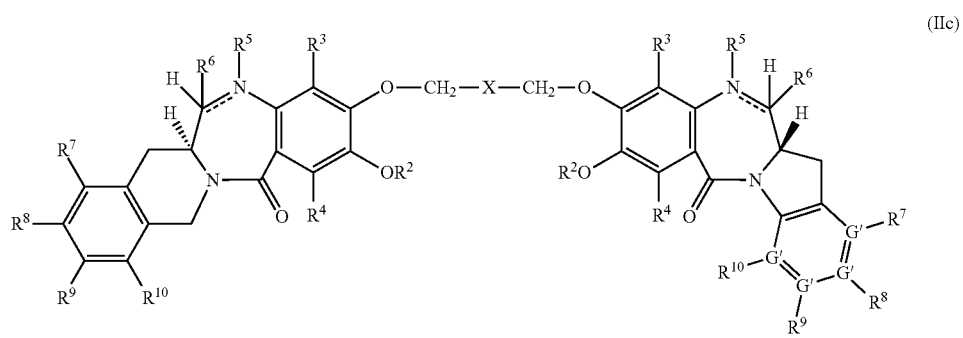

(IIc)

wherein

X, R², R³, R⁴, R⁷, R⁸, R⁹, R¹⁰, the double line ====, and X² are as defined in respect of formula (I) in the BRIEF SUMMARY OF THE INVENTION section hereinabove;

one G' is N and the others are C;

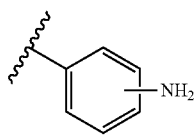

(especially the para- isomer), or

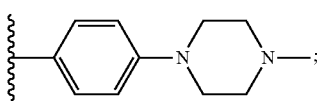

R¹¹ is absent if a C1-C2, C2-C3, or C2-R¹¹ double bond is present and otherwise is H;
X³ is H, OH, OMe, Me, or CH₂OH;
at least one of the double lines ==== in a diazepine ring system is a double bond;
R⁵ is H if the double line ==== to the N to which it is attached is a single bond and absent if the double line ==== is a double bond; and
R⁶ is H if the double line ==== to the C to which it is attached is a single bond and absent if the double line ==== is a double bond.
Preferably, in formula (IIb), (IIb'), and (IIb''),

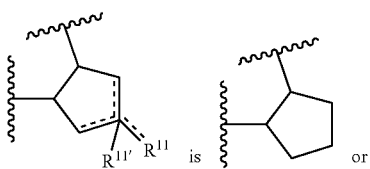

at least one of the double lines ==== in a diazepine ring system is a double bond;

R⁵ is H if the double line ==== to the N to which it is attached is a single bond and absent if the double line ==== is a double bond; and R⁶ is H if the double line ==== to the C to which it is attached is a single bond and absent if the double line ==== is a double bond.

A preferred THIQ-AZI dimer according to formula (IIc) has a structure represented by formula (IIc'), wherein the variables are as defined in respect of formula (I) in the BRIEF SUMMARY OF THE INVENTION section hereinabove

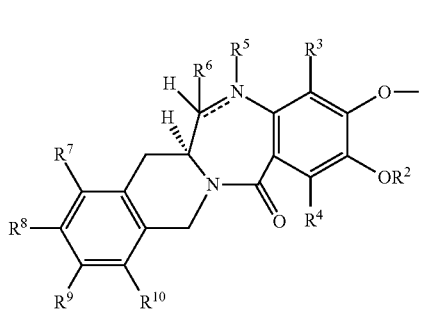 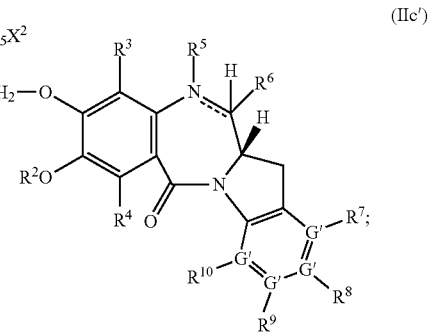

(IIc')

that is, formula (IIc') differs from formula (IIc) in that X is

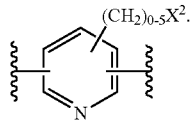

Conjugates
General

Dimers of this invention can be used as therapeutic agents per se, but preferably are used as conjugates with a targeting moiety that specifically or preferentially binds to a chemical entity on a cancer cell. Preferably, the targeting moiety is an antibody or antigen binding portion thereof and the chemical entity is a tumor associated antigen.

Thus, another embodiment of this invention is a conjugate comprising dimer of this invention and a ligand, represented by formula (II)

$$[D(X^D)_a(C)_c(X^Z)_b]_m Z \qquad (II)$$

where Z is a ligand, D is a dimer of this invention, and $-(X^D)_a C(X^Z)_b-$ are collectively referred to as a "linker moiety" or "linker" because they link Z and D. Within the linker, C is a cleavable group designed to be cleaved at or near the site of intended biological action of dimer D; $X^D$ and $X^Z$ are referred to as spacer moieties (or "spacers") because they space apart D and C and C and Z, respectively; subscripts a, b, and c are independently 0 or 1 (that is, the presence of $X^D$, $X^Z$ and C are optional). Subscript m is 1, 2, 3, 4, 5, 6, 7, 8, 9, or 10 (preferably 1, 2, 3, or 4). D, $X^D$, C, $X^Z$ and Z are more fully described hereinbelow.

Ligand Z—for example an antibody—performs a targeting function. By binding to a target tissue or cell where its antigen or receptor is located, ligand Z directs the conjugate there. (When ligand Z is an antibody, the conjugate is sometimes referred to as antibody-drug conjugate (ADC) or an immunoconjugate. Preferably, the target tissue or cell is a cancer tissue or cell and the antigen or receptor is a tumor-associated antigen, that is, an antigen that is uniquely expressed by cancerous cells or is overexpressed by cancer cells, compared to non-cancerous cells. Cleavage of group C at the target tissue or cell releases dimer D to exert its cytotoxic effect locally. In some instances, the conjugate is internalized into a target cell by endocytosis and cleavage takes place within the target cell. In this manner, precise delivery of dimer D is achieved at the site of intended action, reducing the dosage needed. Also, dimer D is normally biologically inactive (or significantly less active) in its conjugated state, thereby reducing undesired toxicity against non-target tissue or cells. As anticancer drugs are often highly toxic to cells in general, this is an important consideration.

As reflected by the subscript m, each molecule of ligand Z can conjugate with more than one dimer D, depending on the number of sites ligand Z has available for conjugation and the experimental conditions employed. Those skilled in the art will appreciate that, while each individual molecule of ligand Z is conjugated to an integer number of dimers D, a preparation of the conjugate may analyze for a non-integer ratio of dimers D to ligand Z, reflecting a statistical average. This ratio is referred to as the substitution ratio (SR) or, synonymously, the drug-antibody ratio (DAR).

Ligand Z

Preferably, ligand Z is an antibody. For convenience and brevity and not by way of limitation, the detailed subsequent discussion herein about the conjugation of ligand Z is written in the context of its being an antibody, but those skilled in the art will understand that other types of ligand Z can be conjugated, mutatis mutandis. For example, conjugates with folic acid as the ligand can target cells having the folate receptor on their surfaces (Leamon et al., Cancer Res. 2008, 68 (23), 9839). For the same reason, the detailed discussion below is primarily written in terms of a 1:1 ratio of antibody Z to analog D (m=1).

Preferably, ligand Z is an antibody against a tumor associated antigen, allowing the selective targeting of cancer cells. Examples of such antigens include: mesothelin, prostate specific membrane antigen (PSMA), CD19, CD22, CD30, CD70, B7H3, B7H4 (also known as O8E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. No. 8,609,816 B2 (2013; B7H4, also known as O8E; in particular antibodies 2A7, 1G11, and 2F9); Rao-Naik et al., U.S. Pat. No. 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Vistica et al., U.S. Pat. No. 8,383,118 B2 (2013, fucosyl-GM1, in particular antibodies 5B1, 5B1a, 7D4, 7E4, 13B8, and 18D5) Korman et al., U.S. Pat. No. 8,008,449 B2

(2011; PD-1; in particular antibodies 17D8, 2D3, 4H1, 5C4, 4A11, 7D3, and 5F4); Huang et al., US 2009/0297438 A1 (2009; PSMA. in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Terrett et al., U.S. Pat. No. 8,680,247 B2 (2014; glypican-3; in particular antibodies 4A6, 11E7, and 16D10); Harkins et al., U.S. Pat. No. 7,335,748 B2(2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-L1; in particular antibodies 3G10, 12A4, 10A5, 5F8, 10H10, 1B12, 7H1, 11E6, 12B7, and 13G4); the disclosures of which are incorporated herein by reference. Each of the aforementioned antibodies can be used in an ADC with a dimer of this invention.

Ligand Z can also be an fragment antigen binding fragment of an antibody or an antibody mimetic, such as an affibody, a domain antibody (dAb), a nanobody, a unibody, a DARPin, an anticalin, a versabody, a duocalin, a lipocalin, or an avimer.

Any one of several different reactive groups on ligand Z can be a conjugation site, including ε-amino groups in lysine residues, pendant carbohydrate moieties, carboxylic acid groups, disulfide groups, and thiol groups. Each type of reactive group represents a trade-off, having some advantages and some disadvantages. For reviews on antibody reactive groups suitable for conjugation, see, e.g., Garnett, *Adv. Drug Delivery Rev.* 53 (2001), 171-216 and Dubowchik and Walker, *Pharmacology & Therapeutics* 83 (1999), 67-123, the disclosures of which are incorporated herein by reference.

In one embodiment, ligand Z is conjugated via a lysine ε-amino group. Most antibodies have multiple lysine ε-amino groups, which can be conjugated via amide, urea, thiourea, or carbamate bonds using techniques known in the art. However, it is difficult to control which and how many ε-amino groups react, leading to potential batch-to-batch variability in conjugate preparations. Also, conjugation may cause neutralization of a protonated ε-amino group important for maintaining the antibody's native conformation or may take place at a lysine near or at a ligand or antigen binding site, neither being a desirable occurrence.

In another embodiment, ligand Z can be conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be converted to a more stable amine group by reduction with $NaCNBH_3$. For additional disclosures on conjugation via carbohydrate side chains, see, e.g., Rodwell et al., *Proc. Nat'l Acad. Sci. USA* 83, 2632-2636 (1986); the disclosure of which is incorporated herein by reference. As with lysine ε-amino groups, there are concerns regarding reproducibility of the location of the conjugation site(s) and stoichiometry.

In yet another embodiment, ligand Z can be conjugated via a carboxylic acid group, such as the side-chain carboxyl of a glutamic or aspartic acid. In one embodiment, a terminal carboxylic acid group is functionalized to generate a carbohydrazide, which is then reacted with an aldehyde-bearing conjugation moiety. See Fisch et al., *Bioconjugate Chemistry* 1992, 3, 147-153.

In yet another embodiment, antibody Z can be conjugated via a disulfide group bridging a cysteine residue on antibody Z and a sulfur on the other portion of the conjugate. Some antibodies lack free thiol (sulfhydryl) groups but have disulfide groups, for example in the hinge region. In such case, free thiol groups can be generated by reduction of native disulfide groups. The thiol groups so generated can then be used for conjugation. See, e.g., Packard et al., *Biochemistry* 1986, 25, 3548-3552; King et al., *Cancer Res.* 54, 6176-6185 (1994); and Doronina et al., *Nature Biotechnol.* 21(7), 778-784 (2003); the disclosures of which are incorporated herein by reference. Again, there are concerns regarding conjugation site location and stoichiometry and the possible disruption of antibody native conformation.

A number of methods are known for introducing free thiol groups into antibodies without breaking native disulfide bonds, which methods can be practiced with a ligand Z of this invention. Depending on the method employed, it may be possible to introduce a predictable number of free sulfhydryls at predetermined locations. In one approach, mutated antibodies are prepared in which a cysteine is substituted for another amino acid. See, for example, Eigenbrot et al., U.S. Pat. No. 7,521,541 B2 (2009); Chilkoti et al., *Bioconjugate Chem.* 1994, 5, 504-507; Urnovitz et al., U.S. Pat. No. 4,698,420 (1987); Stimmel et al., *J. Biol. Chem.*, 275 (39), 30445-30450 (2000); Bam et al., U.S. Pat. No. 7,311,902 B2 (2007); Kuan et al., *J. Biol. Chem.*, 269 (10), 7610-7618 (1994); Poon et al., *J. Biol. Chem.*, 270 (15), 8571-8577 (1995). In another approach, an extra cysteine is added to the C-terminus. See, e.g. Cumber et al., *J. Immunol.*, 149, 120-126 (1992); King et al, *Cancer Res.*, 54, 6176-6185 (1994); Li et al., *Bioconjugate Chem.*, 13, 985-995 (2002); Yang et al., *Protein Engineering*, 16, 761-770 (2003); and Olafson et al., *Protein Engineering Design & Selection*, 17, 21-27 (2004). A preferred method for introducing free cysteines is that taught by Liu et al., U.S. Pat. No. 8,865,875 B2 (2014), in which a cysteine bearing amino acid sequence is added to the C-terminus of the heavy chain of an antibody. This method introduces a known number of cysteine residues (one per heavy chain) at a known location awat from the antigen binding site. The disclosures of the documents cited in this paragraph are all incorporated herein by reference.

In yet another embodiment, lysine ε-amino groups can be modified with reagents such as 2-iminothiolane, 2-iminothiacyclohexane, or N-succinimidyl-3-(2-pyridyldithio)-propionate (SPDP), converting an ε-amino group into a thiol or disulfide group—creating a cysteine surrogate, as it were. However, this method suffers from the same conjugation location and stoichiometry limitations associated with ε-amino groups proper.

Linker Components

As noted above, the linker portion of a conjugate of this invention comprises up to three elements: a cleavable group C and optional spacers $X^Z$ and $X^D$.

Cleavable group C is a group cleavable under physiological conditions, preferably selected such that it is relatively stable while the conjugate is in general circulation in the blood plasma, but is readily cleaved once the conjugate reaches its site of intended action, that is, near, at, or within the target cell. Preferably, the conjugate is internalized by a target cell upon binding of antibody Z to an antigen displayed on the surface of the target cell. Subsequently, cleavage of group C occurs in a vesicular body of the target cell (an early endosome, a late endosome, or, especially, a lysosome).

In one embodiment, group C is a pH sensitive group. The pH in blood plasma is slightly above neutral, while the pH inside a lysosome is acidic, circa 5. Thus, a group C whose cleavage is acid catalyzed will cleave at a rate several orders of magnitude faster inside a lysosome than in the blood plasma rate. Examples of suitable acid-sensitive groups include cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 102, 1048-1054 (1981) and Yang et al., *Proc. Natl Acad. Sci* (*USA*), 85, 1189-1193 (1988); the disclosures of which are incorporated herein by reference.

In another embodiment, group C is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. For additional disclosures relating to disulfide cleavable groups in conjugates, see, e.g., Thorpe et al., *Cancer Res.* 48, 6396-6403 (1988); Santi et al., U.S. Pat. No. 7,541,530 B2 (2009); Ng et al., U.S. Pat. No. 6,989,452 B2 (2006); Ng et al., WO 2002/096910 A1; Boyd et al., U.S. Pat. No. 7,691,962 B2; and Sufi et al., US 2010/0145036 A1; the disclosures of which are incorporated herein by reference.

A preferred cleavable group is a peptide that is cleaved selectively by a protease inside the target cell, as opposed to by a protease in the serum. Typically, a cleavable peptide group comprises from 1 to 20 amino acids, preferably from 1 to 6 amino acids, more preferably from 1 to 3 amino acids. The amino acid(s) can be natural and/or non-natural α-amino acids. Natural amino acids are those encoded by the genetic code, as well as amino acids derived therefrom, e.g., hydroxyproline, γ-carboxyglutamate, citrulline, and O-phosphoserine. In this context, the term "amino acid" also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The amino acid can be of the "L" stereochemistry of the genetically encoded amino acids, as well as of the enantiomeric "D" stereochemistry.

Preferably, group C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

For conjugates that are not intended to be internalized by a cell, a group C can be chosen such that it is cleaved by a protease present in the extracellular matrix in the vicinity of the target tissue, e.g., a protease released by nearby dying cells or a tumor-associated protease. Exemplary extracellular tumor-associated proteases are matrix metalloproteases (MMP), thimet oligopeptidase (TOP) and CD 10.

For conjugates that are designed to be internalized by a cell, group C preferably comprises an amino acid sequence selected for cleavage by an endosomal or lysosomal protease, especially the latter. Non-limiting examples of such proteases include cathepsins B, C, D, H, L and S, especially cathepsin B. Cathepsin B preferentially cleaves peptides at a sequence -$AA^2$-$AA^1$- where $AA^1$ is a basic or strongly hydrogen bonding amino acid (such as lysine, arginine, or citrulline) and $AA^2$ is a hydrophobic amino acid (such as phenylalanine, valine, alanine, leucine, or isoleucine), for example Val-Cit (where Cit denotes citrulline) or Val-Lys. (Herein, amino acid sequences are written in the N-to-C direction, as in $H_2N$-$AA^2$-$AA^1$-$CO_2H$, unless the context clearly indicates otherwise.) Lys-Val-Ala, Asp-Val-Ala, Val-Ala, Lys-Val-Cit, and Asp-Val-Cit are also substrate peptide motifs for cathpsin B, although in some instances the cleavage rate may be slower. For additional information regarding cathepsin-cleavable groups, see Dubowchik et al., *Biorg. Med. Chem. Lett.* 8, 3341-3346 (1998); Dubowchik et al., *Bioorg. Med. Chem. Lett.,* 8 3347-3352 (1998); and Dubowchik et al., *Bioconjugate Chem.* 13, 855-869 (2002); the disclosures of which are incorporated by reference. Another enzyme that can be utilized for cleaving peptidyl linkers is legumain, a lysosomal cysteine protease that preferentially cleaves at Ala-Ala-Asn.

In one embodiment, Group C is a peptide comprising a two-amino acid sequence -$AA^2$-$AA^1$- wherein $AA^1$ is lysine, arginine, or citrulline and $AA^2$ is phenylalanine, valine, alanine, leucine or isoleucine. In another embodiment, C consists of a sequence of one to three amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu.

The preparation and design of cleavable groups C consisting of a single amino acid is disclosed in Chen et al., U.S. Pat. No. 8,664,407 B2 (2014), the disclosure of which is incorporated herein by reference.

Group C can also be a photocleavable one, for example a nitrobenzyl ether that is cleaved upon exposure to light.

Group C can be bonded directly to antibody Z or analog D; i.e. spacers $X^Z$ and $X^D$, as the case may be, can be absent. For example, if group C is a disulfide, one of the two sulfurs can be a cysteine residue or its surrogate on antibody Z. Or, group C can be a hydrazone bonded to an aldehyde on a carbohydrate side chain of the antibody. Or, group C can be a peptide bond formed with a lysine ε-amino group of antibody Z. In a preferred embodiment, dimer D is directly bonded to group C via a peptidyl bond to a carboxyl or amine group in dimer D.

When present, spacer $X^Z$ provides spatial separation between group C and antibody Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

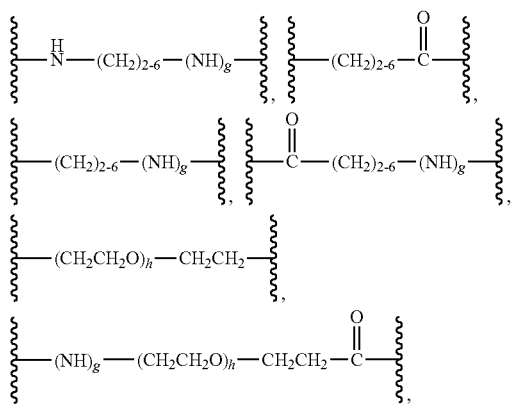

and combinations thereof,
where the subscript g is 0 or 1 and the subscript h is 1 to 24, preferably 2 to 4. These segments can be combined, such as illustrated below:

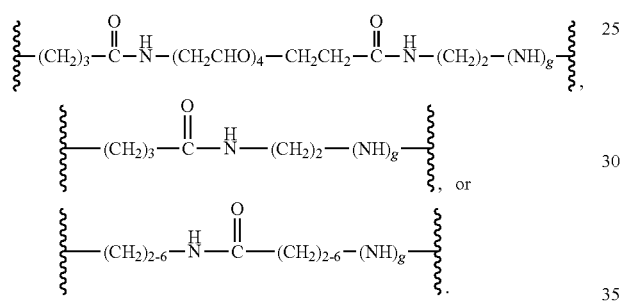

Spacer $X^D$, if present, provides spatial separation between group C and dimer D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, as described above in the context of spacer $X^Z$.

Spacers $X^Z$ and/or $X^D$, where present, preferably provide a linear separation of from 4 to 25 atoms, more preferably from 4 to 20 atoms, between Z and C or D and C, respectively.

The linker can perform other functions in addition to covalently linking the antibody and the drug. For instance, the linker can contain poly(ethylene glycol) (PEG) groups, which enhance solubility either during the performance the conjugation chemistry or in the final ADC product. Where a PEG group is present, it may be incorporated into either spacer $X^Z$ of $X^D$, or both. The number of repeat units in a PEG group can be from 2 to 20, preferably between 4 and 10.

Either spacer $X^Z$ or $X^D$, or both, can comprise a self-immolating moiety. A self-immolating moiety is a moiety that (1) is bonded to group C and either antibody Z or dimer D and (2) has a structure such that cleavage from group C initiates a reaction sequence resulting in the self-immolating moiety disbonding itself from antibody Z or dimer D, as the case may be. In other words, reaction at a site distal from antibody Z or dimer D (cleavage from group C) causes the $X^Z$—Z or the $X^D$-D bond to rupture as well. The presence of a self-immolating moiety is desirable in the case of spacer $X^D$ because, if, after cleavage of the conjugate, spacer $X^D$ or a portion thereof were to remain attached to dimer D, the biological activity of the latter may be impaired. The use of a self-immolating moiety is especially desirable where cleavable group C is a polypeptide, in which instance the self-immolating moiety typically is located adjacent thereto.

Exemplary self-immolating moieties (i)-(vii) bonded to a hydroxyl or amino group on a partner molecule D are shown below:

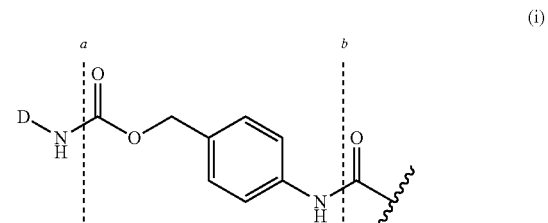

(i)

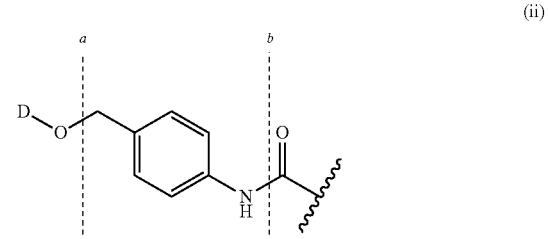

(ii)

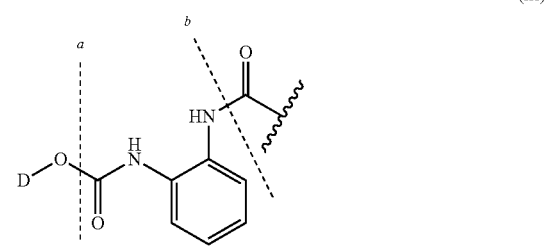

(iii)

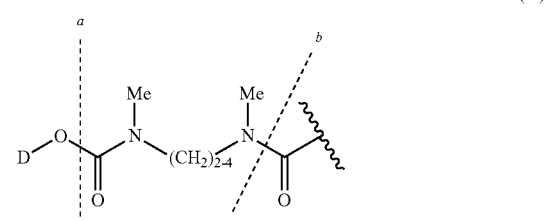

(iv)

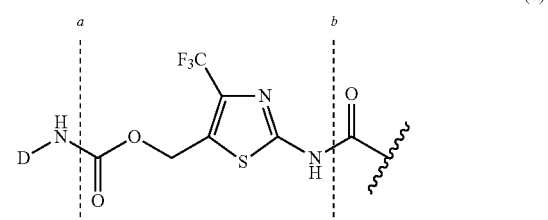

(v)

(vi)

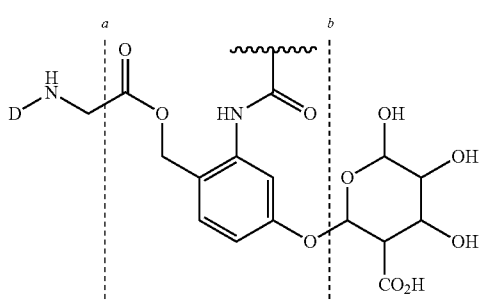

(vii)

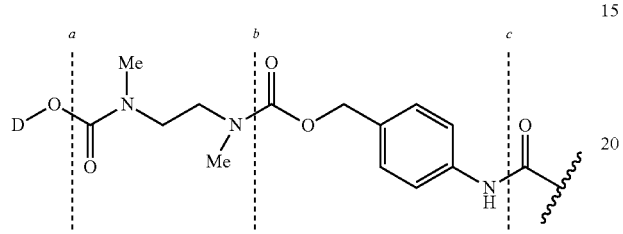

The self-immolating moiety is the structure between dotted lines a and b (or dotted lines b and c), with adjacent structural features shown to provide context. Self-immolating moieties (i) and (v) are bonded to a dimer D-NH$_2$ (i.e., dimer D is conjugated via an amino group), while self-immolating moieties (ii), (iii), and (iv) are bonded to a dimer D-OH (i.e., dimer D is conjugated via a hydroxyl or carboxyl group). Cleavage of the amide bond at dotted line b (e.g., by a peptidase) releases the amide nitrogen as an amine nitrogen, initiating a reaction sequence that results in the cleavage of the bond at dotted line a and the consequent release of D-OH or D-NH$_2$, as the case may be. Alternatively, the cleavage that triggers the self-immolating reaction can be by a different type of enzyme, for example by a β-glucuronidase, as in the instance of structure (vi). In some instances, self-immolating groups can be used in tandem, as shown by structure (vii). In such case, cleavage at dotted line c triggers self-immolation of the moiety between dotted lines b and c by a 1,6-elimination reaction, followed by self-immolation of the moiety between dotted lines a and b by a cyclization-elimination reaction. For additional disclosures regarding self-immolating moieties, see Carl et al., *J. Med. Chem.*, 24 (3), 479-480 (1981); Carl et al., WO 81/01145 (1981); Dubowchik et al., *Pharmacology & Therapeutics*, 83, 67-123 (1999); Firestone et al., U.S. Pat. No. 6,214,345 B1 (2001); Toki et al., *J. Org. Chem.* 67, 1866-1872 (2002); Doronina et al., *Nature Biotechnology* 21 (7), 778-784 (2003) (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; Jeffrey et al., U.S. Pat. No. 8039,273; and Senter et al., US 2003/0096743 A1; the disclosures of which are incorporated by reference. A preferred self-immolating group is p-aminobenzyl oxycarbonyl (PABC) group, as shown in structure (i).

In another embodiment, an antibody targeting moiety and the dimer D are linked by a non-cleavable linker, i.e., element C is absent. Degradation of the antibody eventually reduces the linker to a small appended moiety that does not interfere with the biological activity of dimer D.

Conjugation Techniques

Conjugates of this invention preferably are made by first preparing a compound comprising an analog of this invention (represented by D in the formulae below) and linker $(X^D)_a(C)_c(X^Z)_b$ (where $X^D$, C, $X^Z$, a, b, and c are as defined for formula (II)) to form an analog-linker composition represented by formula (III):

$$D\text{-}(X^D)_a(C)_c(X^Z)_b\text{---}R^{31} \qquad (III)$$

where $R^{31}$ is a functional group suitable for reacting with a complementary functional group on antibody Z to form the conjugate. Examples of suitable groups $R^{31}$ include amino, azide, thiol, cyclooctyne,

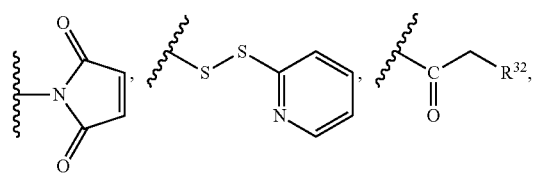

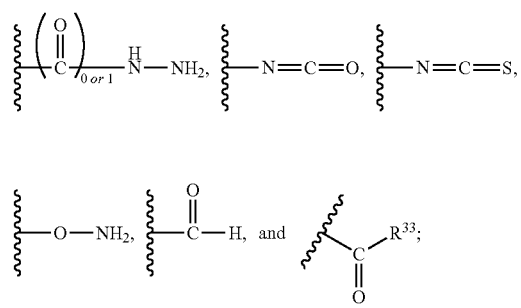

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties $D\text{-}(X^D)_a C(X^Z)_b\text{---}R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847,105 B2 (2010); Gangwar et al., U.S. Pat. No. 7,968,586 B2 (2011); Sufi et al., US 2010/0145036 A1; and Chen et al., US 2010/0113476 A1; the disclosures of which are incorporated herein by reference.

Preferably reactive functional group —$R^{31}$ is —NH$_2$, —OH, —CO$_2$H, —SH, maleimido, cyclooctyne, azido (—N$_3$), hydroxylamino (—ONH$_2$) or N-hydroxysuccinimido. Especially preferred functional groups —$R^{31}$ are:

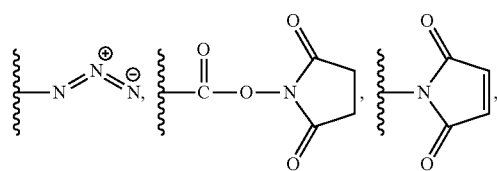

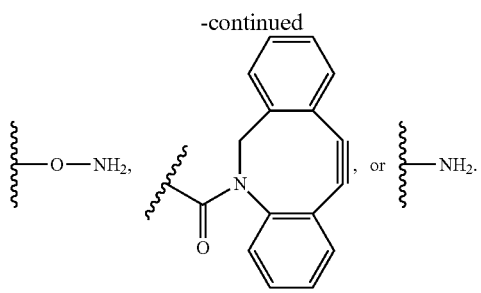

An —OH group can be esterified with a carboxy group on the antibody, for example, on an aspartic or glutamic acid side chain.

A —CO$_2$H group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction. Or, the position of the two groups can be reversed, with the antibody modified to have a maleimide group attached and the drug-linker compound having an —SH group.

Various techniques can be introducing an —SH group into an antibody. In a preferred one, an ε-amino group in the side chain of a lysine residue in the antibody is reacted with 2-iminothiolane to introduce a free thiol (—SH) group. The thiol group can react with a maleimide or other nucleophile acceptor group to effect conjugation:

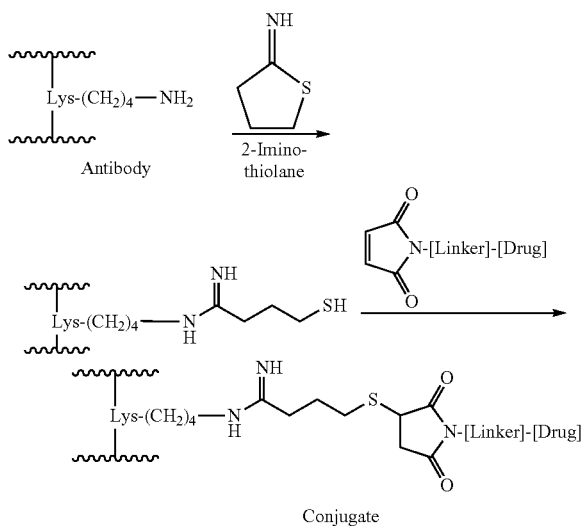

Typically, a thiolation level of two to three thiols per antibody is achieved. For a representative procedure, see Cong et al. 2014, the disclosure of which is incorporated herein by reference. Thus, in one embodiment, an antibody for conjugation to a dimer of this invention has one or more lysine residues (preferably two or three) modified by reaction with iminothiolane.

An —SH group can also be used for conjugation where the antibody has been modified to introduce a maleimide group thereto, in a Michael addition reaction that is the "mirror image" of that described above. Antibodies can be modified to have maleimide groups with N-succinimidyl 4-(maleimidomethyl)-cyclohexanecarboxylate (SMCC) or its sulfonated variant sulfo-SMCC, both reagents being available from Sigma-Aldrich.

An alternative conjugation technique employs copper-free "click chemistry," in which an azide group adds across the strained alkyne bond of a cyclooctyne to form an 1,2,3-triazole ring. See, e.g., Agard et al., *J. Amer. Chem. Soc.* 2004, 126, 15046; Best, *Biochemistry* 2009, 48, 6571, the disclosures of which are incorporated herein by reference. The azide can be located on the antibody and the cyclooctyne on the drug moiety, or vice-versa. A preferred cyclooctyne group is dibenzocyclooctyne (DIBO). Various reagents having a DIBO group are available from Invitrogen/Molecular Probes, Eugene, Oreg. The reaction below illustrates click chemistry conjugation for the instance in which the DIBO group is attached to the antibody (Ab):

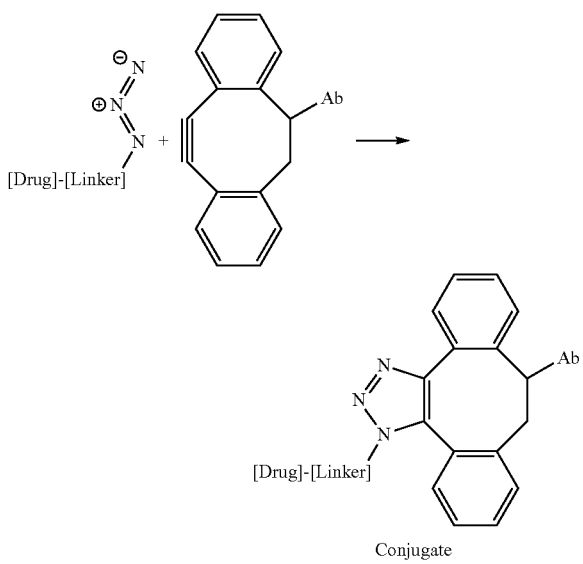

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenylalanine can be a conjugation site via the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., *Biotechnol. Bioeng.* 2009, 102 (2), 400-416. The foregoing disclosures are incorporated herein by reference. Thus, in one embodiment, an antibody that is used for making a conjugate with a dimer of this invention has one or more amino acids replaced by a non-natural amino acid, which preferably is p-acetylphenylalanine or p-azidophenylalanine, more preferably p-acetylphenylalanine.

Still another conjugation technique uses the enzyme transglutaminase (preferably bacterial transglutaminase or BTG), per Jeger et al., *Angew. Chem. Int. Ed.* 2010, 49, 9995 ("Jeger"). BTG forms an amide bond between the side chain carboxamide of a glutamine (the amine acceptor) and an alkyleneamino group (the amine donor), which can be, for example, the ε-amino group of a lysine or a 5-amino-n-pentyl group. In a typical conjugation reaction, the glutamine residue is located on the antibody, while the alkyleneamino group is located on the linker-drug moiety, as shown below:

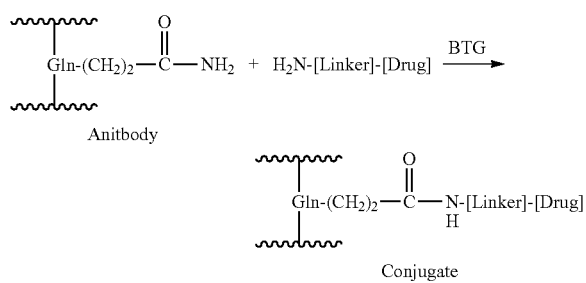

The positioning of a glutamine residue on a polypeptide chain has a large effect on its susceptibility to BTG mediated transamidation. None of the glutamine residues on an antibody are normally BTG substrates. However, Jeger discloses that if the antibody is deglycosylated—the glycosylation site being asparagine 297 (N297)—nearby glutamine 295 (Q295) is unblocked and rendered BTG-reactive. An antibody can be deglycosylated enzymatically by treatment with PNGase F (Peptide-N-Glycosidase F). Alternatively, an antibody can be synthesized glycoside free by introducing an N297A mutation in the constant region, to eliminate the N297 glycosylation site. Jeger discloses that an N297Q substitution in an antibody not only eliminates glycosylation, but also introduces a second glutamine residue (at position 297) that too is an amine acceptor. Thus, in one embodiment, an antibody that is conjugated to a dimer of this invention is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297). (Numbering of the amino acid positions in an antibody is per the EU index as set forth in Kabat et al., "Sequences of proteins of immunological interest, 5th ed., Pub. No. 91-3242, U.S. Dept. Health & Human Services, NIH, Bethesda, Md., 1991; hereinafter "Kabat").

Conjugation can also be effected using the enzyme Sortase A, as taught in Levary et al., *PLoS One* 2011, 6(4), e18342; Proft, *Biotechnol. Lett.* 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (III), or vice-versa.

An antibody also can be adapted for conjugation by modifying its glycosyl group to introduce a keto group that serves as a conjugation site by oxime formation, as taught by Zhu et al., *mAbs* 2014, 6, 1. In another glycoengineering variation, an antibody's glycosyl group can be modified to introduce an azide group for conjugation by "click chemistry." See Huang et al., *J. Am. Chem. Soc.* 2012, 134, 12308 and Wang, U.S. Pat. No. 8,900,826 B2 (2014) and U.S. Pat. No. 7,807,405 B2 (2010).

Yet another conjugation technique can be generally referred to as disulfide bridging: the disulfide bonds in an antibody are cleaved, creating a pair of thiol (—SH) groups. The antibody is then treated with a drug-linker compound that contains two thiol-reactive sites. Reaction of the thiol groups with the two sites effects a re-bridging that re-creates, in a fashion, the original disulfide bridge, thus preserving the antibody tertiary structure and attaching a drug-linker moiety. See, e.g., Burt et al., WO 2013/190292 A2 (2013) and Jackson et al., US 2013/0224228 A1 (2013).

Dimer-Linker Compounds

Generally, an ADC of a dimer of this invention comprises a linker attached to a functional group on the dimer, which linker is attached to the antibody. Reflecting the diversity of conjugation techniques available, the dimers of this invention can be elaborated into many different dimer-linker compounds suitable for conjugation to an antibody.

Generally, there are three different modes for attachment of the linker to a dimer of this invention, as illustrated in the figures below (with variables and optional substituents in the rings not shown for simplicity):

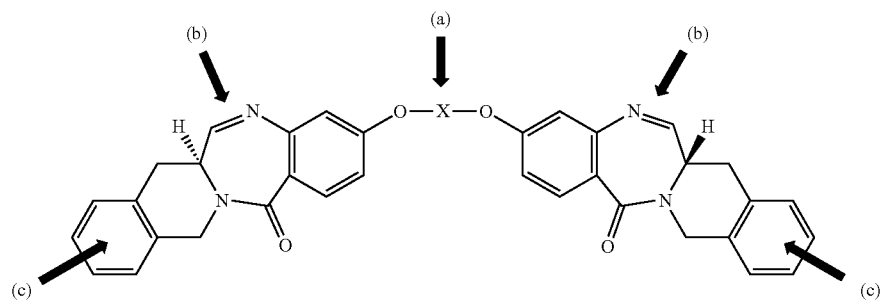

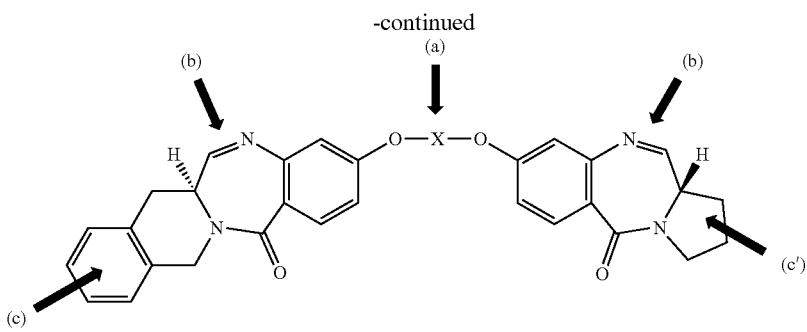

In type (a) dimer-linker compounds, a functional group for attachment of the linker is located in the bridge X between the two dimer halves. In type (b) dimer-linker compounds, the linker is attached as an addition product across an imine double bond. In types (c) and (c') dimer-linker compounds, a functional group for attachment of the linker is located at an "outside" ring of a THIQ, AZI, or PBD dimer unit.

In one embodiment, type (a) dimer-linker compound can be represented by the formula (IIIa):

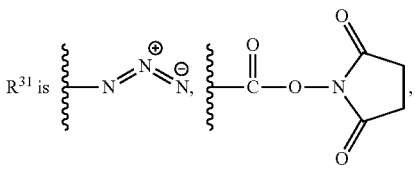

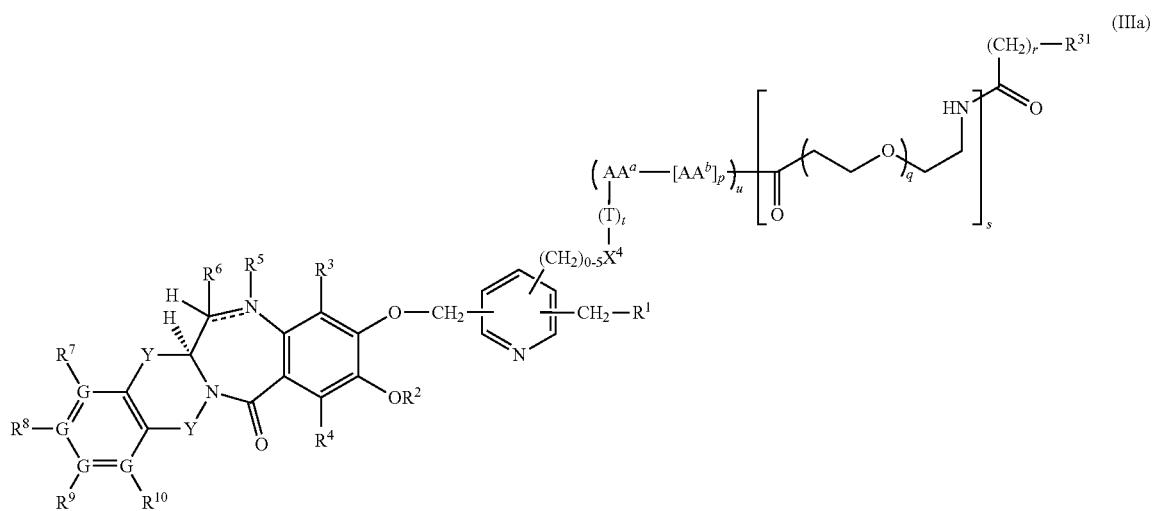

wherein

T is a self-immolating group;

t is 0 or 1;

$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

u is 0 or 1;

p is 1, 2, 3, or 4;

q is 1, 2, 3, 4, 5, 6, 7, 8, 9, 10, 11, or 12 (preferably 2, 3, 4, or 8);

r is 1, 2, 3, 4, or 5;

s is 0 or 1;

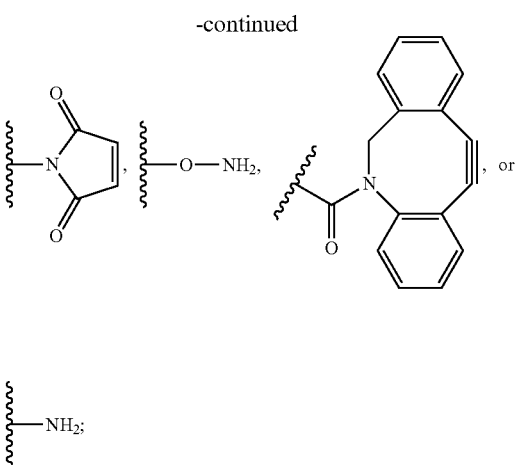

$X^4$ is S—S, O or NH; and $R^1$, $R^2$, $R^3$, $R^4$, $R^5$, $R^6$, $R^7$, $R^8$, $R^9$, $R^{10}$, G, Y, and the double line ===== are as defined in respect of formula (I) in the BRIEF SUMMARY OF THE INVENTION section hereinabove.

A preferred type (a) dimer-linker compound according to formula (IIIa) is represented by formula (IIIa'):

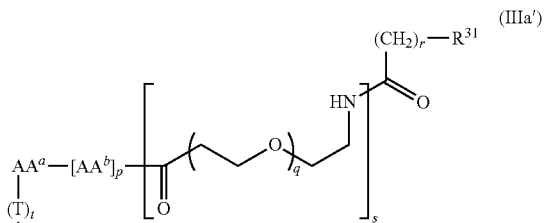
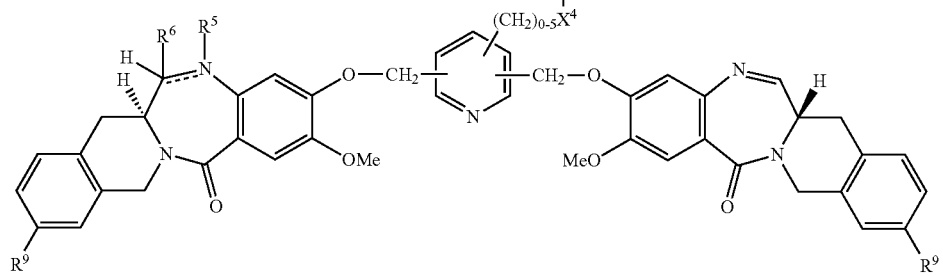

wherein $X^4$, T, t, $AA^a$, $AA^b$, p, q, r, s, and $R^{31}$ are as defined in respect of formula (IIIa);

each $R^9$ is independently H, $C_1$-$C_3$ alkyl, $O(CH_2CH_2O)_{1-4}H$, $(CH_2CH_2O)_{1-4}$($C1$-$C_3$ alkyl), OH, Cl, F, or Br;

$R^5$ is H if the double line ===== to the N to which it is bonded is a single bond and absent if the double line ===== is a double bond; and $R^6$ is H if the double line ===== to the C to which it is bonded is a single bond and absent if the double line ===== is a double bond.

Preferably, in formulae (IIIa) and (IIIa'), $R^9$ is H and $X^4$ is NH.

In one embodiment, type (b) dimer-linker compounds can be represented by formula (IIIb):

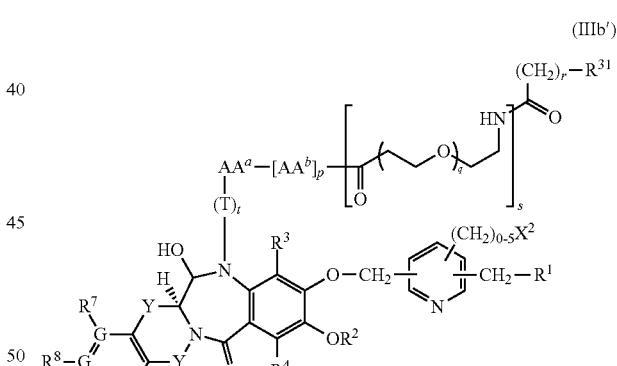

wherein

T, t, $AA^a$, $AA^b$, u, p, q, s, r, and $R^{31}$ are as defined of formula (IIIa); and X, $R^1$, $R^2$, $R^3$, $R^4$, $R^5$, $R^6$, $R^7$, $R^8$, $R^9$, $R^{10}$, $X^2$, Y and G are as defined in respect of formula (I) in the BRIEF SUMMARY OF THE INVENTION section hereinabove.

A preferred type (b) dimer-linker according to formula (IIIb) is represented by formula (IIIb')

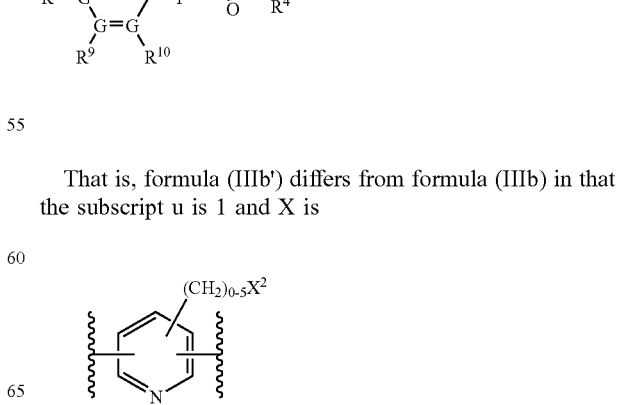

That is, formula (IIIb') differs from formula (IIIb) in that the subscript u is 1 and X is Another preferred type (b) dimer-linker according to formula (IIIb) is represented by formula (IIIb"):

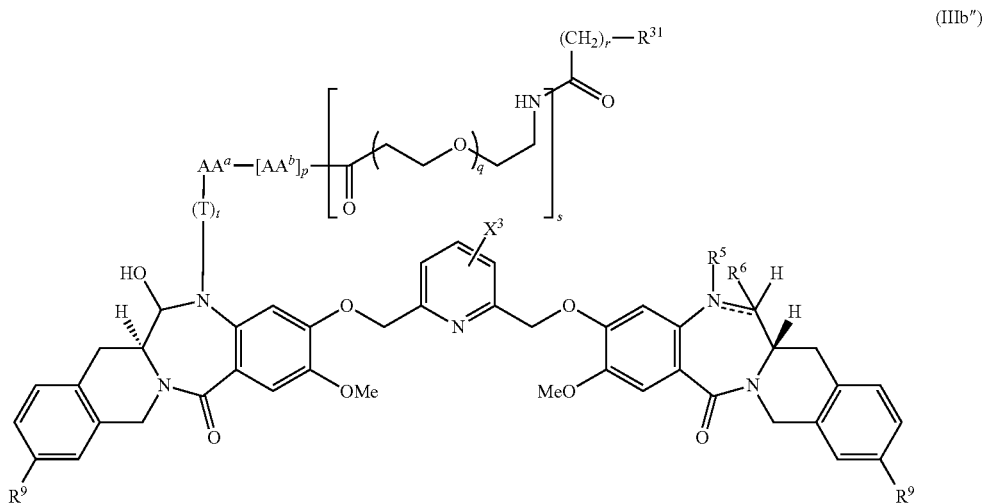

wherein
T, t, $AA^a$, $AA^b$, p, q, r, s, and $R^{31}$ are as defined in respect of formula (IIIa);
each $R^9$ is independently H, $C_1$-$C_3$ alkyl, $O(CH_2CH_2O)_{1-4}H$, $(CH_2CH_2O)_{1-4}(C1$-$C_3$ alkyl), OH, Cl, F, or Br;
$X^3$ is H, OH, OMe, Me, or $CH_2OH$;
$R^5$ is H if the double line ==== to the N to which it is bonded is a single bond and absent if the double line ==== is a double bond; and $R^6$ is H if the double line ==== to the C to which it is bonded is a single bond and absent if the double line ==== is a double bond.

Preferably, in formula (IIIb"), $R^9$ is H and $X^3$ is H.

Preferably, in formula (IIIb") the moiety

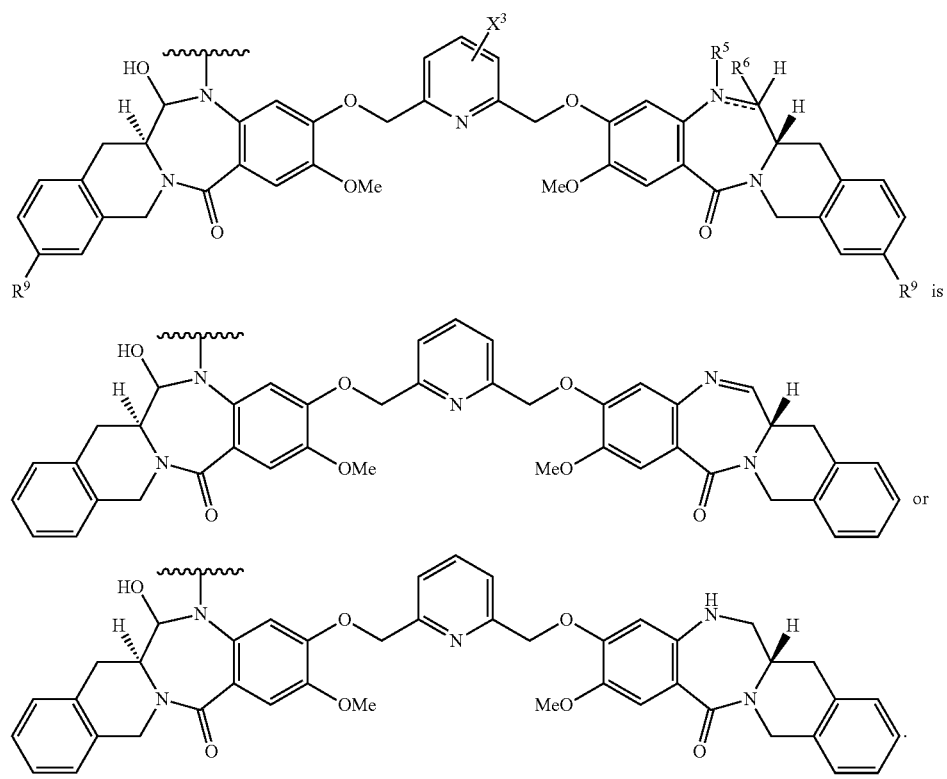

Examples of type (b) dimer-linker compounds include:
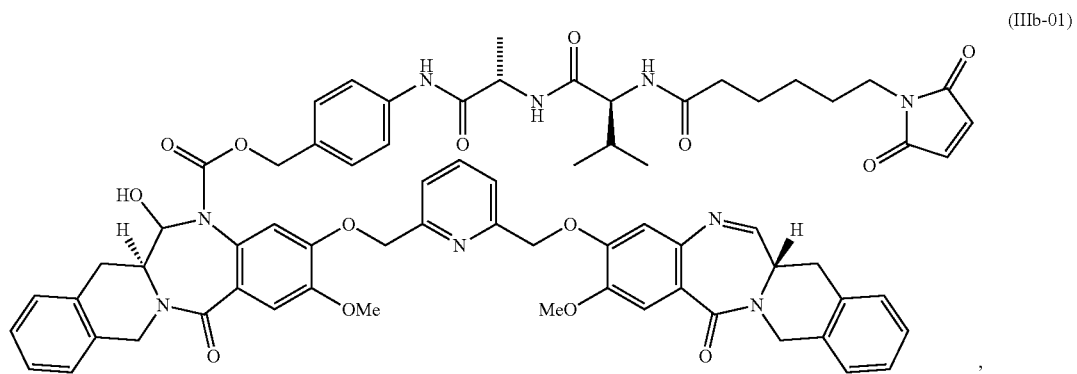
(IIIb-01)
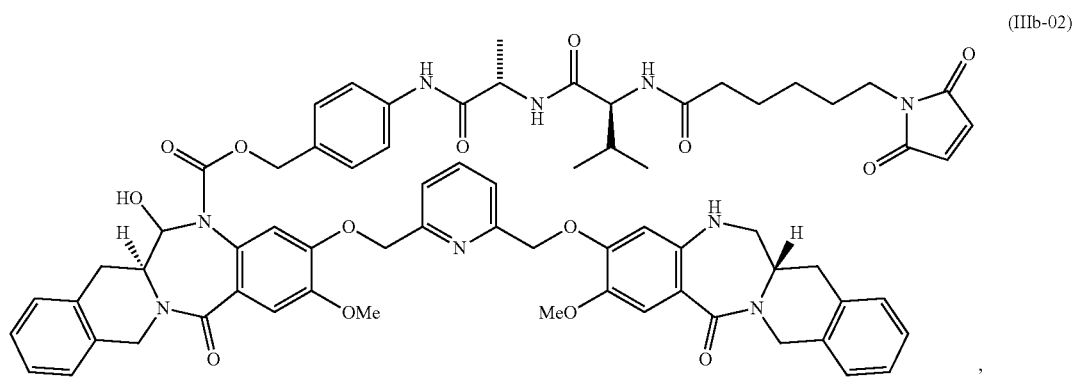
(IIIb-02)
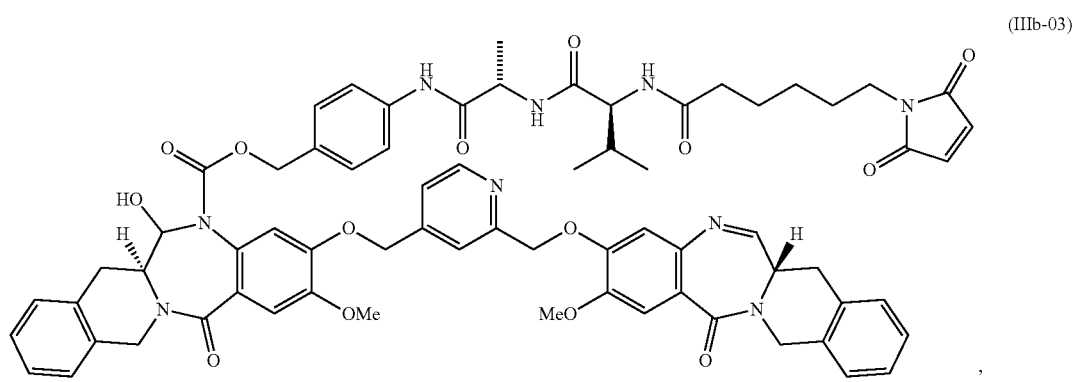
(IIIb-03)
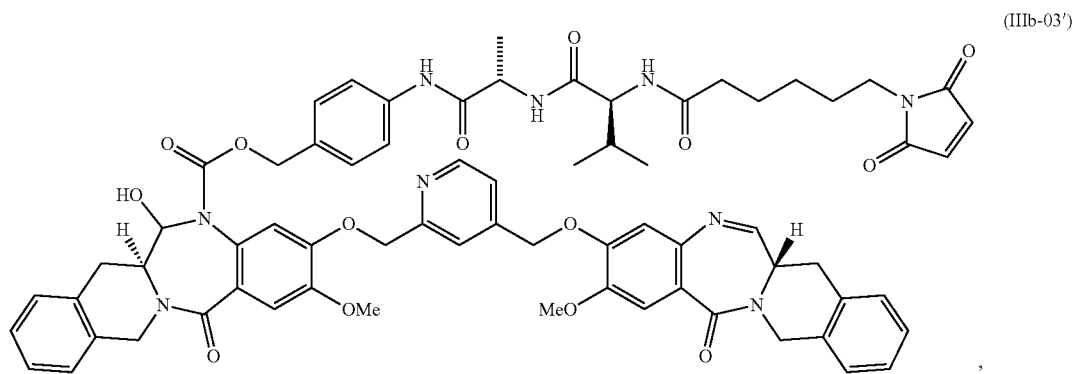
(IIIb-03′)

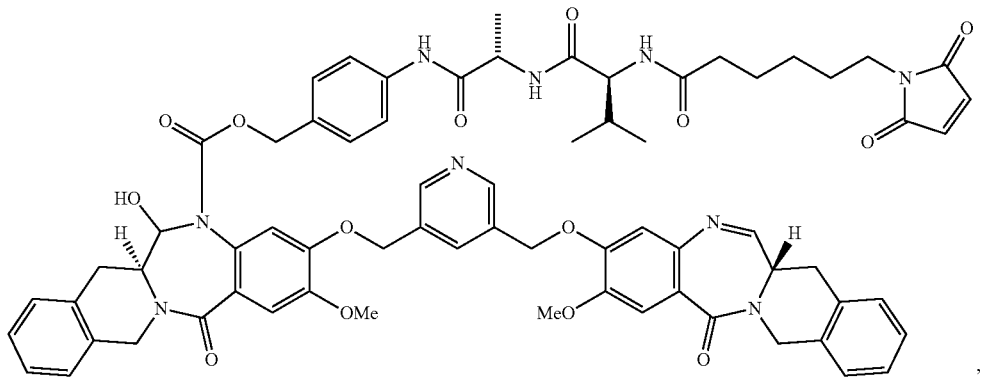
(IIIb-04)
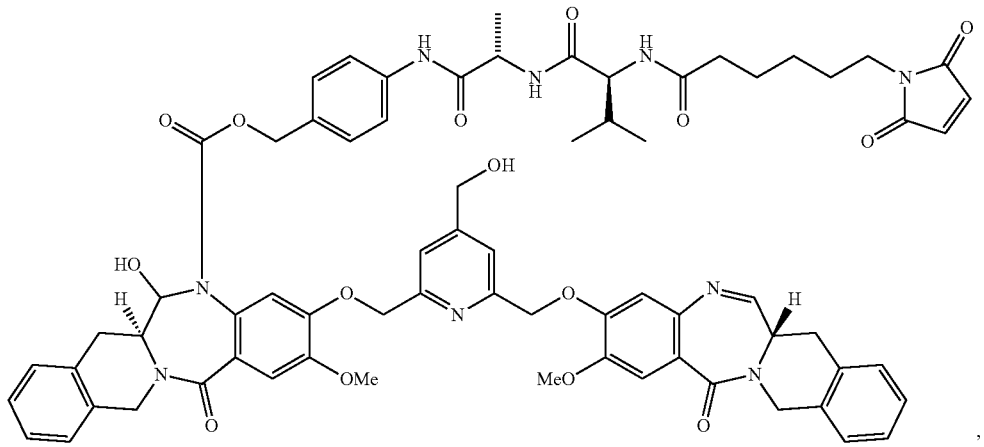
(IIIb-05)
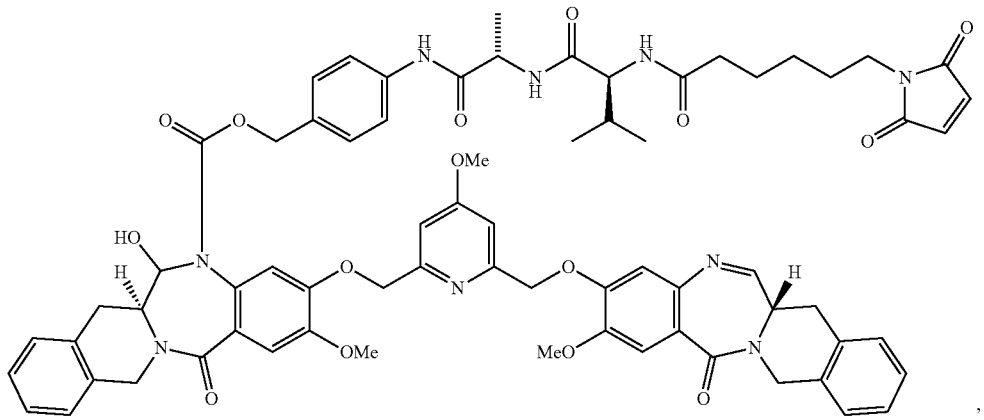
(IIIb-06)

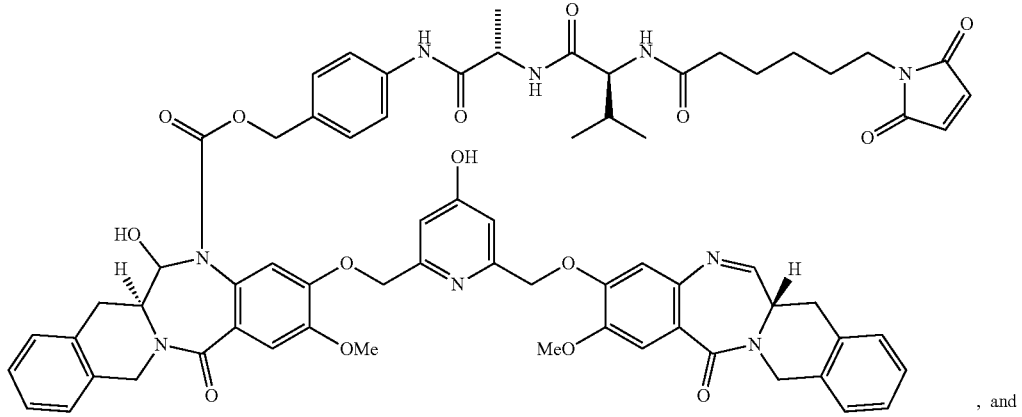
(IIIb-07), and
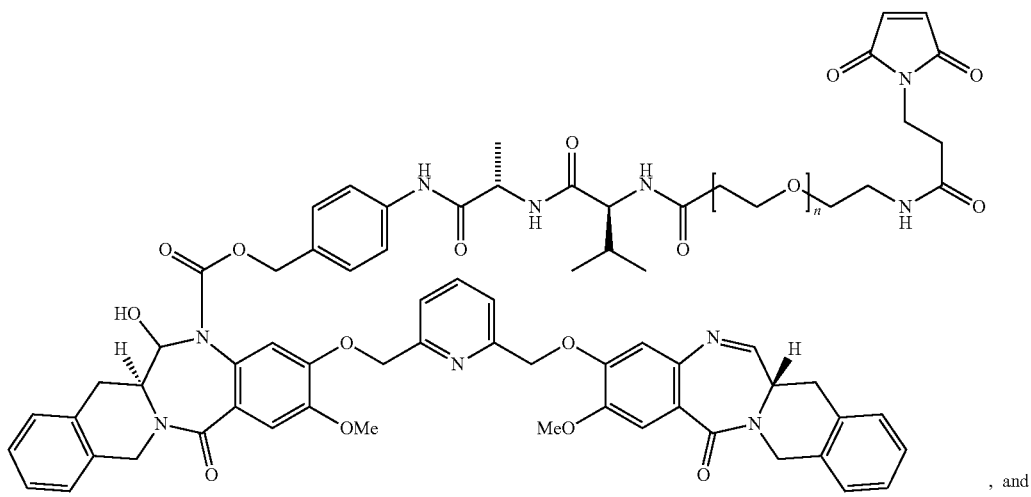
IIIb-08 n = 8   IIIb-08a n = 6
IIIb-08b n = 4   IIIb-08c n = 2
, and
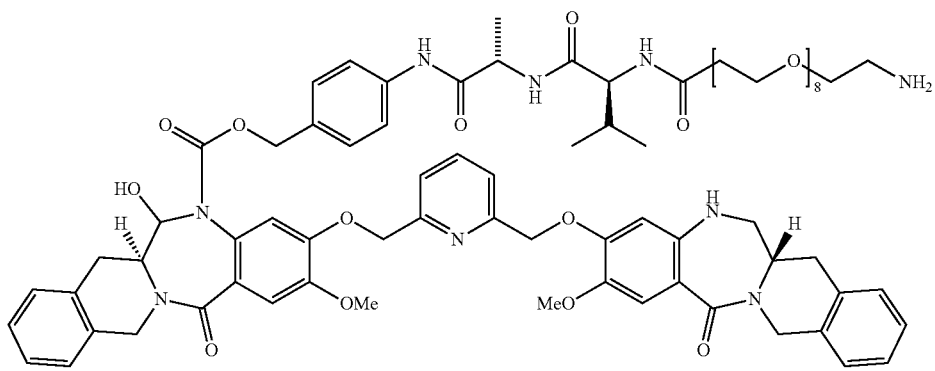
(IIIb-09)

In one embodiment, type (c) dimer-linker compounds can be represented by formula (IIIc):

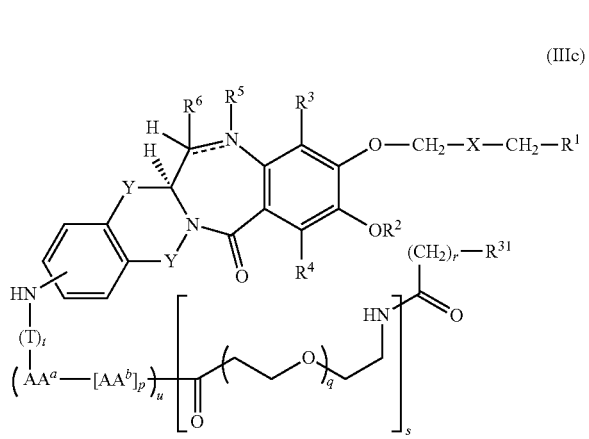
(IIIc)

wherein
T, t, $AA^a$, $AA^b$, u, p, q, s, r, and $R^{31}$ are as defined in respect of formula (IIIa); and
$R^1$, $R^2$, $R^3$, $R^4$, $R^5$, $R^6$, Y, $X^2$ and the double line ==== are as defined in respect of formula (I) the BRIEF SUMMARY OF THE INVENTION section hereinabove.

A preferred type (c) dimer-linker compound according to formula (IIIc) is represented by formula (IIIc'):

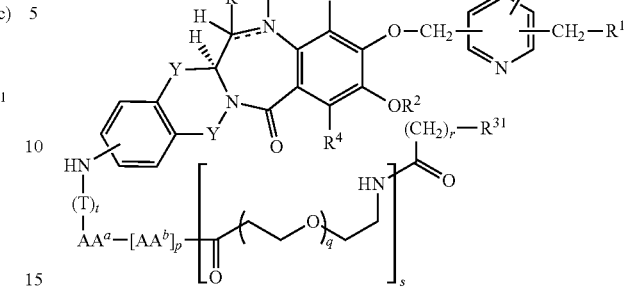
(IIIc')

That is, formula (IIIc') differs from formula (IIIc) in that subscript u is 1 and X is

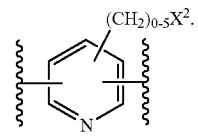

Another preferred type (c) dimer-linker compound according to formula (IIIc) is represented by formula (IIIc"):

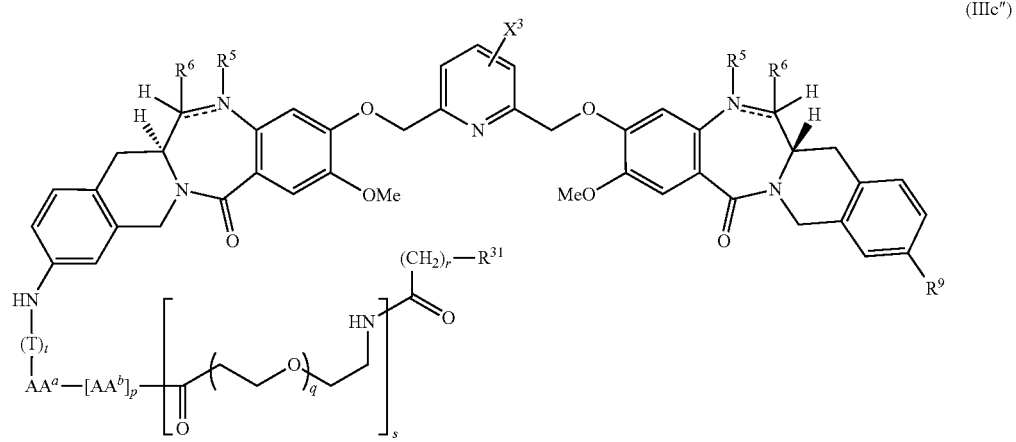
(IIIc")

wherein
$X^3$ is H, OH, OMe, Me, or $CH_2OH$;
at least one of the double lines ==== in a diazepine ring system is a double bond;

$R^5$ is H if the double line ==== to the N to which it is attached is a single bond and absent if the double line ==== is a double bond;

$R^6$ is H if the double line ==== to the C to which it is attached is a single bond and absent if the double line ==== is a double bond; and $R^9$ is H, $O(CH_2CH_2O)_{1-4}H$, $(CH_2CH_2O)_{1-4}(C1-C_3\ alkyl)$, OH, Cl, F, or Br.

Preferably, in formula (IIIc"), $R^9$ is H an $X^3$ is H.
Preferably, in formula (IIIc"), the moiety

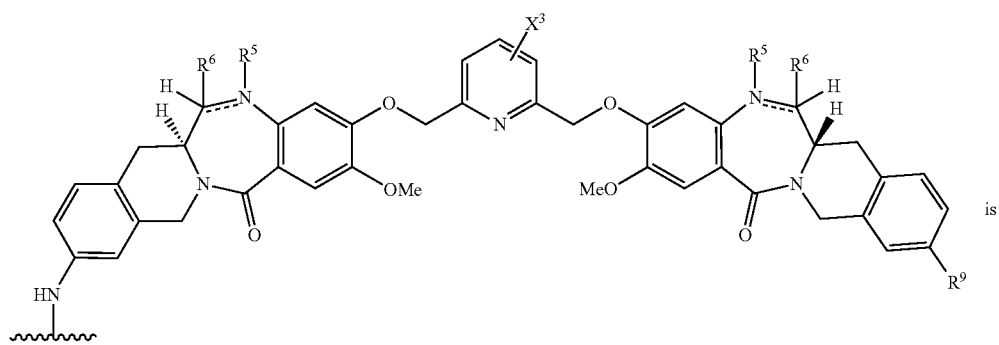
is
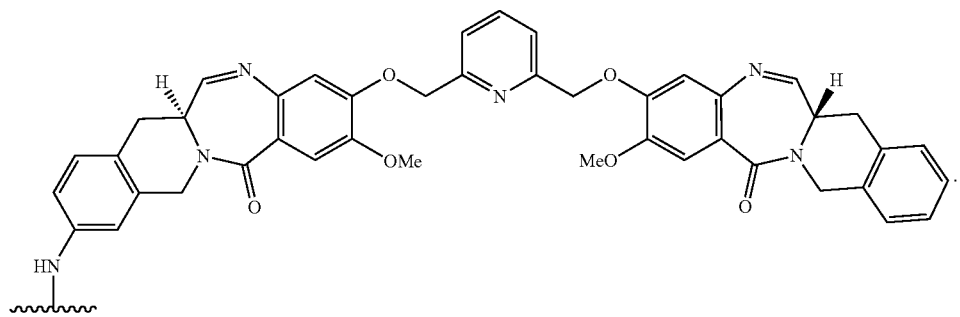
Examples of type (c) dimer-linker compounds include:
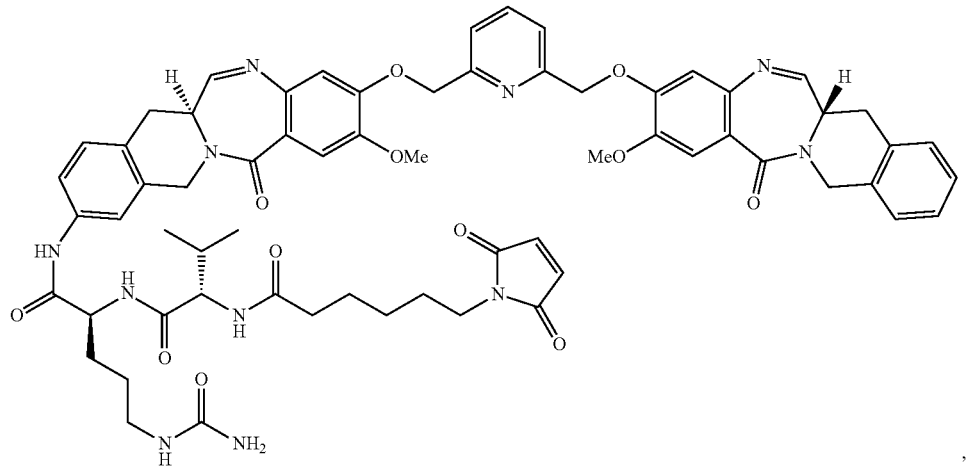
(IIIc-01)

-continued
(IIIc-02)
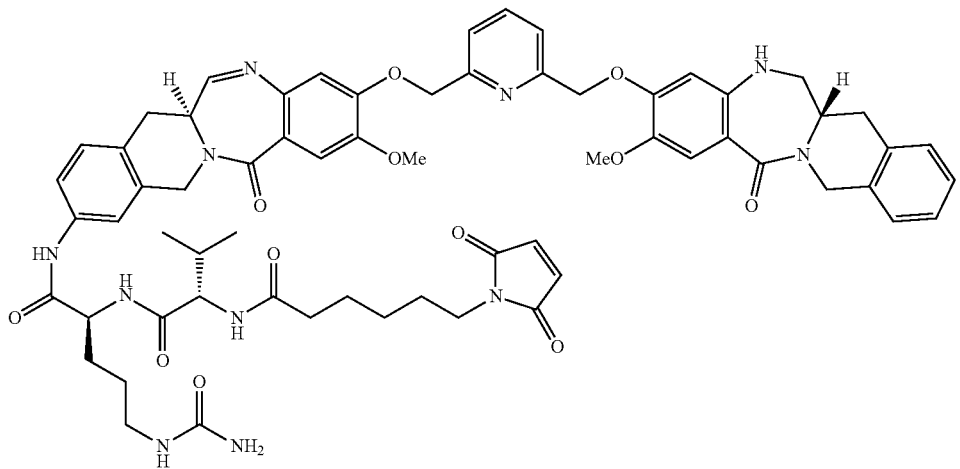
(IIIc-03)
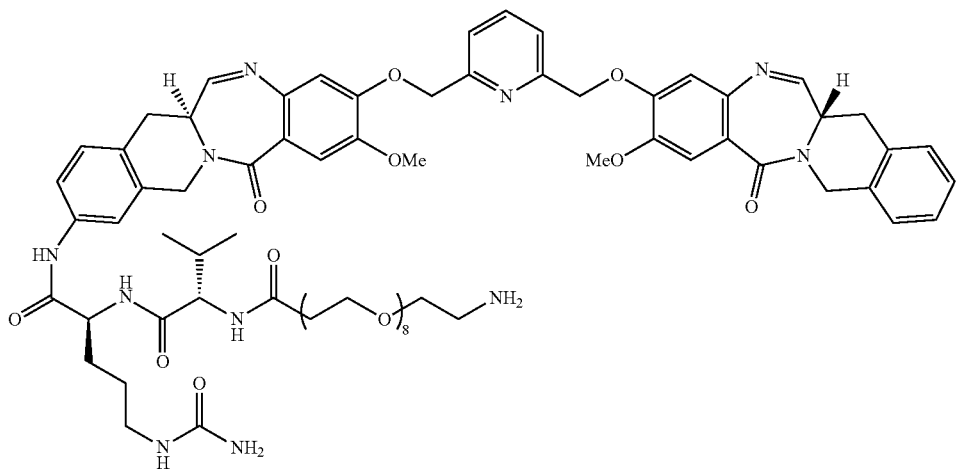
, and
(IIIc-04)
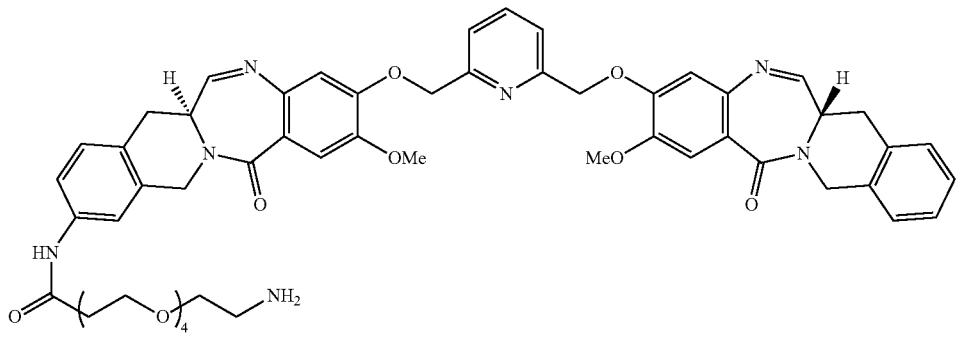

Type (c') dimer-linkers preferably are according to formula (IIIc'''):

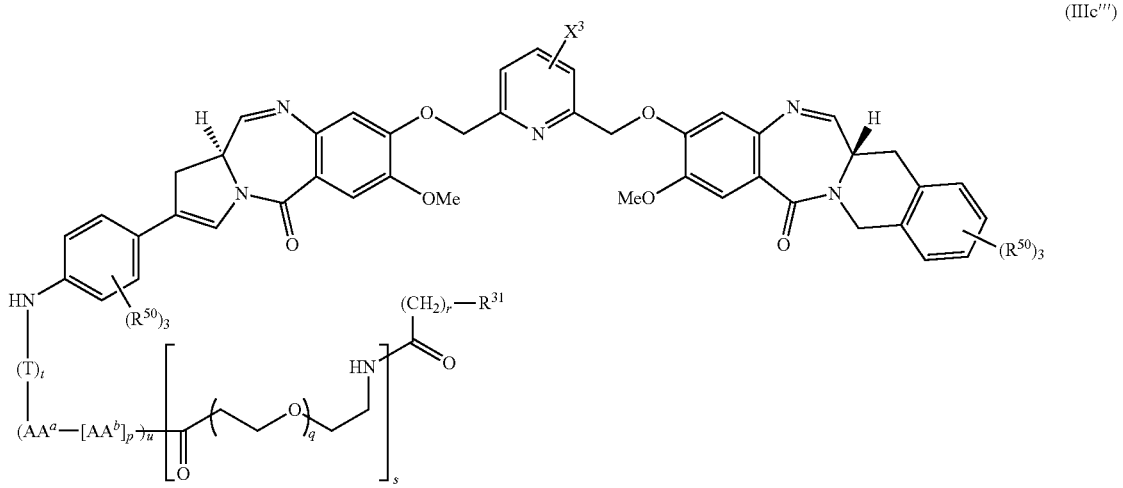

wherein
X³ is H, OH, OMe, Me, or CH₂OH;
T, t, AA$^a$, AA$^b$, u, p, q, s, r, and R$^{31}$ are as defined in respect of formula (IIIa); and
each R$^{50}$ is independently H, O(C₁-C₃ alkyl), O(C₂-C₃ alkylene), O(C₂-C₃ alkynyl), F, Cl, Br, or CN.

In formulae (IIIa), (IIIb), (IIIc) and (IIIc'''), where the subscripts t and u are both 0, the linker is of the non-cleavable type, as discussed hereinabove.

R$^{31}$ in formulae (IIIa), (IIIa'), (IIIa"), (IIIb), (IIIb'), (IIIb"), (IIIc), (IIIc'), (IIIc") and (IIIc''') is a reactive functional group capable of reacting with a complementary functional group on the antibody, to effect conjugation, as described above.

In a preferred embodiment, in formulae (IIIa), (IIIa'), (IIIb), (IIIb'), (IIIb"), (IIIc), (IIIc"), (IIIc') or (IIIc''') the group R$^{31}$ is

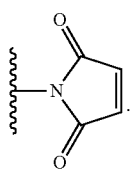

In another preferred embodiment, in formulae (IIIa), (IIIa'), (IIIa"), (IIIb), (IIIb'), (IIIb"), (IIIc), (IIIc') or (IIIc''') the group R$^{31}$ is

In formulae (IIIa), (IIIa'), (IIIa"), (IIIb), (IIIb'), (IIIb"), (IIIc), (IIIc'), (IIIc") and (IIIc'''), -AA$^a$-[AA$^b$]$_p$- represents a polypeptide whose length is determined by the value of p (dipeptide if p is 1, tetrapeptide if p is 3, etc.). AA$^a$ is at the carboxy terminus of the polypeptide and its carboxyl group forms a peptide (amide) bond with an amine nitrogen of the dimer (or self-immolating group T, if present). Conversely, the last AA$^b$ is at the amino terminus of the polypeptide and its α-amino group forms a peptide bond with

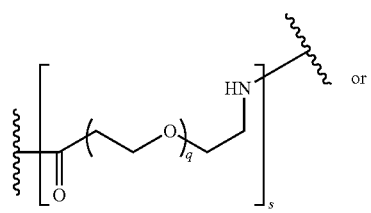

depending on whether s is 1 or 0, respectively. Preferred polypeptides -AA$^a$-[AA$^b$]$_p$- are Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit, written in the conventional N-to-C direction, as in H₂N-Val-Cit-CO₂H). More preferably, the polypeptide is Val-Cit, Val-Lys, or Val-Ala. Preferably, a polypeptide -AA$^a$-[AA$^b$]$_p$- is cleavable by an enzyme found inside the target (cancer) cell, for example a cathepsin and especially cathepsin B.

As indicated by the subscript t equals 0 or 1, a self-immolating group T is optionally present in dimer-linker compounds of formulae (IIIa), (IIIa'), (IIIa"), (IIIb), (IIIb'), (IIIb"), (IIIc), (IIIc') and (IIIc'''). When present, the self-immolating group T preferably is a p-aminobenzyl oxycarbonyl (PABC) group, whose structure is shown below, with an asterisk (*) denoting the end of the PABC bonded to an amine nitrogen of the dimer and a wavy line ( ~~~~ ) denoting the end bonded to the polypeptide -AA$^a$-[AA$^b$]$_p$-.

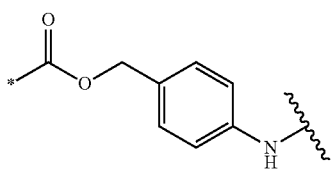

Preparation of Conjugates

This general procedure is based on introduction of free thiol groups into an antibody by reaction of lysine ε-amino groups with 2-iminothiolane, followed by reaction with a maleimide-containing drug-linker moiety, such as described above. Initially the antibody is buffer exchanged into 0.1 M phosphate buffer (pH 8.0) containing 50 mM NaCl and 2 mM diethylene triamine pentaacetic acid (DTPA) and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at RT (room temperature, circa 25° C.), the antibody is desalted into 50 mM HEPES, 5 mM Glycine, 2 mM DTPA, pH 5.5 using a SEPHADEX™ G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about two to three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM HEPES, 5 mM glycine, 2 mM DTPA, pH 5.5)). The thiolated material is maintained on ice while the number of thiols introduced is quantitated as described above.

After verification of the number of thiols introduced, the drug (dimer)-linker moiety is added at a 2.5-fold molar excess per thiol. The conjugation reaction is allowed to proceed in conjugation buffer containing a final concentration of 25% propylene glycol and 5% trehalose. Commonly, the drug-linker stock solution is dissolved in 100% DMSO. The stock solution is added directly to the thiolated antibody.

The conjugation reaction mixture is incubated at RT for 2 h with gentle stirring. A 10-fold molar excess of N-ethyl maleimide (100 mM Stock in DMSO) is then added to the conjugation mixture and stirred for an additional hour to block any unreacted thiols.

The sample is then filtered via a 0.2 μ filter The material is buffer exchanged via TFF VivaFlow 50 Sartorius 30 MWCO PES membrane into 10 mg/mL glycine, 20 mg/mL sorbitol, 15% acetonitrile pH 5.0 (5× TFF buffer exchange volume), to remove any unreacted drug. The final formulation is carried out by TFF into 20 mg/mL sorbitol, 10 mg/mL glycine, pH 5.0.

The following procedure can be used for transglutaminase mediated conjugation of dimer-linker compounds wherein the linker has an amine group that can act as an amine donor. The antibody can be one that has a transglutaminase-reactive glutamine, for example one with an N297A or N297Q substitution. Conjugation is carried out by recombinant bacterial transglutaminase with a molar ratio of antibody:enzyme of 5:1. The conjugation is carried out using standard protocols in 50 mM Tris buffer, pH 8.0, incubated overnight at 37° C. The resulting conjugate is purified on a Protein A column, pre-equilibriated with 50 mM Tris, pH 8.0. The conjugate is eluted with 0.1 M sodium citrate buffer, pH 3.5. The eluted fractions are neutralized with 1M Tris pH 9.0. The conjugated can be formulated in 20 mg/mL Sorbitol, 10 mg/mL Glycine, pH 5.0.

Those skilled in the art will understand that the above-described conditions and methodologies are exemplary and non-limiting and that other approaches for conjugation are known in the art and usable in the present invention.

Conjugates

In one embodiment, conjugates of this invention are derived from type (a) dimer-linker compounds and can be represented by the formula (IVa):

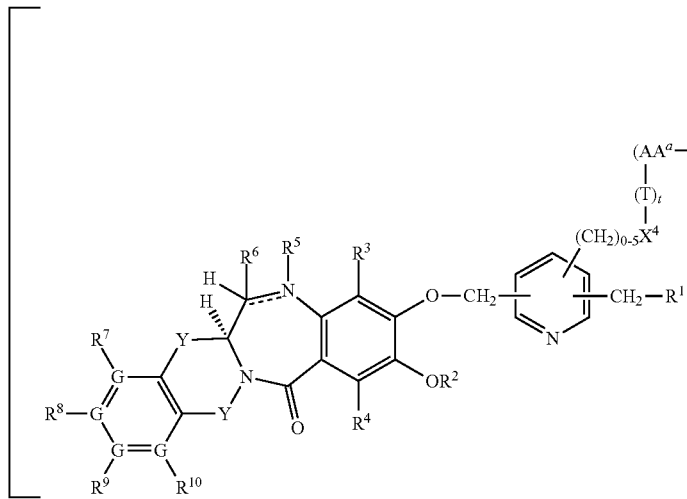
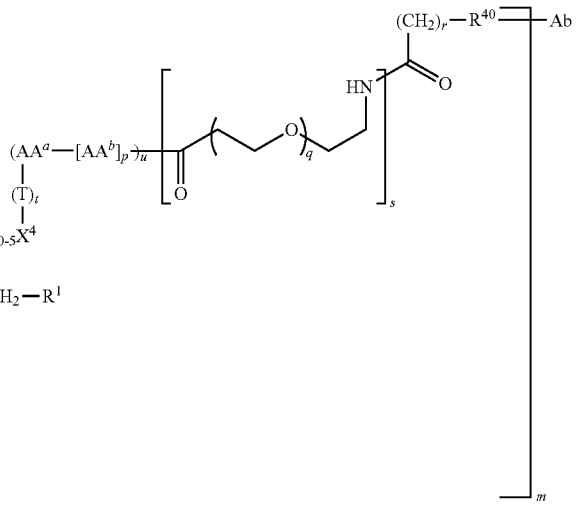

(IVa)

wherein
Ab is an antibody;
R40 is

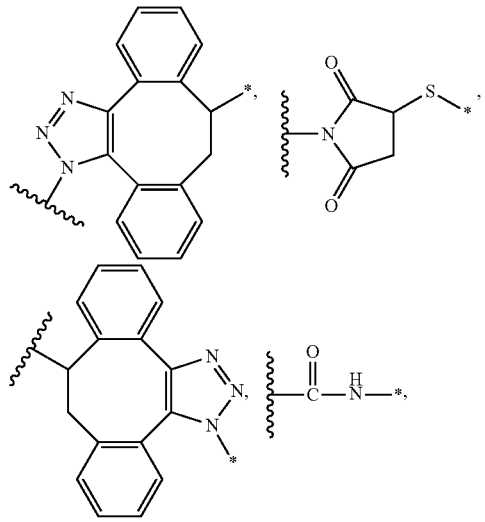

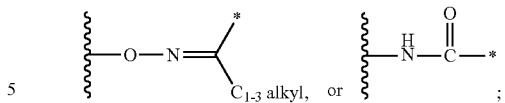

where the open valence of $R^{40}$ that is bonded to Ab is denoted by an asterisk (*) and the open valence of $R^{40}$ that is bonded to $(CH_2)_r$ is denoted by a wavy line ( ~~~~~ );

m is 1, 2, 3, or 4;

T, t, $AA^a$, $AA^b$, u, p, q, s, r, and $X^4$ are as defined in respect of formula (IIIa); and $R^1$, $R^2$, $R^3$, $R^4$, $R^5$, $R^6$, $R^7$, $R^8$, $R^9$, $R^{10}$, Y, G, and the double line ===== are as defined in respect of formula (I) in the BRIEF SUMMARY OF THE INVENTION section hereinabove.

A preferred conjugate according to formula (IVa) is represented by formula (IVa'):

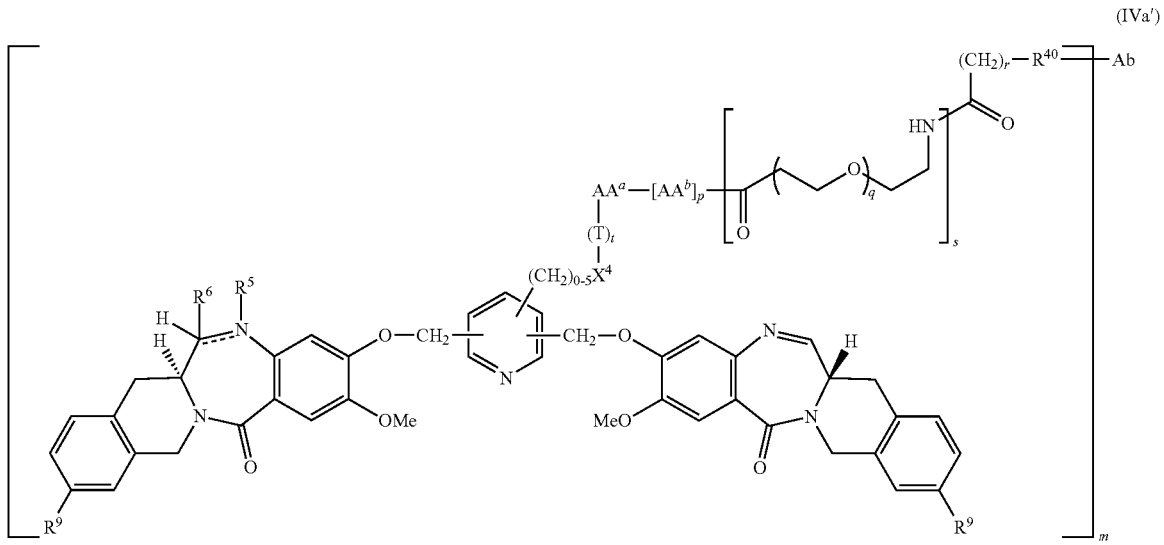

(IVa')

wherein
Ab, $R^{40}$, T, t, $AA^a$, $AA^b$, p, q, s, r, and $X^4$ are as defined in respect of formula (IIIa);
$R^5$ is H if the double line ===== to the N to which it is bonded is a single bond and absent if the double line ===== is a double bond;
$R^6$ is H if the double line ===== to the C to which it is bonded is a single bond and absent if the double line ===== is a double bond; and
$R^9$ is H, OH, OMe, $NH_2$, $NMe_2$, $C_1$-$C_3$ alkyl, $O(CH_2CH_2O)_{1-8}$Me, $OCH_2CH_2OH$, F, Cl, Br or

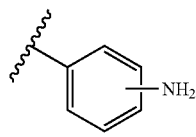

(especially the para- isomer).

In another embodiment, conjugates of this invention are derived from type (b) dimer-linker compounds and can be represented by the formula (IVb):

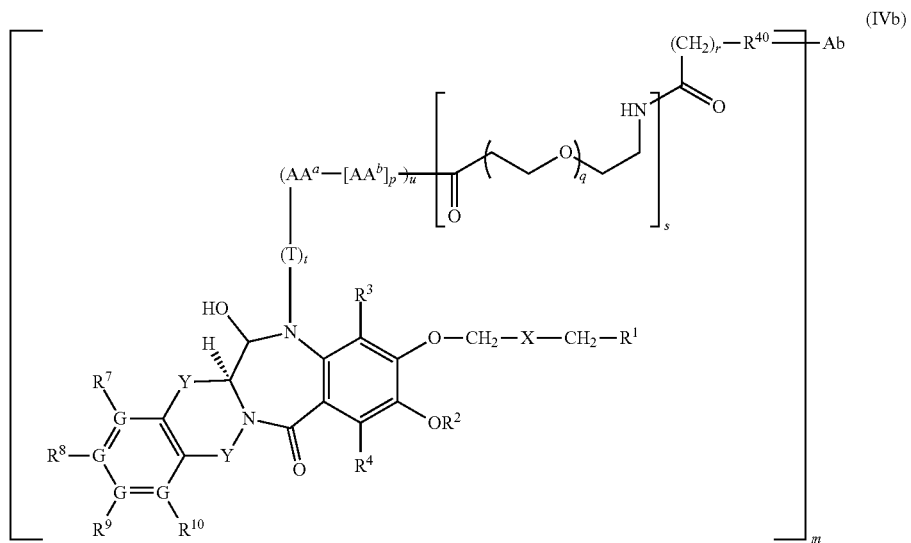

wherein
Ab, $R^{40}$, m, T, t, $AA^a$, $AA^b$, u, p, q, s, and r are as defined in respect of formula (IVa); and
$R^1$, $R^2$, $R^3$, $R^4$, $R^7$, $R^8$, $R^9$, $R^{10}$, Y, G, and X are as defined in the BRIEF SUMMARY OF THE INVENTION section hereinabove in respect of formula (I).

A preferred conjugate according to formula (IVb) is represented by formula (IVb'):

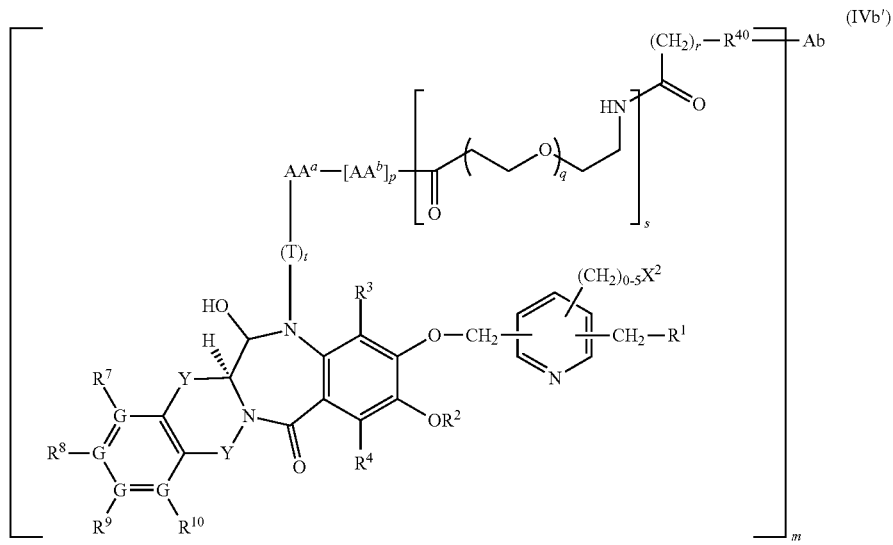

wherein
T, t, $AA^a$, $AA^b$, m, p, q, s, r, $R^{40}$, and Ab are as defined in respect of formula (IVa) and $R^1$, $R^2$, $R^3$, $R^4$, $R^7$, $R^8$, $R^9$, $R^{10}$, Y, G, and $X^2$ are as defined in respect of formula (IVa).

That is, conjugate (IVb') differs from conjugate (IVb) in that the subscript u is 1 and X is

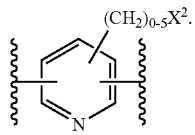

Another preferred conjugate according to formula (IVb) has a structure represented by formula (IVb"):

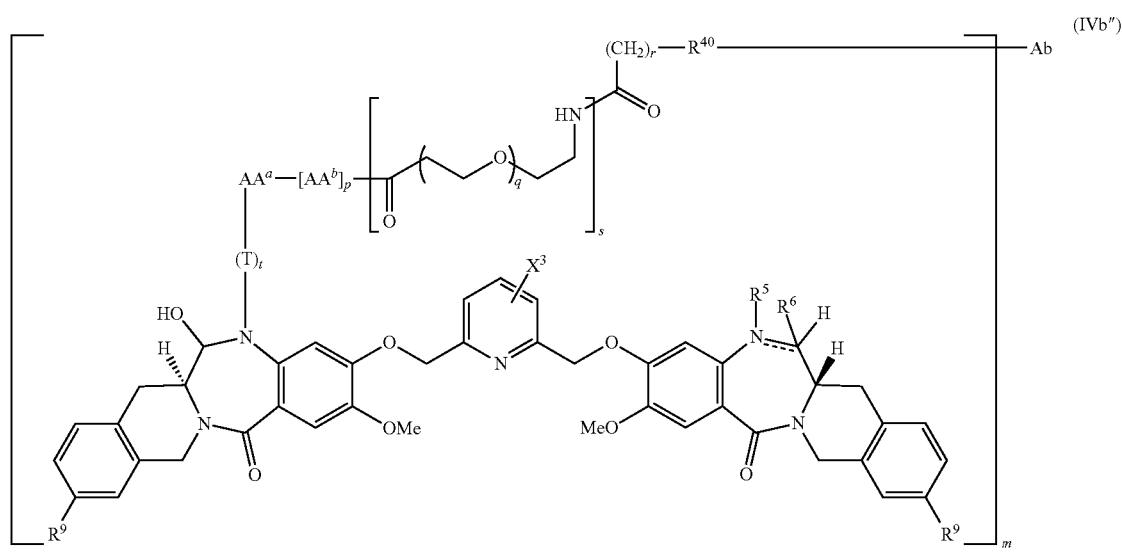

wherein

T, t, $AA^a$, $AA^b$, m, p, q, s, r, $R^{40}$, and Ab are as defined in respect of formula (IVa);

$X^3$ is H, OH, OMe, Me or $CH_2OH$;

$R^5$ is H if the double line ==== to the N to which it is bonded is a single bond and absent if the double line ==== is a double bond;

$R^6$ is H if the double line ==== to the C to which it is bonded is a single bond and absent if the double line ==== is a double bond; and $R^9$ is H, OH, OMe, $NH_2$, $NMe_2$, $C_1$-$C_3$ alkyl, $O(CH_2CH_2O)_{1-8}Me$, $OCH_2CH_2OH$, F, Br, Cl, or

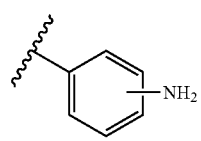

(especially the para- isomer).

Preferably, in formula (IVb'), $R^9$ is H and $X^3$ is H.

In another embodiment, conjugates of this invention are derived from type (c) dimer-linker compounds and can be represented by the formula (IVc):

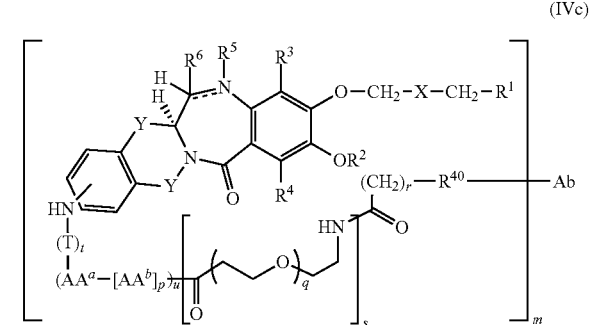

wherein

Ab, $R^{40}$, m, T, t, $AA^a$, $AA^b$, u, p, q, s, and r are as defined in respect of formula (IVa); and $R^1$, $R^2$, $R^3$, $R^4$, $R^5$, $R^6$, Y, X, and the double line ==== are as defined in the BRIEF SUMMARY OF THE INVENTION section hereinabove in respect of formula (I).

A preferred conjugate according to formula (IVc) is represented by formula (IVc'):

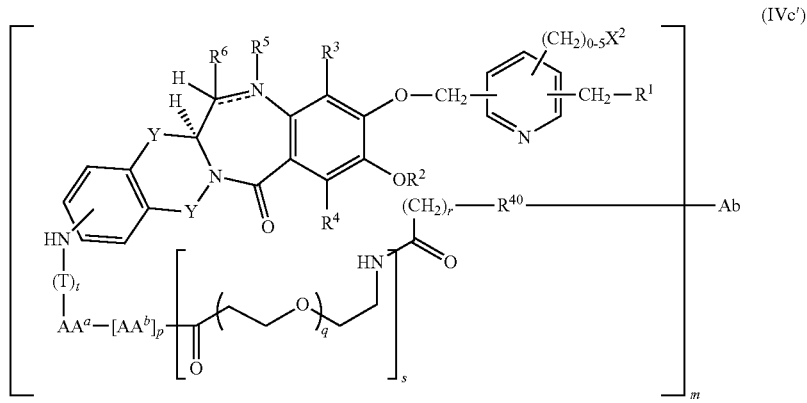

wherein
Ab, $R^{40}$, m, T, t, $AA^a$, $AA^b$, p, q, s, and r are as defined in respect of formula (IVa); and
$R^1$, $R^2$, $R^3$, $R^4$, $R^5$, $R^6$, Y, $X^2$, and the double line ==== are as defined in the BRIEF SUMMARY OF THE INVENTION section hereinabove in respect of formula (I).

That is, conjugate (IVc') differs from conjugate (IVc) in that the subscript u is 1 and X is

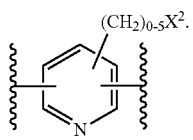

Another preferred conjugate according to formula (IVc) has a structure represented by formula (IVc"):

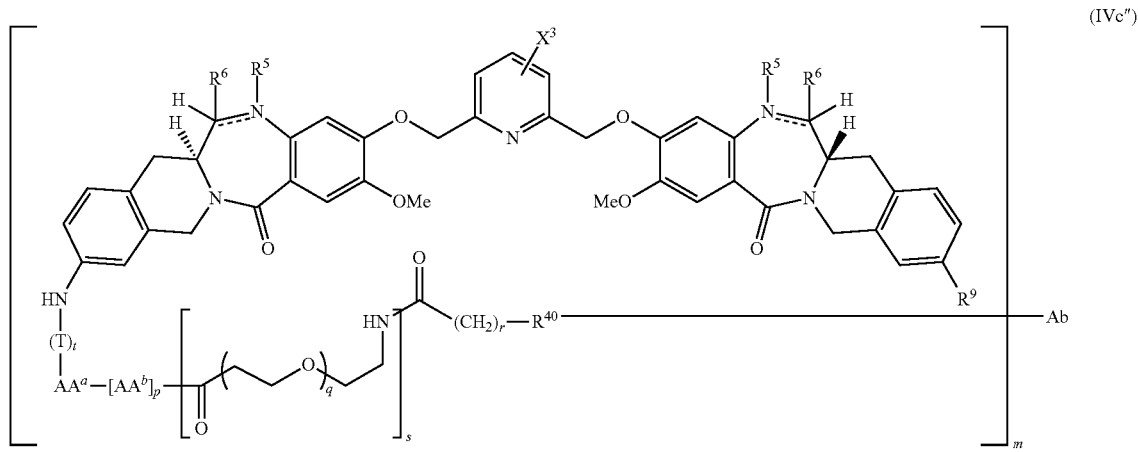

wherein

Ab, $R^{40}$, m, T, t, $AA^a$, $AA^b$, p, q, s, and r are as defined in respect of formula (IVa);

$X^3$ is H, OH, OMe, Me, or $CH_2OH$;

at least one of the double lines ==== in a diazepine ring system is a double bond;

$R^5$ is H if the double line ==== to the N to which it is attached is a single bond and absent if the double line ==== is a double bond;

$R^6$ is H if the double line ==== to the C to which it is attached is a single bond and absent if the double line ==== is a double bond; and $R^9$ is H, OH, OMe, $C_1$-$C_3$ alkyl, $O(CH_2CH_2O)_{1-8}Me$, F, Cl, or Br.

Preferably, in formula (IVc"), $R^9$ is H and $X^3$ is H.

Preferred conjugates based on type (c') dimer-linkers are according to formula (IVc'''):

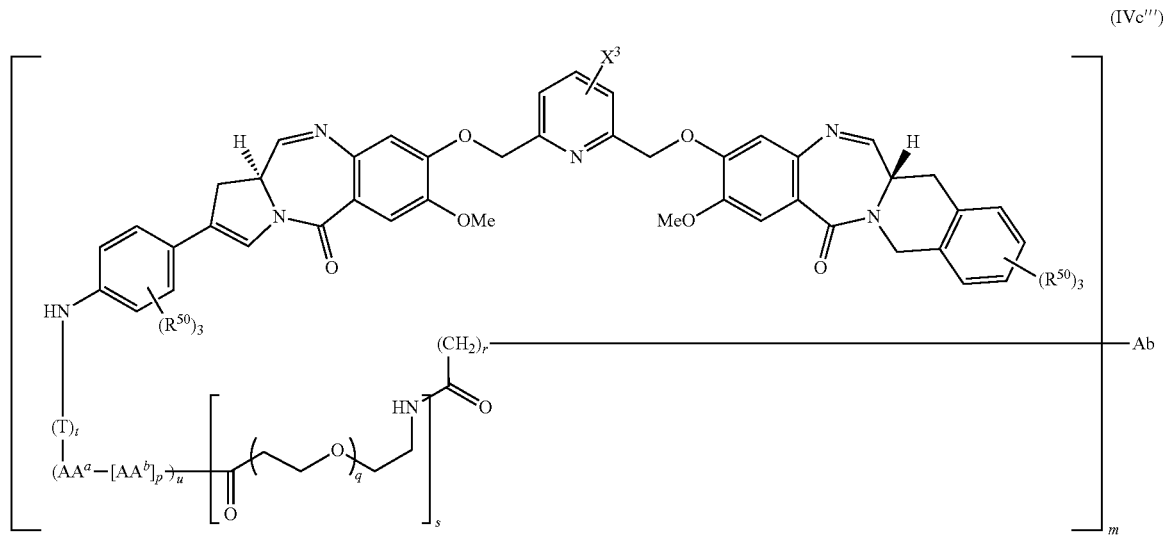

(IVc''')

wherein

Ab, $R^{40}$, m, T, t, $AA^a$, $AA^b$, p, q, s, u, and r are as defined in respect of formula (IVa);

$X^3$ is H, OH, OMe, Me, or $CH_2OH$; and each $R^{50}$ is independently H, $O(C_1$-$C_3$ alkyl), $O(C_2$-$C_3$ alkylene), $O(C_2$-$C_3$ alkynyl), F, Cl, Br, or CN.

The preferences stated hereinabove in respect of the dimer linkers of formulae (IIIa), (IIIa'), (IIIb), (IIIb'), (IIIb"), (IIIc), (IIIc'), (IIIc") and (IIIc''') for the polypeptide -$AA^a$-$[AA^b]_p$- and the self-immolating group T are also applicable to conjugates of formulae (IVa), (IVa'), (IVb), (IVb'), (IVc), (IVc') and (IVc''').

In formulae (IVa), (IVb), (IVc) and (IVc'''), if the subscripts t and u are both 0, then the linker is of the non-cleavable type and relies on degradation of the antibody Ab to release the drug. The polyethylene glycol component optionally may be present (i.e., s is 1) if its presence is beneficial, for example by increasing the solubility of the drug-linker compound during conjugation and does not interfere with the biological activity of the drug.

Pharmaceutical Compositions

In another aspect, the present disclosure provides a pharmaceutical composition comprising a compound of the present invention, or of a conjugate thereof, formulated together with a pharmaceutically acceptable carrier or excipient. It may optionally contain one or more additional pharmaceutically active ingredients, such as an antibody or another drug. The pharmaceutical compositions can be administered in a combination therapy with another therapeutic agent, especially another anti-cancer agent.

The pharmaceutical composition may comprise one or more excipients. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

Preferably, a pharmaceutical composition is suitable for intravenous, intra-muscular, subcutaneous, parenteral, spinal or epidermal administration (e.g., by injection or infusion). Depending on the route of administration, the active compound may be coated in a material to protect it from the action of acids and other natural conditions that may inactivate it. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, for example, intranasally, orally, vaginally, rectally, sublingually or topically.

Pharmaceutical compositions can be in the form of sterile aqueous solutions or dispersions. They can also be formulated in a microemulsion, liposome, or other ordered structure suitable to achieve high drug concentration. The compositions can also be provided in the form of lyophilates, for reconstitution in water prior to administration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide a therapeutic response. For example, a single bolus may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier.

The dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg, or alternatively 0.1 to 5 mg/kg. Exemplary treatment regimens are administration once per week, once every two weeks, once every three weeks, once every four weeks, once a month, once every 3 months, or once every three to 6 months. Preferred dosage regimens include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/mL and in some methods about 25-300 µg /mL.

A "therapeutically effective amount" of a compound of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal.

The pharmaceutical composition can be a controlled or sustained release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the pharmaceutical composition can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995) *Am. J. Physiol.* 1233:134; Schreier et al. (1994) *J. Biol. Chem.* 269:9090; Keinanen and Laukkanen (1994) *FEBS Lett.* 346:123; and Killion and Fidler (1994) *Immunomethods* 4:273.

Uses

Compounds of this invention or their conjugates can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer (SCLC and NSCLC); breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; leukemias such as acute promyelocytic leukemia (APL), acute myelogenous leukemia (AML), acute lymphoblastic leukemia (ALL), and chronic myelogenous leukemia (CML); neoplasms of the central nervous systems, particularly brain cancer; multiple myeloma (MM), lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be renal, lung, gastric, or ovarian cancer.

Compounds of this invention or their conjugates can be administered in combination with other therapeutic agents, including antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, □-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine.

EXAMPLES

The practice of this invention can be further understood by reference to the following examples, which are provided by way of illustration and not of limitation. The following general procedures are illustrative, with thoseskilled in the art understanding that alternative but equivalent methods can be used.

Some $^1$H-NMR spectra were run on Bruker 600, 500, or 400 MHz instruments and chemical shifts were reported in ppm (□) with reference to tetramethylsilane (□□=0.0). Generally, evaporations were carried out under reduced pressure.

These two LC/MS analysis methods are illustrative:

A Column: Waters BEH C18, 2.0×50 mm, 1.7-μm particles; Mobile Phase A: water with 0.05% TFA (trifluoroacetic acid); Mobile Phase B: acetonitrile with 0.05% TFA; [2-98% in 1.5 min, with a 3 min run time]; Temperature: 40° C.; Flow: 0.8 mL/min. and a UV detector set at 220 or 254 nm.

B Column: PhenomenexLuna, 2.0×30 mm, 3-μm particles; Mobile Phase A: 10% acetonitrile/90% water with 0.1% TFA; Mobile Phase B: 90% acetonitrile/10% water with 0.1% TFA; [0-100% in 2 min, with a 4 min run time]; Temperature: 40° C.; Flow: 1.0 mL/min. and a UV detector set at 220 or 254 nm.

Example 1

Intermediate Compound 6

This example and FIG. 1 relate to the synthesis of intermediate compound 6, which is used for the preparation of dimers of this invention.

4-(Benzyloxy)-5-methoxy-2-nitrobenzoyl chloride 1 was prepared from the corresponding methyl ester as follows: To a solution of methyl 4-(benzyloxy)-5-methoxy-2-nitrobenzoate (Harve Chem, 15 g, 47.3 mmol) in tetrahydrofuran (THF, 350 mL) was added a solution of aq. NaOH (56.7 mL, 142 mmol, 2.5M). The reaction was stirred at 50° C. for 5 h. The reaction was cooled to RT (RT) and then concentrated in vacuo to remove the THF. The remaining aqueous layer was acidified with aq. HCl (6 N) to pH 2. The resulting yellow precipitate was filtered, washed with water, and dried under vacuum to give 4-(benzyloxy)-5-methoxy-2-nitrobenzoic acid (14.32 g, 100% yield). LCMS (M+H)=304.08. $^1$H NMR (400 MHz, METHANOL-d$_4$) □ 7.60 (s, 1H), 7.53-7.45 (m, 2H), 7.45-7.31 (m, 3H), 7.29 (s, 1H), 5.23 (s, 2H), 3.98 (s, 3H).

To a solution of the above nitrobenzoic acid (3.5 g, 11.54 mmol) in THF (150 mL) was added dropwise oxalyl chloride (1.212 mL, 13.85 mmol), followed by N,N-dimethylformamide (DMF, 50 uL). The resulting solution was stirred at RT for 2 h before it was concentrated in vacuo to give acid chloride 1 as a yellow solid.

Acid chloride 1 was dissolved in THF (35 mL) and added dropwise to a solution of (S)-benzyl 1,2,3,4-tetrahydroisoquinoline-3-carboxylate p-toluenesulfonic acid salt 2 (Accela, 5.58 g, 12.70 mmol) and triethylamine (4.83 mL, 34.6 mmol) in THF (80 mL) at 0° C. The reaction mixture was stirred at RT for 4 h before quenching with water and concentrated to remove the THF. The resulting mixture was extracted with EtOAc (3×). The combined organic layers were washed with sat. aq. NaHCO$_3$ and then brine and dried over Na$_2$SO$_4$ and concentrated in vacuo. The crude product mixture was purified using ISCO silica gel chromatography (80 g column, gradient from 0% to 100% EtOAc/dichloromethane (DCM) in 15 minutes) to give ester 3 (6.25 g, 98% yield). LCMS (M+H)=553. $^1$H NMR (400 MHz, CHLOROFORM-d) □ 7.95-7.72 (m, 1H), 7.57-7.35 (m, 5H), 7.34-7.0 (m, 8H), 7.14-6.98 (m, 1H), 6.94-6.69 (m, 1H), 5.39-5.19 (m, 2H), 5.19-5.08 (m, 1H), 4.99 (q, J=12.4 Hz, 1H), 4.75 (d, J=17.4 Hz, 1H), 4.65-4.40 (m, 2H), 4.28 (d, J=15.6 Hz, 1H), 3.86 (br. s., 3H), 3.71 (s, 1H), 3.50-3.18 (m, 1H).

A suspension of ester 3 (6.25 g, 11.31 mmol), zinc (4.44 g, 67.9 mmol), and NH$_4$Cl (7.26 g, 136 mmol) in MeOH (50 mL) was heated at 50° C. for 16 h. The reaction was cooled to RT and diluted with MeOH. The resulting mixture was filtered through a pad of CELITE™, washing successively with EtOAc, DCM and MeOH. The filtrates were combined and concentrated in vacuo. The crude product mixture was purified using ISCO silica gel chromatography (120 g column, gradient from 0% to 100% EtOAc/DCM in 15 minutes) to give dione 4 (4.5 g, 96% yield). LCMS (M+H)=415. $^1$H NMR (400 MHz, CHLOROFORM-d) □ 7.49-7.40 (m, 4H), 7.32 (br. s., 6H), 6.45 (s, 1H), 5.19 (s, 2H), 5.13 (d, J=15.4 Hz, 1H), 4.47 (d, J=15.2 Hz, 1H), 4.21 (t, J=6.7 Hz, 1H), 3.93 (s, 3H), 3.52 (dd, J=15.4, 7.0 Hz, 1H), 3.02 (dd, J=15.4, 6.4 Hz, 1H).

A solution of dione 4 (4.5 g, 10.86 mmol) in DMF (54.3 ml) was cooled to 0° C. before NaH (60% dispersion in mineral oil, 0.54 g, 13.57 mmol) was added batchwise. The resulting mixture was stirred for 30 min before (2-(chloromethoxy)ethyl)trimethylsilane (SEM-Cl, 2.31 ml, 13.03 mmol) was added. The reaction was warmed to RT and stirred for 1 h before quenching with water. The resulting mixture was extracted with EtOAc (3×). The combined organic layers were dried over Na$_2$SO$_4$ and concentrated in vacuo. The crude product mixture was purified using ISCO silica gel chromatography (80 g column, gradient from 0% to 50% EtOAc/DCM in 15 min) to give SEM-dione 5 (4.60 g, 78% yield). LCMS (M+H)=545. $^1$H NMR (400 MHz, CHLOROFORM-d) □ 7.59-7.41 (m, 2H), 7.40-7.21 (m, 9H), 5.43 (d, J=9.9 Hz, 1H), 5.21 (s, 2H), 5.14 (d, J=15.2 Hz, 1H), 4.50 (d, J=9.7 Hz, 1H), 4.41 (d, J=15.2 Hz, 1H), 4.33-4.16 (m, 1H), 4.13 (d, J=7.3 Hz, 1H), 3.92 (s, 3H), 3.82-3.46 (m, 3H), 3.06-2.84 (m, 1H), 1.26 (t, J=7.2 Hz, 1H), 0.97 (ddd, J=9.9, 6.8, 2.6 Hz, 2H), 0.10-0.01 (m, 9H).

A suspension of SEM-dione 5 (4.68 g, 8.59 mmol) and Pd/C (10%, 0.457 g) in EtOH (10 mL) was stirred under a balloon of H2 at RT for 3 h. The reaction was filtered through a CELITE™ pad, washed with EtOH, and concentrated in vacuo. The crude product mixture was purified using ISCO silica gel chromatography (120 g column, gradient from 0% to 100% EtOAc/DCM in 15 min) to give compound 6 (3.23 g, 83% yield). LCMS (M+H)=455. $^1$H NMR (400 MHz, CHLOROFORM-d) □ 7.40-7.21 (m, 5H), 5.97 (s, 1H), 5.46 (d, J=9.7 Hz, 1H), 5.18 (d, J=15.4 Hz, 1H), 4.72 (d, J=9.7 Hz, 1H), 4.58-4.24 (m, 2H), 3.95 (s, 3H), 3.83-3.44 (m, 3H), 3.14-2.88 (m, 1H), 0.99 (t, J=8.0 Hz, 2H), 0.14 (s, 9H).

Example 2

Intermediate Compound 13

Figure 2:
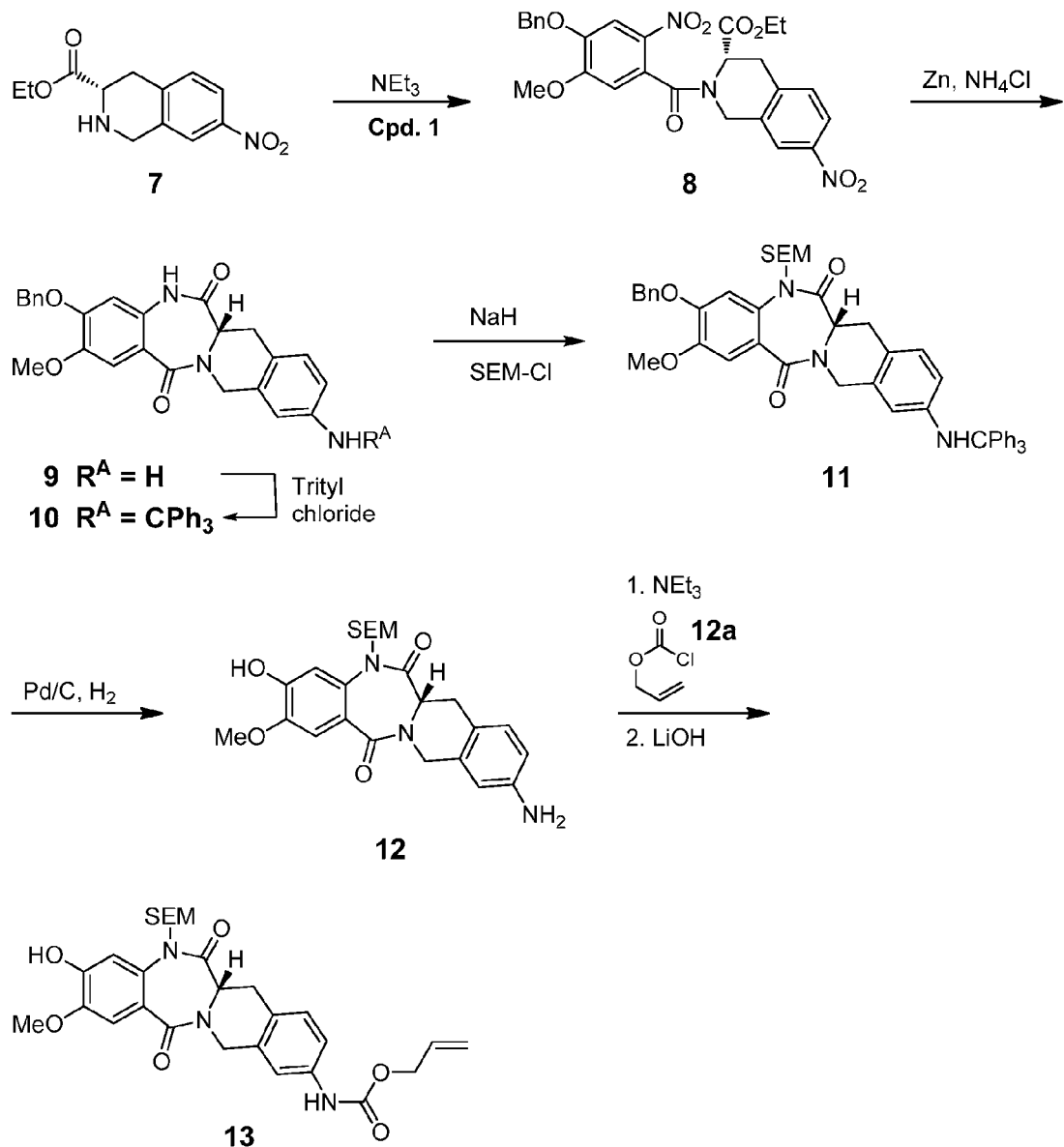

This example and FIG. 2 relate to the synthesis of further intermediate compounds useful in the preparation of dimers of this invention.

Acid chloride 1 was dissolved in THF (30 mL) and added dropwise to a solution of carboxylate 7 (Borzilleri et al., WO 2014/047024 A1 (2014), 1.6 g, 6.39 mmol) and NEt$_3$ (2.67 mL, 19.2 mmol) in THF (20 mL) at 0° C. The reaction solution was slowly warmed to RT and stirred for 30 min. The reaction was quenched with water and concentrated to remove THF. The resulting mixture was extracted with EtOAc (3×). The combined organic layers were washed with sat. aq. NaHCO$_3$, then brine, and dried over Na$_2$SO$_4$ and concentrated in vacuo. The crude product mixture was purified using ISCO silica gel chromatography (80 g column, gradient from 0% to 100% EtOAc/Hexane in 15 min) to give ethyl ester 8 (2.66 g, 78% yield). LCMS (M+H) =536.4.

A suspension of ethyl ester 8 (1.75 g, 3.55 mmol), zinc (1.394 g, 21.32 mmol), and NH$_4$Cl (2.281 g, 42.6 mmol) in MeOH (10 mL) was heated at 50° C. overnight. The reaction mixture was filtered through a pad of CELITE™, washing with copious amount of 20% MeOH in DCM. The filtrate was concentrated to give amino-dione 9 as a white solid (1.25 g, 2.90 mmol, 82% yield). LCMS (M+H)=430.3. $^1$H NMR (400 MHz, DMSO-d$_6$) ☐ 10.26 (br. s., 1H), 7.53-7.31 (m, 6H), 7.24 (s, 1H), 6.92 (d, J=7.9 Hz, 1H), 6.78 (s, 1H), 6.50-6.41 (m, 2H), 5.07 (d, J=4.6 Hz, 2H), 5.00-4.88 (m, 2H), 4.84 (d, J=15.0 Hz, 1H), 4.09 (d, J=15.0 Hz, 1H), 4.01 (t, J=6.9 Hz, 1H), 3.75 (s, 3H), 3.12 (dd, J=15.3, 7.6 Hz, 1H), 2.78 (dd, J=15.2, 6.2 Hz, 1H).

To a solution of amino-dione 9 (1.6 g, 3.73 mmol) and trityl chloride (1.246 g, 4.47 mmol) in DCM (10 mL) was added NEt$_3$ (0.779 mL, 5.59 mmol). The reaction mixture was stirred at RT for 3 h and concentrated. The crude product mixture was purified using ISCO silica gel chromatography (80 g column, 0-50% EtOAc/Hexane) to give trityl-dione 10 as a white solid (2.2 g, 3.27 mmol, 88% yield). $^1$H NMR (400 MHz, CHLOROFORM-d) ☐ 8.01 (s, 1H), 7.50-7.12 (m, 22H), 6.77 (d, J=8.4 Hz, 1H), 6.47-6.34 (m, 2H), 6.16 (dd, J=8.1, 2.4 Hz, 1H), 5.02 (br. s., 1H), 4.91 (d, J=15.2 Hz, 1H), 4.18-4.09 (m, 2H), 4.05 (t, J=6.9 Hz, 1H), 3.92 (s, 3H), 3.28 (dd, J=15.4, 7.7 Hz, 1H), 2.75 (dd, J=15.4, 6.4 Hz, 1H).

To a solution of trityl-dione 10 (2.2 g, 3.27 mmol) in DMF (15 mL) at 0° C. was added NaH (60% dispersion in mineral oil, 0.236 g, 3.93 mmol). The mixture was stirred for 30 min before SEM-Cl (0.697 ml, 3.93 mmol) was added. The reaction mixture was stirred at 0° C. for 2 h before it was quenched with brine. The reaction mixture was extracted with EtOAc (3×). The combined organic layers were dried over Na$_2$SO$_4$ and concentrated in vacuo. The crude product mixture was purified using ISCO silica gel chromatography (40 g column, 0-50% EtOAc/Hexane) to give SEM-dione 11 (2.1 g, 2.62 mmol, 80% yield). LCMS (M-trityl)=560.4. $^1$H NMR (400 MHz, CHLOROFORM-d) ☐ 7.48-7.42 (m, 2H), 7.41-7.32 (m, 9H), 7.31-7.18 (m, 11H), 6.77 (d, J=8.1 Hz, 1H), 6.38 (d, J=2.2 Hz, 1H), 6.19 (dd, J=8.3, 2.3 Hz, 1H), 5.45 (d, J=9.7 Hz, 1H), 5.21 (s, 2H), 5.08-4.92 (m, 2H), 4.49 (d, J=9.7 Hz, 1H), 4.13-4.08 (m, 1H), 4.02 (d, J=15.2 Hz, 1H), 3.93 (s, 3H), 3.71 (td, J=9.6, 7.0 Hz, 1H), 3.61 (td, J=9.6, 7.2 Hz, 1H), 3.36 (dd, J=15.5, 8.3 Hz, 1H), 2.72 (dd, J=15.5, 6.5 Hz, 1H), 1.05-0.92 (m, 2H), 0.06 (s, 9H).

A suspension of SEM-dione 11 (950mg, 1.18 mmol) and Pd/C (10%, 200 mg) in EtOAc (20 mL) was stirred under a balloon of H2 for 2 days. The reaction mixture was filtered through a pad of CELITE™ and washed with EtOAc and then MeOH. The combined filtrates were concentrated and purified using ISCO silica gel chromatography (40 g column, 0-100% EtOAc/Hexane) to give compound 12 (510 mg, 1.08 mmol, 90% yield). LCMS (M+H)=470.2. $^1$H NMR (400 MHz, CHLOROFORM-d) ☐ 7.33 (s, 1H), 7.27 (s, 1H), 7.09 (d, J=8.6 Hz, 1H), 6.67-6.54 (m, 2H), 6.02 (s, 1H), 5.47 (d, J=9.7 Hz, 1H), 5.11 (d, J=15.2 Hz, 1H), 4.71 (d, J=9.7 Hz, 1H), 4.29 (d, J=15.2 Hz, 1H), 4.22 (dd, 6.5 Hz, 1H), 3.94 (s, 3H), 3.79-3.60 (m, 4H), 3.47 (dd, J=15.4, 7.7 Hz, 1H), 2.90 (dd, J=15.5, 6.4 Hz, 1H), 1.09-0.94 (m, 2H), 0.05 (s, 9H).

To a solution of compound 12 (500 mg, 1.065 mmol) in THF (3 mL) at 0° C. was added NEt$_3$ (0.742 mL, 5.32 mmol). Allyl chloroformate 12a (513 mg, 4.26 mmol) was added dropwise. The resulting solution was stirred at 0° C. for 2 h and diluted with MeOH (5 mL) and aq. LiOH (2 mL, 2N). The resulting mixture was stirred at RT for 16 h. The reaction was diluted with EtOAC and washed with brine. The organic layer was separated, dried over Na$_2$SO$_4$, and concentrated in vacuo. The crude product was purified by ISCO silica gel chromatography (24 g column, 0-10% MeOH/DCM) to give compound 13 as a white solid (440 mg, 0.795 mmol, 74.6% yield). LCMS (M+H)=554.2. $^1$H NMR (400 MHz, CHLOROFORM-d) ☐ 7.38-7.30 (m, 3H), 7.27-7.21 (m, 2H), 6.96 (s, 1H), 6.28 (s, 1H), 6.02-5.89 (m, 1H), 5.44 (d, J=9.8 Hz, 1H), 5.35 (dq, J=17.2, 1.5 Hz, 1H), 5.26 (dq, J=10.4, 1.3 Hz, 1H), 5.10 (d, J=15.4 Hz, 1H), 4.70 (d, J=9.8 Hz, 1H), 4.66 (d, J=5.1 Hz, 2H), 4.40 (d, J=15.4 Hz, 1H), 4.31-4.23 (m, 1H), 3.91 (s, 3H), 3.79-3.58 (m, 2H), 3.51 (dd, J=15.6, 7.3 Hz, 1H), 2.96 (dd, J=15.5, 6.4 Hz, 1H), 1.07-0.95 (m, 2H), 0.03 (s, 9H).

Example 3

More Intermediates

Figure 3:
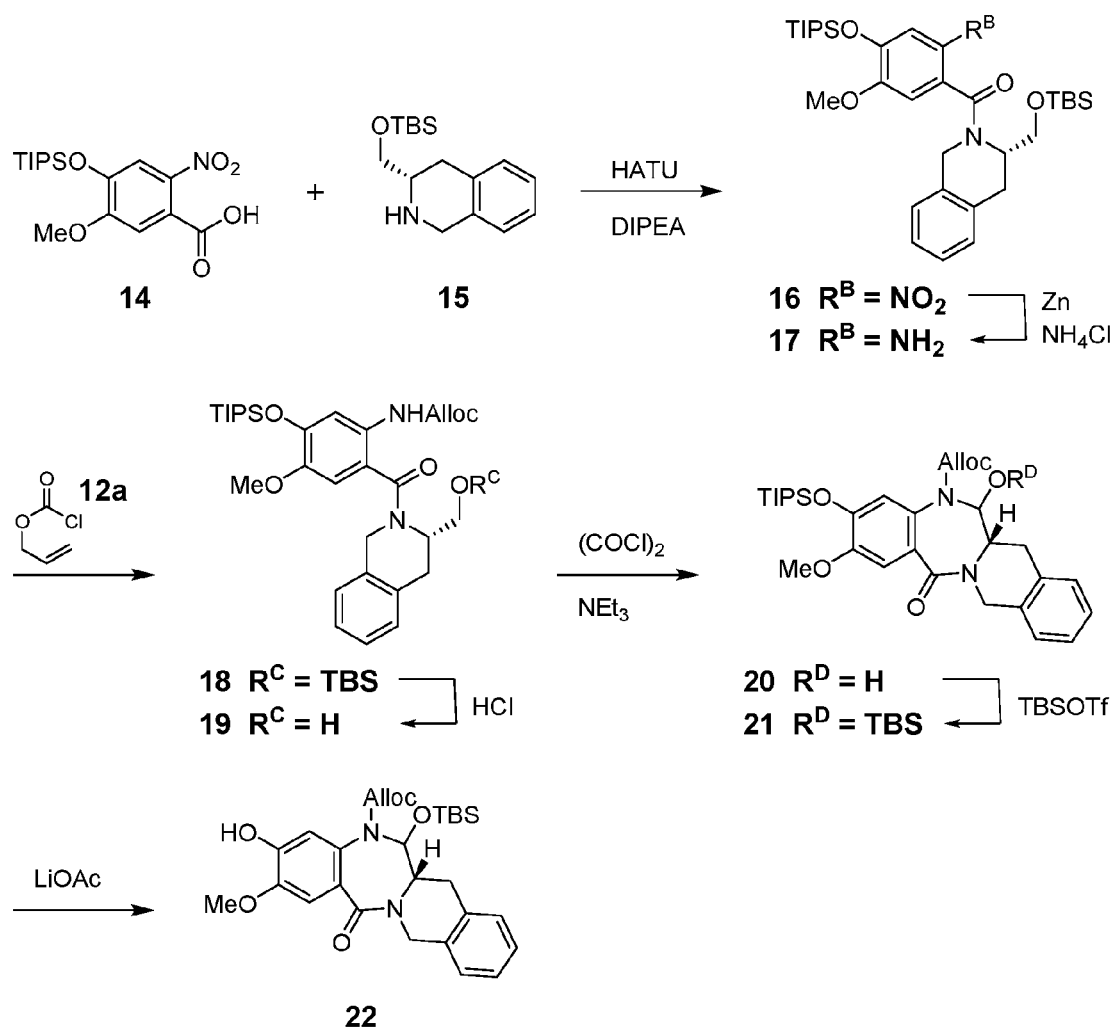
Figure 4:
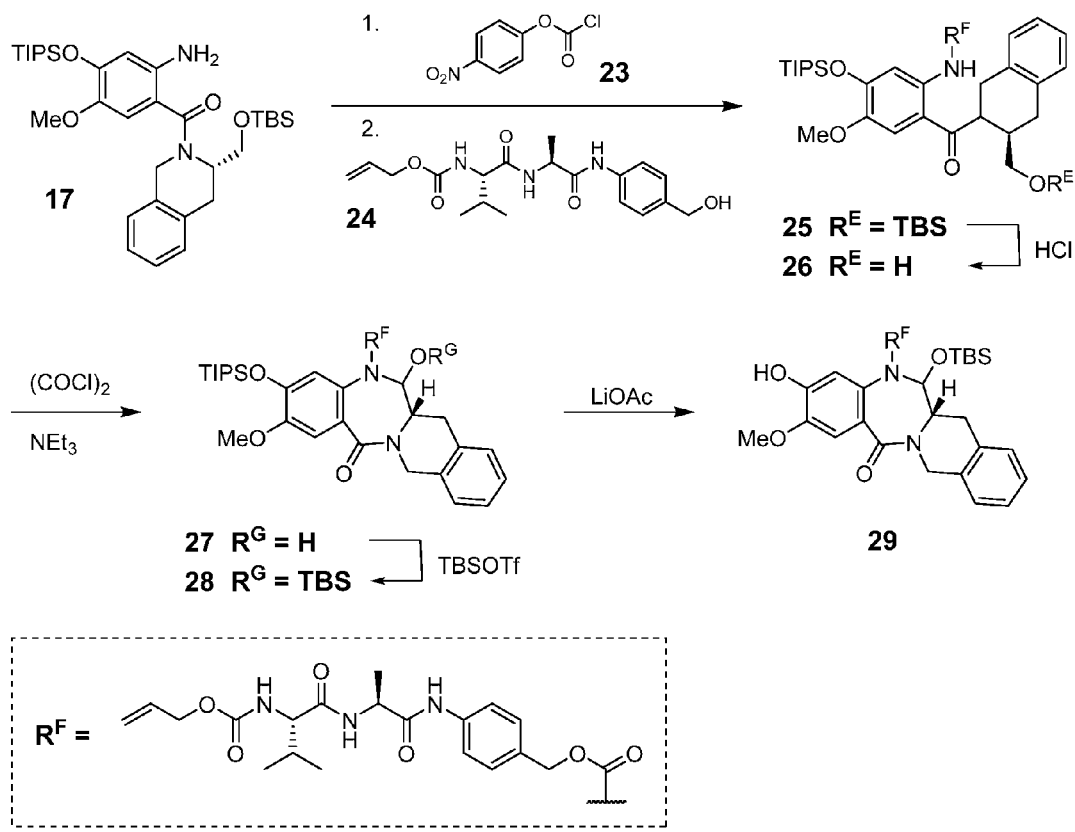

This example and FIGS. 3 and 4 relate to the preparation of additional intermediates useful in the synthesis of dimers of this invention.

A flask was charged with 5-methoxy-2-nitro-4-((triisopropylsilyl)oxy)benzoic acid 14 (CAS Reg. No. 1430738-03-6, 9.0 g, 24.36 mmol) and N,N,N',N'-tetramethyl-O-(7-azabenzotriazol-1-yl)uronium hexafluorophosphate (HATU, 10.19 g, 26.8 mmol) in DCM (100 mL) at 0° C. The reaction mixture was stirred for 10 min and treated with N.N-diisopropylethyl amine (DIEA or DIPEA, 4.68 mL, 26.8 mmol) and isoquinoline 15 (CAS Reg. No. 215928-81-7, 7.43 g, 26.8 mmol). The reaction was maintained at 0° C. for 3 h and then stirred at RT for 24 h. The reaction mixture was poured into saturated NH$_4$Cl and DCM. The organic phase was collected and concentrated to a residue. The residue was further purified by silica gel chromategraphy (Biotage) eluting with 10%-30% EtOAc in hexanes. The product was collected and concentrated to afford amide 16 as a light tan oil (10.15g, 66% yield). LCMS M+H=629.65.

A solution of amide 16 (10.1 g, 16.06 mmol) in MeOH (200 mL) was cooled to 0° C. and NH$_4$Cl (4.29 g, 80 mmol) and zinc dust (5.25 g, 80 mmol) were added. The resulting green suspension was stirred at 0° C. for 45 min, then allowed to warm to RT overnight. The reaction mixture was filtered through a CELITE™ pad (washing with MeOH) and the filtrate was concentrated to a residue. The residue was taken up in DCM and loaded onto silica gel pad. This was flushed with 50% EtOAc and hexanes to afford aniline 17 (8.02g, 83% yield). LCMS M+H=599.35.

Aniline 17 (2500 mg, 4.17 mmol) was dissolved in DCM (50 mL) and pyridine (0.878 mL, 10.85 mmol) was added. The mixture was cooled to −78° C. and allyl chloroformate 12a (0.579 mL, 5.43 mmol) was added. The reaction mixture was maintained at this temperature for 1 h and then allowed to warm to RT. The reaction mixture was poured into saturated $NH_4Cl$ and DCM. The mixture was extracted with DCM and purified by silica gel chromatography (Biotage) eluting with 10%-50% EtOAc in hexanes to afford carbamate 18 (2.5g, 88% yield). LCMS M+H=683.40.

Carbamate 18 (1.372g, 2.009 mmol) was dissolved in MeOH (20 mL). 10% concentrated HCl in MeOH (2 mL, 6.58 mmol) was added. The mixture was aged for 20 min and quenched with $NaHCO_3$ (0.591 g, 7.03 mmol) in water. The mixture was diluted with water and extracted 4× with DCM. The combined organic phases were dried over $Na_2SO_4$, filtered, and evaporated. Purification by silica gel chromatography (Biotage) eluting with 10-50% EtOAc/Hexanes afforded alcohol 19 (963mg, 84% yield).). LCMS M+H=569.25.

Oxalyl chloride (2.0M, 1.450 mL, 2.90 mmol) was dissolved in DCM (30 mL) and then the mixture was cooled to −78° C. in a dry ice/acetone bath. To this was added DMSO (0.515 mL, 7.25 mmol, dissolved in ~2 mL DCM to prevent freezing during addition) and the temperature was maintained at −78° C. After 20 mins, alcohol 19 (1.65 g, 2.90 mmol) dissolved in DCM (10 mL) was added to the reaction. This was allowed to stir for an additional 30 min and followed by addition of $NEt_3$ (2.022 mL, 14.50 mmol). After 10 min the reaction was allowed to warm up to RT. This was quenched with saturated $NH_4Cl$ and extracted with DCM (2×). The organic phases were combined, dried over $Na_2SO_4$, filtered and concentrated to residue. The residue was purified by silica gel chromatography (Biotage) eluting with 30%-100% EtOAc in hexanes. The product was collected and concentrated to afford aminal 20 as a white solid (1.51g, 92% yield).). LCMS M+H=567.30. $^1$H NMR (400 MHz, chloroform-d) δ 7.39-7.24 (m, 5H), 7.22 (s, 1H), 6.67 (s, 1H), 5.75 (dd, J=11.2, 5.6 Hz, 1H), 5.31 (dd, J=9.5, 4.0 Hz, 1H), 5.22-5.07 (m, 2H), 4.84 (d, J=15.8 Hz, 1H), 4.64-4.49 (m, 2H), 4.44 (d, J=5.3 Hz, 1H), 3.87 (s, 3H), 3.77-3.61 (m, 1H), 3.28-3.01 (m, 3H), 1.34-1.18 (m, 3H), 1.09 (dd, J=7.4, 2.6 Hz, 18H).

Aminal 20 (776 mg, 1.369 mmol) was dissolved in DCM (12 mL) and 2,6-lutidine (0.638 mL, 5.48 mmol) was added. The mixture was cooled on an ice bath and tert-butyldimethylsilyl trifluoromethanesulfonate (TBSOTf, 0.943 mL, 4.11 mmol) was added. The mixture was aged for 30 min, diluted with DCM, quenched with saturated $NaHCO_3$ solution, and extracted 2× with DCM. The combined organic phases were dried over $Na_2SO_4$, filtered, and evaporated to dryness. The residue was purified by silica gel chromatography (Biotage) eluting with 10-30% EtOAc/hexanes to afford silyl ether 21 (907.6 mg, 1.333 mmol, 97% yield) $^1$H-NMR showed the purified material was contaminated with ~0.25 equivalents 2,6-lutidine (~4 wt %), but was taken on without any further purification. LCMS M+H=681.25.

Silyl ether 21 (907 mg, 1.332 mmol) was dissolved in DMF (5 ml) and water (0.1 ml). Lithium acetate (88 mg, 1.332 mmol) was added and the mixture aged overnight. Most of the DMF was evaporated under a stream of nitrogen. The residue was diluted with EtOAc, washed 2× with 0.1M citric acid then once with brine. The organic phases were dried over $Na_2SO_4$, filtered, and evaporated to dryness. The residue was purified by silica gel chromatography (Biotage) eluting with 30-70% EtOAc/hexanes to afford phenol 22 (707.4 mg, 1.107 mmol, 83% yield) containing some EtOAc by $^1$H-NMR (approx. 1.3 equiv.; yield adjusted to account for EtOAc). LCMS M+H=525.10.

Turning now to FIG. 4, compound 17 (2.1g, 3.51 mmol) was dissolved in DCM (30 mL) and pyridine (0.3 mL, 3.71 mmol) was added. The mixture was cooled to 0° C. 4-Nitrophenyl carbonochloridate 23 (0.707 g, 3.51 mmol) was added and the mixture aged for 7 min at the same temperature. A solution of compound 24 (CAS Reg. No. 1343407-91-9, 1.323 g, 3.51 mmol) and DIEA (0.750 mL, 4.29 mmol) in DMF (3 mL) was added. The mixture was placed on a rotary evaporator at RT to remove the DCM. After 20 min, the DMF was evaporated under a stream of nitrogen and then the residue was purified by silica gel chromatography (Biotage) eluting with 10-100% EtOAc in hexanes to afford compound 25 (1.579 g, 1.575 mmol, 44.9% yield). LCMS M+H=1002.50.

A solution of compound 25 (1.579g, 1.575 mmol) in MeOH (14.4 ml) was treated with 10% concentrated HCl in MeOH (1.6 ml, 5.27 mmol). The mixture was aged 30 min, quenched with saturated $NaHCO_3$, and extracted with chloroform (3×). The combined organic phases were dried over $Na_2SO_4$, filtered and evaporated to leave a residue. The residue was combined with another batch of the same reaction (starting with 0.816 g of compound 25) for purification. The combined crude residues were purified by silica gel chromatography (Biotage) eluting with 20-100% EtOAc/Hexanes to afford carbamate 26 (1.7412 g, 1.961 mmol, 82% yield). LCMS M+H=888.30.

A solution of oxalyl chloride (2.0M, 1.00 mL, 2.000 mmol) in 10 mL DCM was cooled to −78° C. A solution of DMSO (0.348 mL, 4.90 mmol) in 5 mL DCM was added dropwise and the mixture aged at the same temperature for 10 min. A solution of carbamate 26 (1741.2 mg, 1.961 mmol) in 5 mL DCM was added dropwise and the mixture was again aged for 15 min. $NEt_3$ (1.366 mL, 9.80 mmol) was added dropwise; the mixture was aged at the same temperature for 5 min and then the cold bath was removed and the mixture was allowed to warm to RT. The mixture was quenched with $NH_4Cl$ solution and extracted twice with DCM. The combined organic phases were washed with water and brine, dried over $Na_2SO_4$, filtered, and evaporated. The residue was purified by silica gel chromatography (Biotage) eluting with 50-80% EtOAc/Hexanes to afford compound 27 (1376.7 mg, 1.554 mmol, 79% yield). LCMS M+H=886.30.

Compound 27 (1045 mg, 1.179 mmol) was dissolved in DCM (10 ml) and 2,6-lutidine (0.549 ml, 4.72 mmol) was added. The mixture was cooled on an ice bath and tert-butyldimethylsilyl trifluoromethanesulfonate (0.813 ml, 3.54 mmol) was added. After 1 h, the mixture was diluted with DCM, washed with saturated $NaHCO_3$ and brine, dried over $Na_2SO_4$, filtered and evaporated. The residue was purified by silica gel chromatography (Biotage) eluting 20-100% EtOAc/Hexanes. Some mixed fractions were obtained, which were repurified by silica gel chromatography (Biotage) eluting with 50% EtOAc/Hexanes (isocratic). The pure fractions were combined to afford compound 28 (676.9 mg, 0.677 mmol, 57.4% yield). LCMS M+H=1000.30.

A solution of compound 28 (676 mg, 0.676 mmol) in DMF (5 mL) and water (0.1 mL) was treated with LiOAc (44.6 mg, 0.676 mmol). The mixture was aged overnight, and the solvent was evaporated under a stream of nitrogen. The residue was partitioned between EtOAc and 0.1M citric acid. The phases were separated and the organic phases were washed twice with 0.1M citric acid, once with brine and then dried over $Na_2SO_4$, filtered and evaporated. The residue was purified by silica gel chromatography (Biotage) eluting with 50-100% EtOAc/Hexanes to afford compound 29 (543.6 mg, 0.644 mmol, 95% yield). LCMS M+H=844.35.

Example 4

Linker with PABC Group

Figure 5:
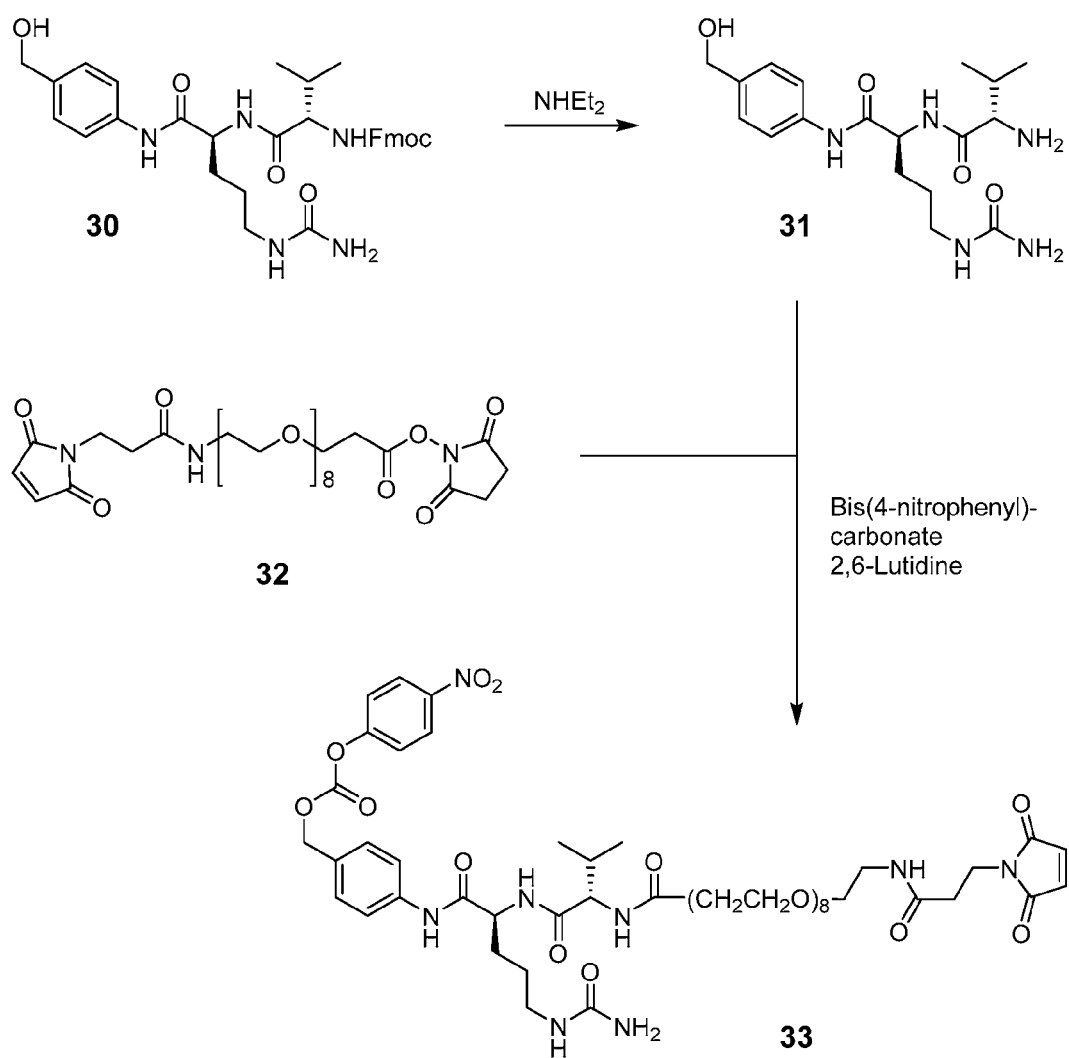

This example and FIG. 5 relate to linker with a PABC self-immolating group.

To a solution of compound 30 (Firestone et al. U.S. Pat. No. 6,124,345 B1 (2001), Example 57; 0.75 g, 1.246 mmol) in DMF (2 ml) and THF (8 mL) was added diethylamine (2.81 ml, 26.9 mmol). The reaction was stirred at RT for 1.5 h and concentrate. The crude product was triturated with DCM, filtered and dried under vaccume to give compound 31 as a white solid. LCMS (M+H)=380.2 $^1$H NMR (400 MHz, DMSO-$d_6$) □ 10.06 (s, 1H), 8.15 (d, J=7.3 Hz, 1H), 7.56 (d, J=8.5 Hz, 2H), 7.26 (d, J=8.3 Hz, 2H), 6.00 (t, J=5.4 Hz, 1H), 5.43 (s, 2H), 5.13 (t, J=5.3 Hz, 1H), 4.56-4.33 (m, 3H), 3.07-2.93 (m, 3H), 2.00-1.55 (m, 5H), 1.49-1.32 (m, 2H), 0.90 (d, J=6.8 Hz, 3H), 0.80 (d, J=6.8 Hz, 3H).

To a solution of compound 31 (79 mg, 0.209 mmol) in DMSO (2 mL) was added a solution of MAL-dPEG® 8-NHS ester 32 (QuantaBio, 120 mg, 0.174 mmol) in DMSO (1 mL), followed by 2,6-lutidine (37.3 mg, 0.348 mmol). The reaction was stirred at RT for 3 h. A solution of bis(4-nitrophenyl) carbonate (63.5 mg, 0.209 mmol) in DMF (2 mL) was added, followed by 2,6-lutidine (37.3 mg, 0.348 mmol). The reaction was then stirred at RT for 12 h. DIPEA (0.061 mL, 0.348 mmol) was then added, and the reaction was stirred at RT for 3 h. The crude product mixture was diluted with DMF, filtered, and purified using reverse phase HPLC (Column: Phenomenex Luna C18 20×100mm; Mobile Phase A: 10:90 acetonitrile:water with 0.1% TFA; Mobile Phase B: 90:10 acetonitrile:water with 0.1% TFA; Gradient: 0-70% B over 15 minutes; Flow: 20 mL/min; Detection: UV at 220 nm) to give compound 33 (40 mg, 0.036 mmol, 20.54% yield). LCMS (M+H)=1119.5.

Example 5

Dimers IIa-01 and IIa-05

Figure 6:
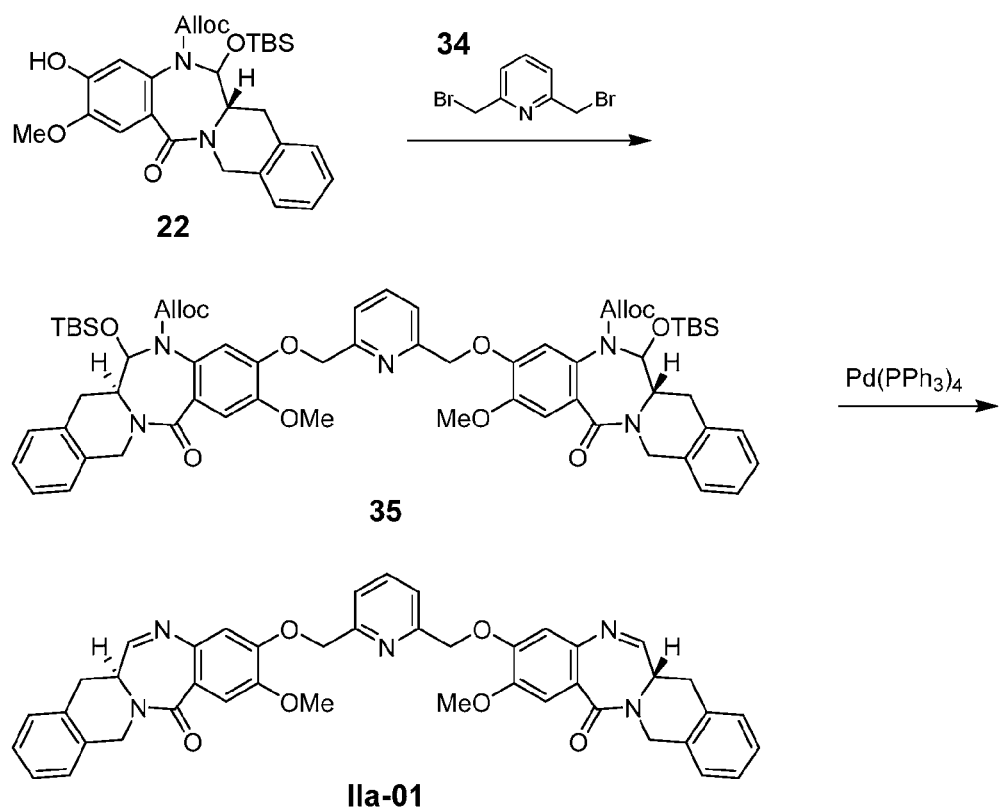

This example and FIG. 6 relate to the synthesis of dimer IIa-01.

A suspension of phenol 22 (60 mg, 0.114 mmol), 2,6-bis (bromomethyl)pyridine 34 (15 mg, 0.057 mmol, available from Sigma Aldrich) and $Cs_2CO_3$ (37 mg, 0.114 mmol) in acetone (0.4 ml) was warmed to 40° C. for 1 h. The mixture was quenched with 0.1 M citric acid and extracted thrice with EtOAc. The combined organic phases were washed with brine and dried over $Na_2SO_4$, filtered and evaporated. The mixture was purified by silica gel chromatography, eluting with a gradient from 30-80% EtOAc in hexanes to afford dimer 35 (36.2 mg, 55% yield). LCMS M+H=1153.40.

Dimer 35 (36 mg, 0.031 mmol) was dissolved in a solution of pyrrolidine in DCM (0.042 M, 1.9 ml, 0.078 mmol) and tetrakis(triphenylphosphine)palladium (Pd (PPh$_3$)$_4$, 2.2 mg, 1.9 µmol) was added. The mixture was stirred for 30 minutes, at which point it was partitioned between DCM and saturated $NH_4Cl$. The phases were separated and the aqueous fraction was extracted twice more with DCM. The combined organic phases were dried over $Na_2SO_4$, filtered and evaporated to a residue, which was then purified by preparative HPLC (Sunfire C18 prep OBD column 19×100mm; Solvent A=95% water, 5% Acetonitrile+0.1% TFA; Solvent B=5% water, 95% Acetonitrile+ 0.1% TF;. gradient of 0-100% over 10 min; hereinafter referred to as "HPLC Procedure A"). The sample was divided into two equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and the water was removed by lyophilization to afford dimer IIa-01 as a white powder (13.4 mg, 56% yield). LCMS M+H=720.10. HRMS found: M+H=720.2808, calc'd: 720.2817.

Using 2,4-bis(bromomethyl)pyridine instead as the bridging moiety, dimer IIa-05 was analogously prepared.

A suspension of phenol 22 (170 mg, 0.414 mmol), 2,4-bis(bromomethyl)pyridine (50 mg, 0.189 mmol) and $Cs_2CO_3$ (170 mg, 0.522 mmol) in DMF (1.0 ml) was stirred at 25° C. for 1 h. The mixture was quenched with water 20 mL and filtered. The percipitate was washed with diethyl ether and air dried. The material was purified by silica gel chromatography, eluting with a gradient from 5-50% acetone in DCM to afford the Alloc-TBS compound analogous to dimer 35 (134 mg, 70% yield). LCMS M+H=1153.40.

The Alloc-TBS compound (36 mg, 0.031 mmol) was dissolved in a solution of pyrrolidine in DCM (0.042 M, 1.9 ml, 0.078 mmol) and Pd(PPh$_3$)$_4$ (2.2 mg, 1.9 µmol) was added. The mixture was stirred for 30 min and partitioned between DCM and saturated $NH_4Cl$. The phases were separated and the aqueous fraction extracted twice more with DCM. The combined organic phases were dried over $Na_2SO_4$, filtered and evaporated to a residue which was then purified by HPLC Procedure A. The sample was divided into two equal injections. The fractions containing the product were combined and passed through a PL-HCO3- MP SPE 500 mg/6 mL cartridge, eluting with acetonitrile to afford a solution of the product as a free base. The bulk of the organic solvent was removed by rotary evaporation and the aqueous water was removed by lyophilization to afford dimer IIa-05 as a white powder (16.0 mg, 65% yield). LCMS M+H=720.10.

Example 6

Dimer-Linkers IIIb-01 and IIIb-02

Figure 7A:
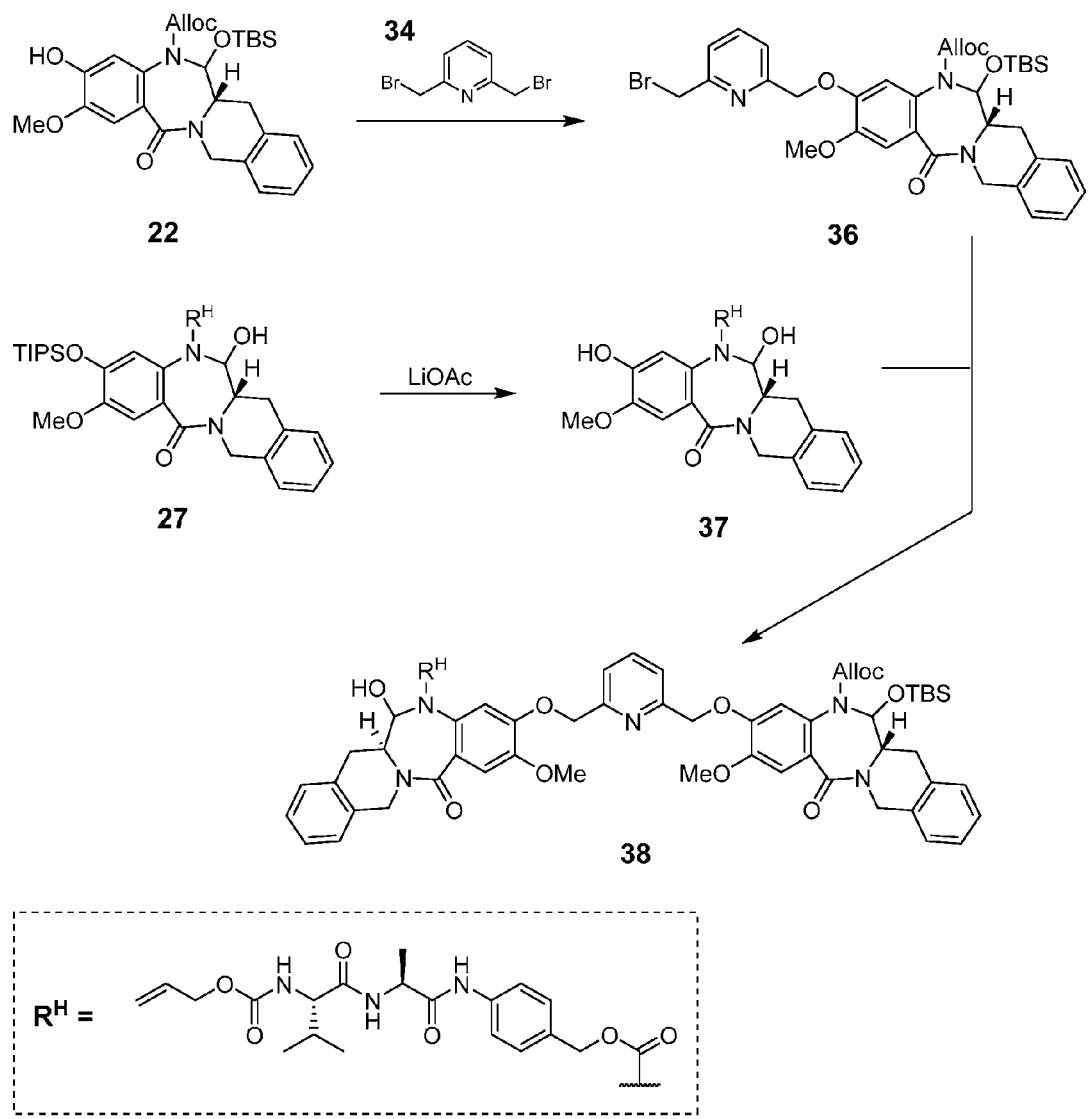
Figure 7B:
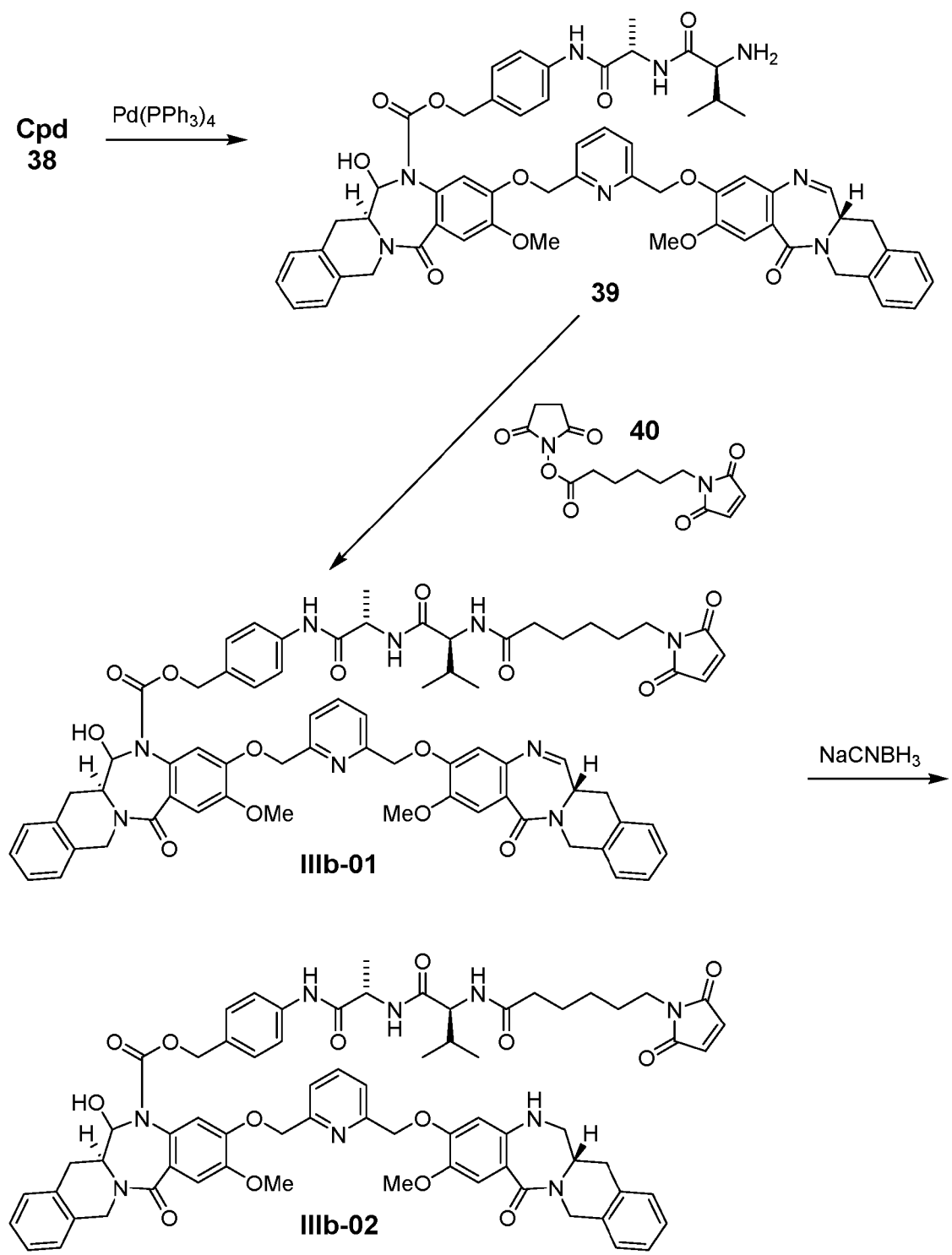

This example and FIGS. 7A and 7B in combination pertain to the preparation of dimer-linkers IIIb-01 and IIIb-02.

A suspension of phenol 22 (480 mg, 0.823 mmol), 2,6-bis(bromomethyl)pyridine 34 (654 mg, 2.47 mmol, available from Sigma Aldridge) and $Cs_2CO_3$ (500 mg, 1.54 mmol) in DMF (3.0 ml) was stirred at RT for 1 h. The mixture was quenched with 0.1 M citric acid and extracted thrice with EtOAc. The combined organic phases were washed with brine and dried over $Na_2SO_4$, filtered and evaporated. The mixture was purified by silica gel chromatography, eluting with a gradient from 30-80% EtOAc in hexanes to afford compound 36 (465 mg, 80% yield). LCMS M+H=708.05.

Silyl ether 27 (431 mg, 0.486 mmol) was dissolved in DMF (2.0 mL) and water (0.04 mL) and treated with LiOAc (32 mg, 0.486 mmol). The mixture was warmed to 40° C. for 2.5 h and allowed to stir at RT for an additional hour. The solvent was removed under a stream of $N_2$ over 3 days. The residue was treated with 0.1 M citric acid and extracted thrice with EtOAc. The combined organic phases were dried over $Na_2SO_4$, filtered and evaporated. The mixture was purified by silica gel chromatography, eluting with a gradient from 0-10% MeOH in DCM to afford phenol 37 (297 mg, 84% yield). LCMS M+H=730.40.

Phenol 37 (178 mg, 0.244 mmol), compound 36 (190 mg, 0.268 mmol) and $Cs_2CO_3$ (79 mg, 0.244 mmol) were suspended in DIIIF (0.7 mL) and warmed to 40° C. for 3.5 h. The mixture was added to water and filtered to collect compound 38 as a white solid (320 mg, 97% yield). LCMS M+H=1357.30.

Compound 38 (320 mg, 0.236 mmol) was dissolved in a solution of pyrrolidine in DCM (0.042 M, 14 ml, 0.589 mmol) and $Pd(PPh_3)_4$ (15 mg, 13 µmol) was added. The mixture was stirred for 2.5 h, at which point it was partitioned between DCM and saturated $NH_4Cl$. The phases separated and the aqueous fraction extracted twice more with DCM. The combined organic phases were dried over $Na_2SO_4$, filtered and evaporated to residue, which was then purified by HPLC Procedure A. The sample was divided into 10 equal injections. The fractions containing the product peak were combined and passed through a PL-HCO3-MP SPE 500 mg/6 mL cartridge, eluting with acetonitrile to afford a solution of the product as a free base. The bulk of the organic solvent was removed by rotary evaporation and water was removed by lyophilization to afford amine 39 as a white powder (145 mg, 58% yield). LCMS M+Na=1078.90.

Amine 39 (145 mg, 0.137 mmol) was dissolved in a solution of DIPEA in DMF (0.05 M, 3.3 ml, 0.165 mmol) and maleimide 40 (85 mg, 0.274 mmol, available from Sigma Aldridge) was added. The mixture was stirred for 20 h, at which point it was diluted with DMF and purified by HPLC Procedure A. The sample was divided into 8 equal injections.

The fractions containing product were combined and passed through a PL-HCO3- MP SPE 500 mg/6 mL cartridge, eluting with acetonitrile to afford a solution of the product as a free base. The bulk of the organic solvent was removed by rotary evaporation and the water was removed by lyophilization to afford dimer-linker IIIb-01 as a white powder (68 mg, 38% yield). LCMS M+H=1251.10.

Dimer-linker IIIb-01 (20.0 mg, 0.016 mmol), was dissolved in THF (1 ml) and AcOH (0.1 ml) and a solution of NaCNBH3 (2.0 mg, 0.032 mmol) in MeOH (1 ml) was added. The mixture was stirred for 1 h, at which point it was diluted with acetonitrile and then purified by HPLC Procedure A. The sample was divided into 2 equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and the water was removed by lyophilization to afford dimer-linker IIIb-02 as a white powder (16 mg, 76% yield). LCMS (M+2H)/2=627.10.

Example 7

Dimer IIa-02

Figure 8:
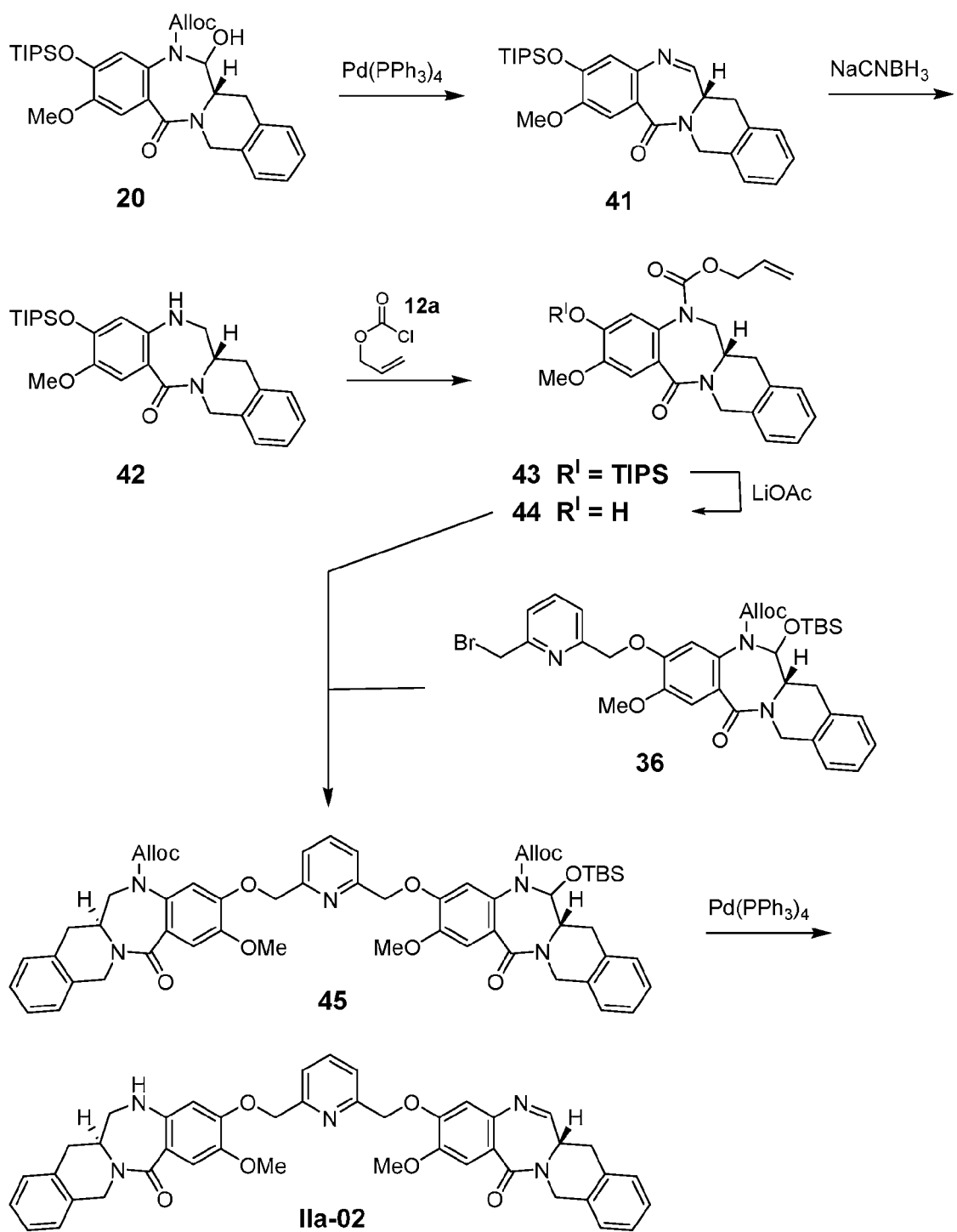

This example and FIG. 8 relate to the preparation of dimer IIa-02.

Aminal 20 (500 mg, 0.244 mmol), was dissolved in DCM (10 ml) and pyrrolidine (0.18 ml, 2.21 mmol) and $Pd(PPh_3)_4$ (51 mg, 44 µmol) were added. The mixture was stirred for 45 min and partitioned between DCM and saturated $NH_4Cl$. The phases were separated and the aqueous fraction extracted twice more with DCM. The combined organic phases were dried over $Na_2SO_4$, filtered and evaporated to residue to afford imine 41 (410 mg, 100% yield), which was used without further purification. LCMS M+H=465.20.

Imine 41 (410 mg, 0.882 mmol), was dissolved in THF (8 ml) and acetic acid (0.8 ml) and a solution of NaCNBH3 (111 mg, 1.77 mmol) was added. The mixture was stirred for 2 h, quenched with $NaHCO_3$ and extracted 3× with EtOAc. The combined organic phases were dried over $Na_2SO_4$, filtered and evaporated to residue to afford amine 42 (315 mg, 77% yield), which was used without further purification. LCMS M+H=467.30.

Amine 42 (315 mg, 0.675 mmol), was dissolved in DCM (7 ml) and pyridine (0.15 ml, 1.86 mmol) was added and the mixture cooled to −78° C. Allyl chloroformate 12a (0.10 ml, 1.39 mmol) was added dropwise and the mixture was stirred at the same temperature for 30 min, at which point it was quenched with saturated $NH_4Cl$ and extracted 3× with DCM. The combined organic phases were dried over $Na_2SO_4$, filtered and evaporated to residue to afford a residue that was puried by silica gel chromatography, eluting with a gradient from 20-50% EtOAc in hexanes to afford alloc-protected amine 43 (372 mg, 100% yield). LCMS M+H=551.50.

Amine 43 (372 mg, 0.675 mmol) was treated in the same manner as was used for the preparation of phenol 37, except that the reaction was held at RT overnight instead of warming. This afforded phenol 44 (249 mg, 93% yield). LCMS M+H=395.05.

Phenol 44 (30 mg, 0.076 mmol), compound 36 (30 mg, 0.042 mmol) and $Cs_2CO_3$ (30 mg, 0.092 mmol) were suspended in DMF (0.25 mL) and warmed to 40° C. for 1 h. The mixture was treated with 0.1 M citric acid and extracted thrice with EtOAc. The combined organic phases were dried over $Na_2SO_4$, filtered and evaporated. The mixture was purified by silica gel chromatography, eluting with a gradient from 30-100% EtOAc in hexanes to afford compound 45 (32 mg, 74% yield). LCMS M+H=1022.10.

Compound 45 (32 mg, 0.031 mmol) was dissolved in a solution of pyrrolidine in DCM (0.042 M, 2.0 ml, 0.08 mmol) and $Pd(PPh_3)_4$ (1.8 mg, 1.6 µmol) was added. The mixture was stirred for 2.5 h, after which it was evaporated, diluted with DMF and then purified by HPLC Procedure A. The sample was divided into 3 equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and the water was removed by lyophilization to afford dimer IIa-02 as a white powder (12 mg, 53% yield). LCMS M+H=722.30.

Example 8

Dimer IIa-03

Figure 9:
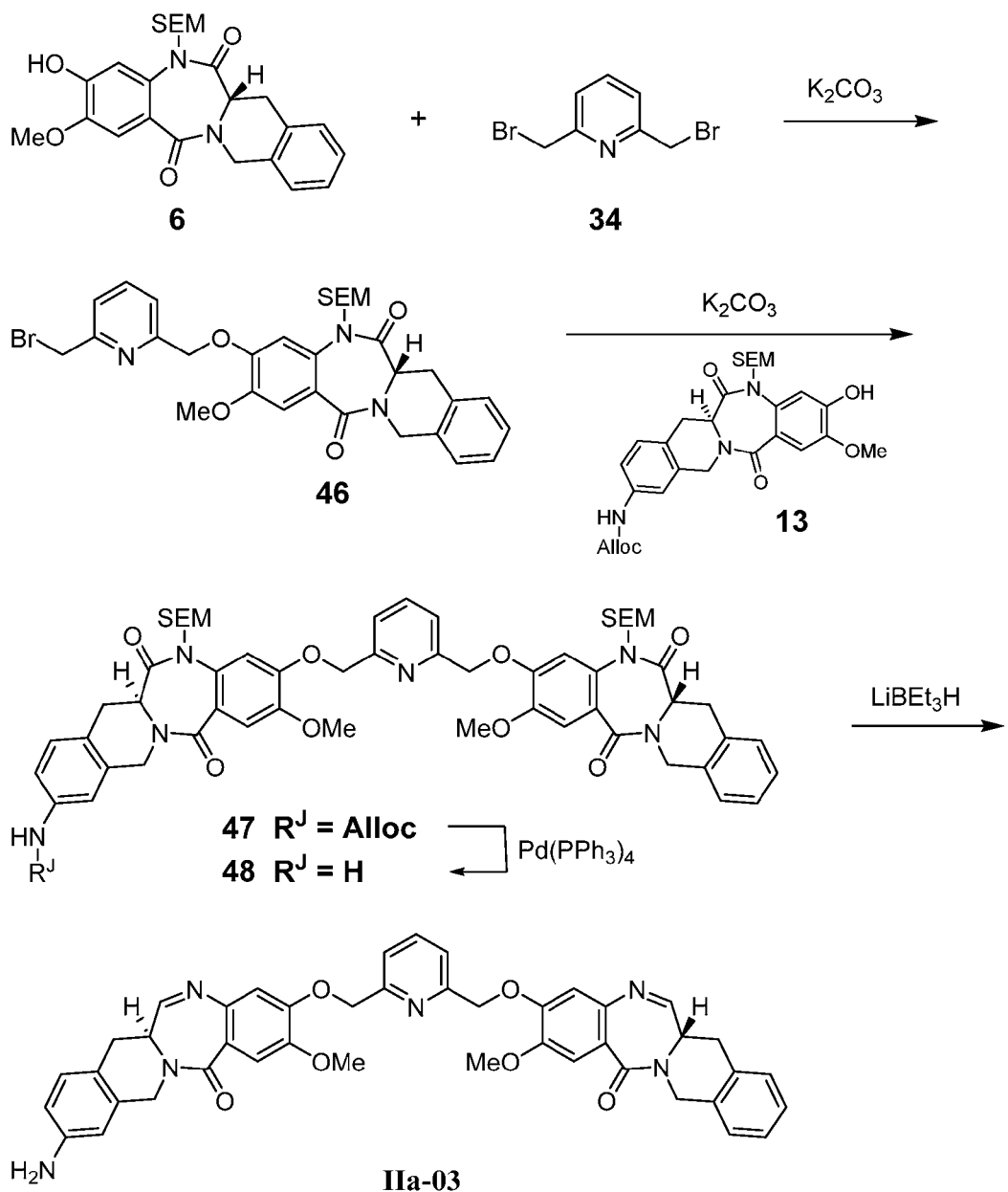

This example and FIG. 9 relate to the synthesis of dimer IIa-03.

In a flask was added compound 6 (1.830 g, 4.03 mmol) in DMF (20 mL). To this was added 2,6-bis(bromomethyl)pyridine 34 (3.2 g, 12.08 mmol) followed by $K_2CO_3$ (1.669 g, 12.08 mmol). The reaction was allowed to proceed, with stirring, at RT overnight and then was quenched by pouring into water. The reaction mixture was extracted with EtOAc and washed with saturated NaCl. The organic phase was concentrated to a residue and purified on a COMBIFLASH™ column, eluting with a 10%-100% EtOAc in hexanes gradient to yield compound 46 (2.3 g, 89% yield) as white solid.

In a flask were combined compound 46 (1.0 g, 1.566 mmol) and compound 13 (1.084 g, 1.957 mmol) in DMF (5 mL). To this was added $K_2CO_3$ (0.649 g, 4.70 mmol).

After 4 h the reaction mixture was poured into water and extracted with EtOAc. The organic layer was concentrated and purified on a COMBIFLASH™ column, eluting with a 0-100% EtOAc in hexanes gradient to obtain compound 47 (856 mg, 49.2% yield) as white solid.

To a flask was added compound 47 (850 mg, 0.765 mmol) in DCM (10 mL). To this was added $Pd(PPh_3)_4$ (88 mg, 0.076 mmol) and pyrrolidine (0.158 mL, 1.912 mmol). The reaction mixture was stirred at RT for 1 h. The reaction mixture was poured into water and DCM. The organic phase was collected and concentrated to a residue. The residue was purified on a COMBIFLASH™ column, eluting with 0%-30 MeOH in DCM to obtain compound 48 (500 mg, 63.6% yield) as white solid.

To a solution of compound 48 (26 mg, 0.025 mmol) in THF (1 mL) was added SUPER HYDRIDE™ (0.127 mL, 0.127 mmol) at −76° C. The reaction mixture was stirred for 1 h. The reaction was quenched with cold water (1 mL) and extracted with DCM (3×10 mL). The organic layer was concentrated and treated with DCM/EtOH/water (1:2:1, 4 mL) and silica gel (1 g) for 3 days. This mixture was filtered through a sintered funnel and the silica gel was washed with DCM-MeOH (8:2, 100 mL). The filtrate was concentrated under high vacuum and purified on 12 g silica gel column using 0-10% MeOH/DCM eluent to provide dimer IIa-03 (16 mg, 0.021 mmol, 82% yield) as white solid. MS (m+1) =735.2.

Example 9

Dimer-Linkers IIIc-01, IIIc-03, and IIIc-04

Figure 10:
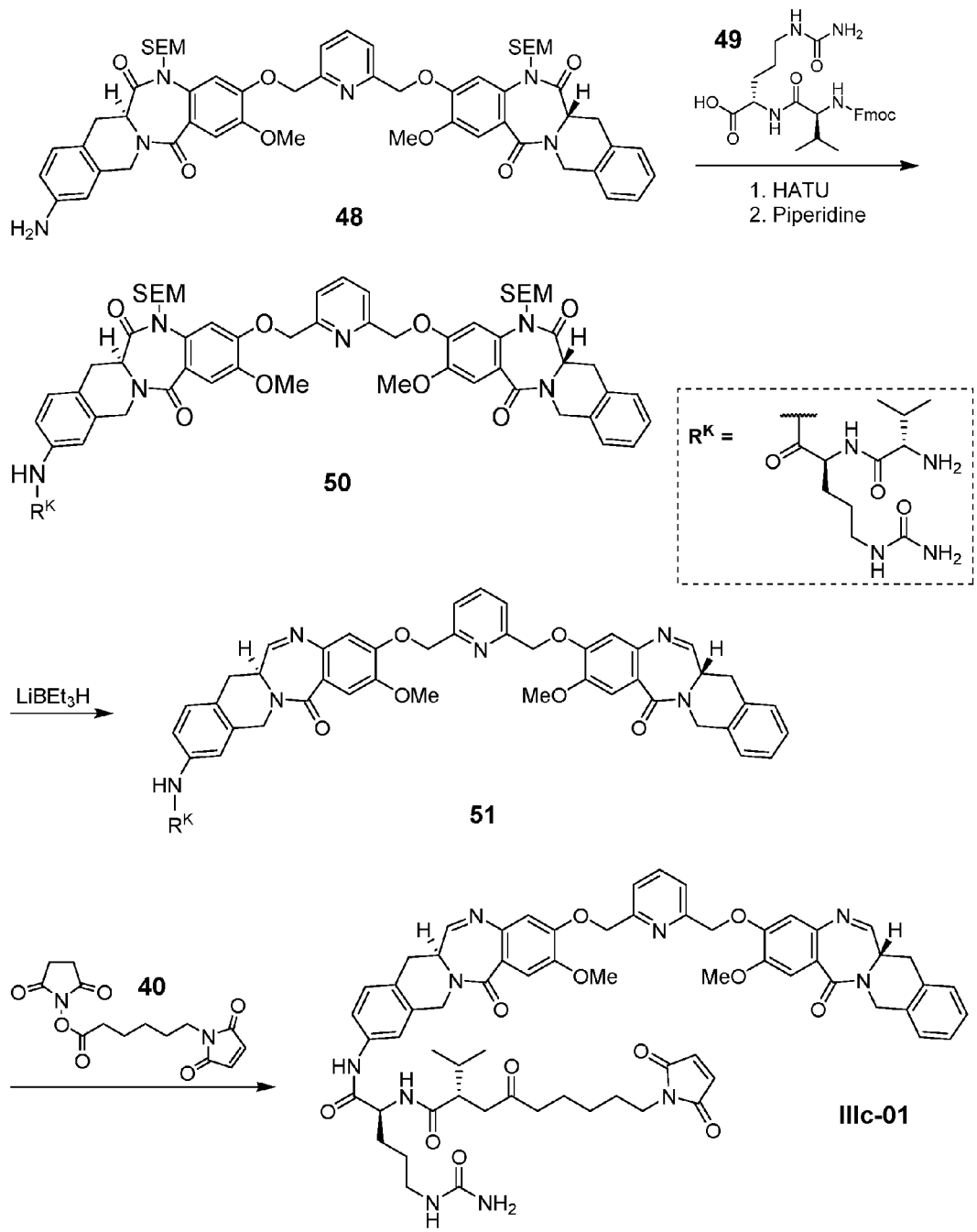

This example and FIG. 10 relate to the synthesis of dimer-linker IIIc-01, IIIc-03, and IIIc-04.

To a solution of compound 48 (1.15 g, 1.119 mmol), acid 49 (0.667 g; 1.343 mmol; Firestone et al., U.S. Pat. No. 6,214,345 B1 (2001)), and HATU (0.511 g, 1.343 mmol) in DMF (11 mL) at 0° C. was added 2,6-lutidine (0.261 mL, 2.239 mmol). The reaction mixture was stirred at RT for 1 h. The reaction was then diluted with EtOAc (200 mL), and washed with water, and then brine. The aqueous phase was extracted with EtOAc (2×100 mL). The combined organic phases were dried over $Na_2SO_4$ and concentrated and taken up in THF (20 mL). Piperidine (2 mL) was added and the reaction mixture was stirred at RT for 30 min. The reaction mixture was concentrated and purified on an ISCO COMBIFLASH™ (40 g column, 0-40% MeOH/DCM) over 32 min to provide compound 50 (0.997 g, 69.4% yield) as white solid. MS (m+1)=1284.6. $^1$H NMR (400 MHz, $CDCl_3$) ☐ 10.01 (s, 2H), 8.27 (m, 2H), 7.96 (t, J=8.0 Hz, 2H), 7.55 (m, 4H), 7.42 (dd, J=8.0, 1.6 Hz, 2H), 7.20-7.31 (m, 12H), 5.98 (t, J=5.6 Hz, 2H), 5.89 (brs, 1H), 5.43 (brs, 2H), 5.35 (brs, 1H), 5.25 (m, 8H), 5.10 (d, J=10.0 Hz, 1H), 5.09 (d, J=10.4 Hz, 1H), 4.95 (d, J=15.6 Hz, 2H), 4.75 (brs, 1H), 4.50 (brs, 2H), 4.32 (m, 6H), 4.09 (q, J=5.2 Hz, 4H), 3.83 (s, 3H), 3.82 (s, 3H), 3.40 (q, J=7.6 Hz, 1H), 3.17 (d, J=5.2 Hz, 8H), 3.00 (m, 10H), 2.68 (t, J=1.6 Hz, 1H), 2.33 (t, J=1.6 Hz, 2H), 1.97 (m, 3H), 1.63 (m, 10H), 1.42 (m, 6H), 0.91 (d, J=7.2 Hz, 3H), 0.84 (d, J=6.8 Hz, 3H), 0.75 (m, 4H), 0.08 (s, 18H).

To a solution of compound 50 (322 mg, 0.251 mmol) in THF (10 mL) at −76° C. was added SUPER HYDRIDE™ (1.254 mL, 1.254 mmol) and stirred for 1 h. The reaction was quenched with cold water (1 mL) and concentrated. The resulting residue was treated with DCM/EtOH/water (1:2: 1=8 mL) and silica gel (1 g) for 2 days. This mixture was filtered through a sintered funnel and the silica gel was washed with DCM-MeOH (8:2, 100 mL). The filtrate was concentrated under high vacuum and purified on a 24g silica gel column using 0-50% MeOH/DCM eluent over 15 min to provide compound 51 (248 mg, 90% yield) as white solid. MS (m+1)=991.4.

To a solution of compound 51 (88 mg, 0.089 mmol) and compound 40 (54.7 mg, 0.178 mmol) in DMSO (6 mL) was added DIPEA (0.031 mL, 0.178 mmol). The reaction mixture was stirred at RT for 45 min. The reaction mixture was purified by R- HPLC using an XBridge prep OBD C18, 5 μm column (30×150 mm) and 5-60% acetonitrile/water (0.05% formic acid) elution gradient over 30 min. A fraction collected at 16.9 min was filtered through a basic resin (PL-$HCO_3$ MP -Resin 1.8 mmol/g; Agilent Part #PL3540-#603), washed with acetonitrile (5 mL) and lyophilized to provide dimer-linker IIIc-01 (39.1 mg, 0.031 mmol, 35.0% yield) as white solid. MS (m+1)=1184.3

Dimer-linkers IIIc-03 amd IIIc-04 were analogously prepared from compound 51 and dimer IIa-03, respectively using the appropriate Fmoc-protected N-hydroxysuccinimide below, followed by removal of the Fmoc group with piperidine.

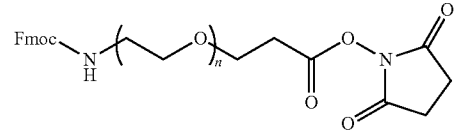

CAS Reg. No. 1314378-14-7, n = 4
CAS Reg. No. 1334170-03-4, n = 8

Dimer-linker IIIc-03 has a linker terminated with an amino group and thus can be the amine donor component in a transglutaminase mediated conjugation. MS (m+1) =1414.5.

Dimer-linker IIIc-04 also has a linker terminated with an amino group and thus can be the amine donor component in a transglutaminase mediated conjugation. Lacking a peptide group, dimer-linker IIIc-04 is of the non-cleavable type, relying on degradation of the antibody to which it is attached to release the dimer drug. MS (m+1)=982.53.

Example 10

Dimer IIa-04

Figure 11:
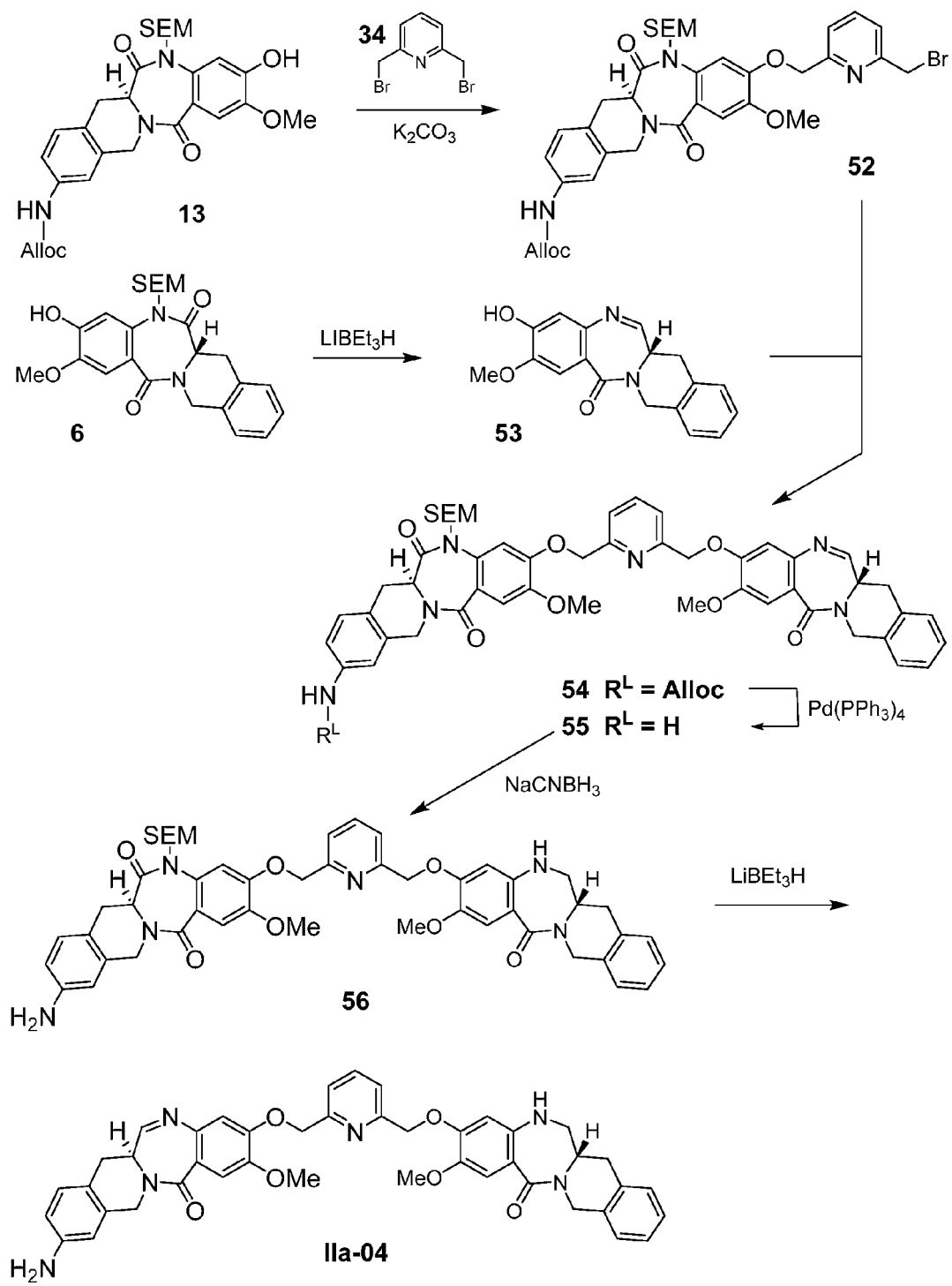

This example and FIG. 11 relate to the synthesis of dimer IIa-04.

2,6-Bis(bromomethyl)pyridine 34 (4.31 g, 16.25 mmol), compound 13 (1.8 g, 3.25 mmol) and DMF (20 mL) were combined in a flask. To this was added $K_2CO_3$ (0.899 g, 6.50 mmol). The reaction mixture was stirred at RT for 2 h and poured into water (200 mL) and EtOAc (200 mL). The organic layer was washed with water (100 mL) and brine (50 ml) and concentrated to a residue. The residue was purified on a COMBIFLASH™ 80 g column eluting with 0-100% EtOAc in hexanes gradient elution over 30 min to obtain compound 52 (1.409 g, 1.910 mmol, 58.8% yield) as white solid. MS (m+1)=737.1. $^1$H NMR (400 MHz, CDCl3) ☐ 7.80 (m, 1H), 7.54 (m, 1H), 7.45 (d, J=7.2 Hz, 1H), 7.37 (s, 2H), 7.28 (m, 4H), 6.62 (s, 1H), 5.98 (m, 1H), 5.42 (d, J=10.0 Hz, 1H), 5.37 (m, 1H), 5.28 (d, J=7.2 Hz, 1H), 5.12 (d, J=15.6 Hz, 1H), 4.69 (d, J=6 Hz, 1H), 4.65 (d, J=9.6 Hz, 1H), 4.61 (s, 1H), 4.42 (d, J=15.6 Hz, 1H), 4.27 (t, J=6.8 Hz, 1H), 3.95 (s, 3H), 3.65 (m, 2H), 3.51 (dd, J=15.6, 7.2 Hz, 1H), 2.97 (dd, J=15.6, 6.4 Hz, 1H), 0.97 (m, 2H), 0.04 (s, 9H).

To a solution of compound 6 (2 g, 4.40 mmol) in THF (20 mL) was added SUPER HYDRIDE™ (22.00 mL, 22.00 mmol) at –-76° C. The reaction mixture was stirred at that temperature for 1 h. The reaction was quenched with cold water (100 mL) and extracted with DCM (3×100 mL). The resulting residue was treated with DCM/EtOH/water (1:2:1=40 mL) and silica gel (10 g) for 3 days. This mixture was filtered through a sintered funnel and the silica gel was washed with DCM-MeOH (8:2, 100 mL). The filtrate was concentrated under high vacuum and purified on 40 g silica gel column using MeOH/DCM over 15 min. The 10% MeOH/DCM fraction at 10 min provided compound 53 (1.35 g, 4.03 mmol, 92% yield) as yellow solid. MS (m+1) =309.0.

To a solution of compound 52 (1.265 g, 1.715 mmol) and compound 53 (0.582 g, 1.886 mmol) in DMSO (10 mL) was added $K_2CO_3$ (0.474 g, 3.43 mmol). The reaction mixture was stirred at RT for 1 h and poured into water and EtOAc (1:1, 300 mL). The organic layer was concentrated and purified on a 40 g silica gel column using MeOH/DCM elution over 15 min to provide compound 54 (1.78 g, 1.568 mmol, 91% yield) as yellow solid. MS (m+1)=965.3.

To a solution of compound 54 (1.78 g, 1.844 mmol) and Pd(PPh$_3$)$_4$ (0.107 g, 0.092 mmol) in DCM (30 mL) was added pyrrolidine (0.305 mL, 3.69 mmol). The reaction mixture was stirred at RT for 30 min. Concentration and purification on a 40 g silica gel column using MeOH/DCM elution over 15 min to yielded compound 55 (1.54 g, 1.748 mmol, 95% yield) as white solid. MS (m+1)=881.2

To a solution of compound 55 (100 mg, 0.113 mmol) in THF (2 mL) was added a drop of acetic acid followed by NaCNBH3 (14.27 mg, 0.227 mmol) in MeOH (0.2 mL) at 0° C. The reaction mixture was stirred at RT for 20 min, diluted with EtOAc (50 mL), and washed with saturated NaHCO$_3$ solution (10 mL) and brine (10 mL). The organic layer was concentrated and purified on an ISCO COMBIFLASH™ 24 g column using MeOH/DCM) over 15 min to provide compound 56 (37 mg, 0.042 mmol, 36.9% yield) as white solid. MS (m+1)=883.4. $^1$H NMR (400 MHz, CDCl$_3$) ☐ 7.73 (t, J=8.0 Hz, 1H), 7.45 (m, 3H), 7.35 (s, 1H), 7.28 (m, 4H), 7.20 (m, 1H), 7.04 (d, J=8.4 Hz, 1H), 6.61(m, 2H), 6.13 (s, 1H), 5.44 (d, J=9.6 Hz, 1H), 5.28 (m, 4H), 5.09 (d, J=15.2 Hz, 1H), 4.81 (q, J=15.6 Hz, 2H), 4.63 (d, J=10.0 Hz, 1H), 4.25 (d, J=15.2 Hz, 1H), 4.18 (dd, J=8.0, 6.8 Hz, 1H), 4.11 (m, 1H), 3.93 (s, 3H), 3.90 (s, 3H), 3.71 (m, 3H), 3.41 (m, 2H), 3.21 (t, J=10.4 Hz, 1H), 3.09 (dd, J=15.2, 5.6 Hz, 1H), 2.83 (m, 2H), 0.98 (m, 2H), 0.03 (s, 9H).

To a solution of compound 56 (37 mg, 0.042 mmol) in THF (2 mL) was added SUPER HYDRIDE™ (0.209 mL, 0.209 mmol) at –76° C. The reaction mixture was stirred for 1 h and quenched with cold water (1 mL) and extracted with DCM (3×10 mL). The organic layer was concentrated and treated with DCM/EtOH/water (1:2:1, 4 mL) and silica gel (1 g) for 3 days. This mixture was filtered through a sintered funnel and the silica gel was washed with DCM-MeOH (8:2, 50 mL). The filtrate was concentrated under high vacuum and purified on a 12 g silica gel column using 0-10% MeOH/DCM elution over 15 min to provide dimer IIa-04 as white solid (25.3 mg, 78% yield). MS (m+1)=737.2. $^1$H NMR (400 MHz, CDCl$_3$) ☐ 7.70 (t, J=8.0 Hz, 1H), 7.55 (s, 1H), 7.43 (m, 3H), 7.28 (m, 3H), 7.23 (m, 1H), 7.12 (d, J=8.0 Hz, 1H), 6.92 (s, 1H), 6.62 (d, J=7.2 Hz, 1H), 6.45 (s, 1H), 6.05 (s, 1H), 5.32 (m, 3H), 4.80 (m, 2H), 4.40 (d, J=15.6 Hz, 1H), 4.01 (s, 3H), 3.90 (s, 3H), 3.50 (s, 1H), 3.14 (m, 2H), 2.97 (m, 3H), 2.75 (dd, J=15.2, 5.6 Hz, 2H).

Example 11

Dimer Linker IIIc-02

Figure 12A:
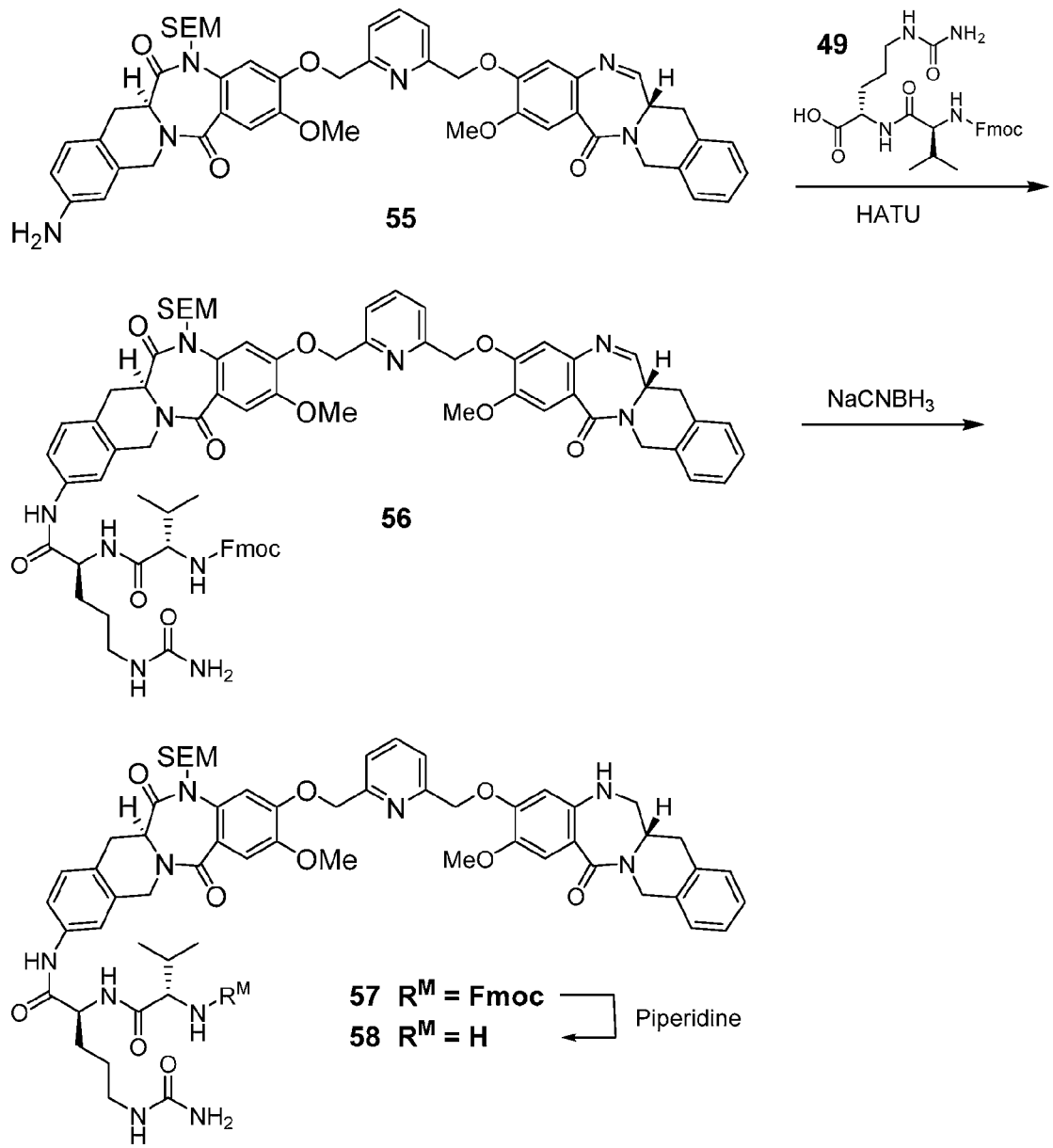
Figure 12B:
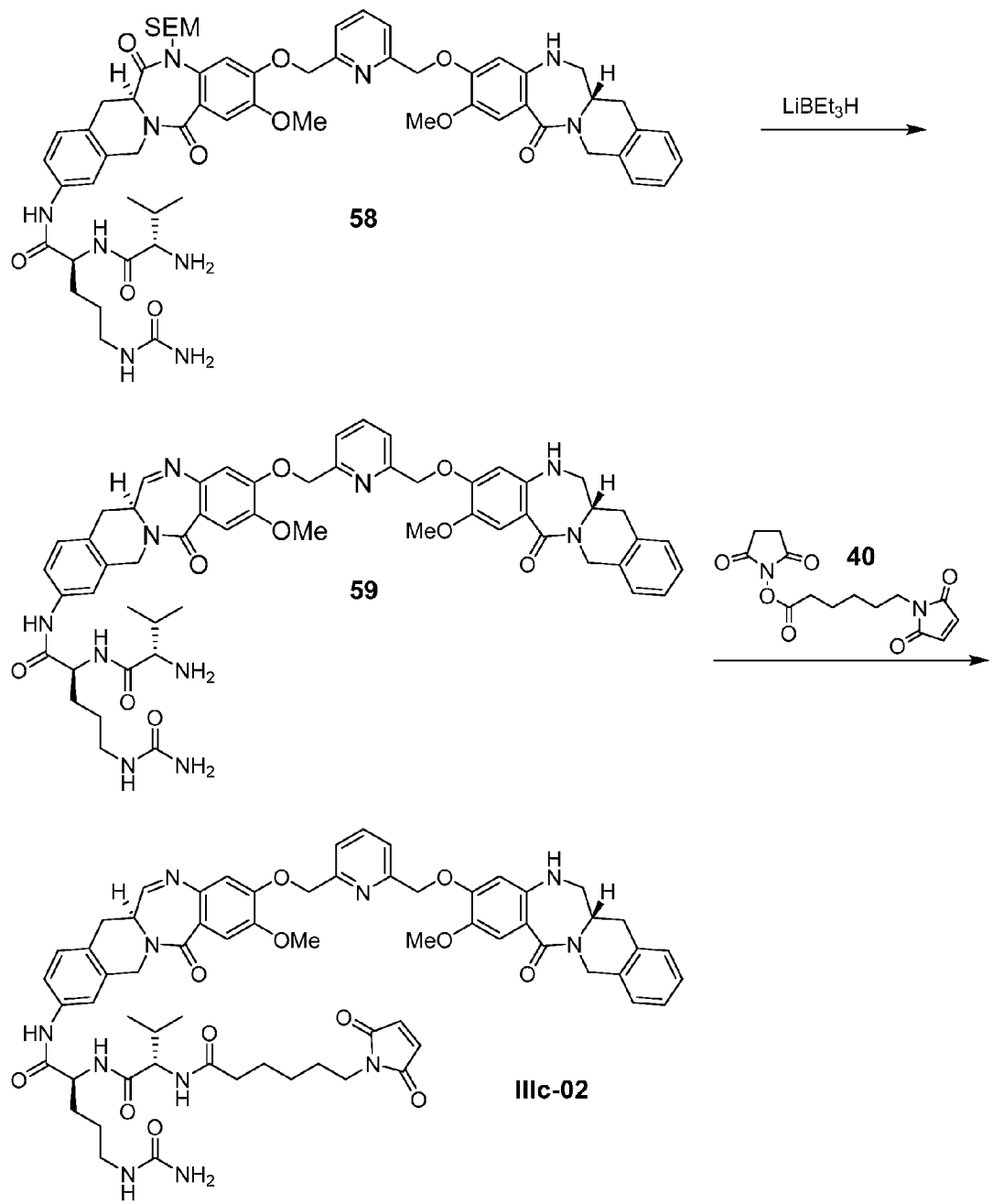

This example and FIGS. 12A and 12B relate to the synthesis of dimer-linker IIIc-02.

2,6-Lutidine (0.323 mL, 2.77 mmol) was added to a solution of compound 55 (1.22 g, 1.385 mmol), compound 49 (0.825 g, 1.662 mmol), and HATU (0.632 g, 1.662 mmol) in DMF (20 mL) at 0° C. The reaction mixture was stirred at RT for 1 h, at which point LCMS showed complete conversion to product. The reaction mixture was poured into a separatory funnel containing EtOAc (300 mL) and water (100 mL). Brine (50 mL) was added to get separation into two layers. The organic layer was concentrated and purified on an ISCO COMBIFLASH™ 120 g column, 0-30% MeOH/DCM elution over 25 min to yield compound 56 (1.13 g, 0.831 mmol, 60.0% yield) as white solid. MS (m+1)=1359.4.

Acetic acid (0.095 mL, 1.662 mmol) was added to a solution of compound 56 (1.13 g, 0.831 mmol) in THF (30 mL), followed by NaCNBH3 (0.104 g, 1.662 mmol) in MeOH (3 mL) at 0° C. The reaction mixture was stirred at RT for 1 h, diluted with EtOAc (200 mL), and washed with sat NaHCO$_3$ solution (50 mL) and brine (50 mL). The organic layer was concentrated and purified on an ISCO COMBIFLASH™ 80 g column, 0-20% MeOH/DCM eluent over 25 min to yield compound 57 (1 g, 0.734 mmol, 88% yield) as white solid. MS (m+Na)=1384.2

Piperidine (2 mL, 20.20 mmol) was added to a solution of compound 57 (1 g, 0.734 mmol) in THF (20 mL). The reaction mixture was stirred at RT for 1 h. The reaction mixture was concentrated and purified on an ISCO CoM-BIFLASH™ 40 g column, 0-50% MeOH/DCM eluent over 25 min to provide compound 58 (0.7 g, 0.614 mmol, 84% yield) as white solid. MS (m+1)=1139.4.

To a solution of compound 58 (0.5 g, 0.439 mmol) in THF (10 mL) at –76° C. was added SUPER HYDRIDE™ (4.39 mL, 4.39 mmol). The reaction mixture was stirred for 45 min. The reaction was quenched with cold water (1 mL) and concentrated. The resulting residue was treated with DCM/EtOH/water (1:2:1, 8 mL) and silica gel (2 g) for 2 days. This mixture was filtered through a sintered funnel and the silica gel was washed with DCM-MeOH (8:2, 200 mL). The filtrate was concentrated under high vacuum and purified on an ISCO 80 g silica gel (Gold) column using MeOH/DCM over 40 min to provide compound 59 (0.4 g, 0.403 mmol, 92% yield) as white solid. MS (m+1)=993.4

To a solution of compound 59 (24 mg, 0.024 mmol) and compound 84 (14.90 mg, 0.048 mmol) in DMSO (2 mL) was added DIPEA (8.44 μL, 0.048 mmol). The reaction mixture was stirred at RT for 1 h. The reaction mixture was purified by R- HPLC using) (Bridge prep OBD C18, 5 μm column (30×250 mm) and 5-60% acetonitrile/water (0.05% formic acid) over 30 min. A fraction collected at 20.3 min was filtered through a basic resin (PL-HCO$_3$ MP -Resin 1.8 mmol/g; Agilent Part #PL3540-#603) and washed with acetonitrile (5 mL). Lyophilization provided dimer-linker IIIc-02 (7.6 mg, 6.21 μmol, 25.7% yield) as white solid. MS (m+1)=1186.5.

Example 12

Dimer-Linkers IIIb-03 and IIIb-03'

Figure 13:
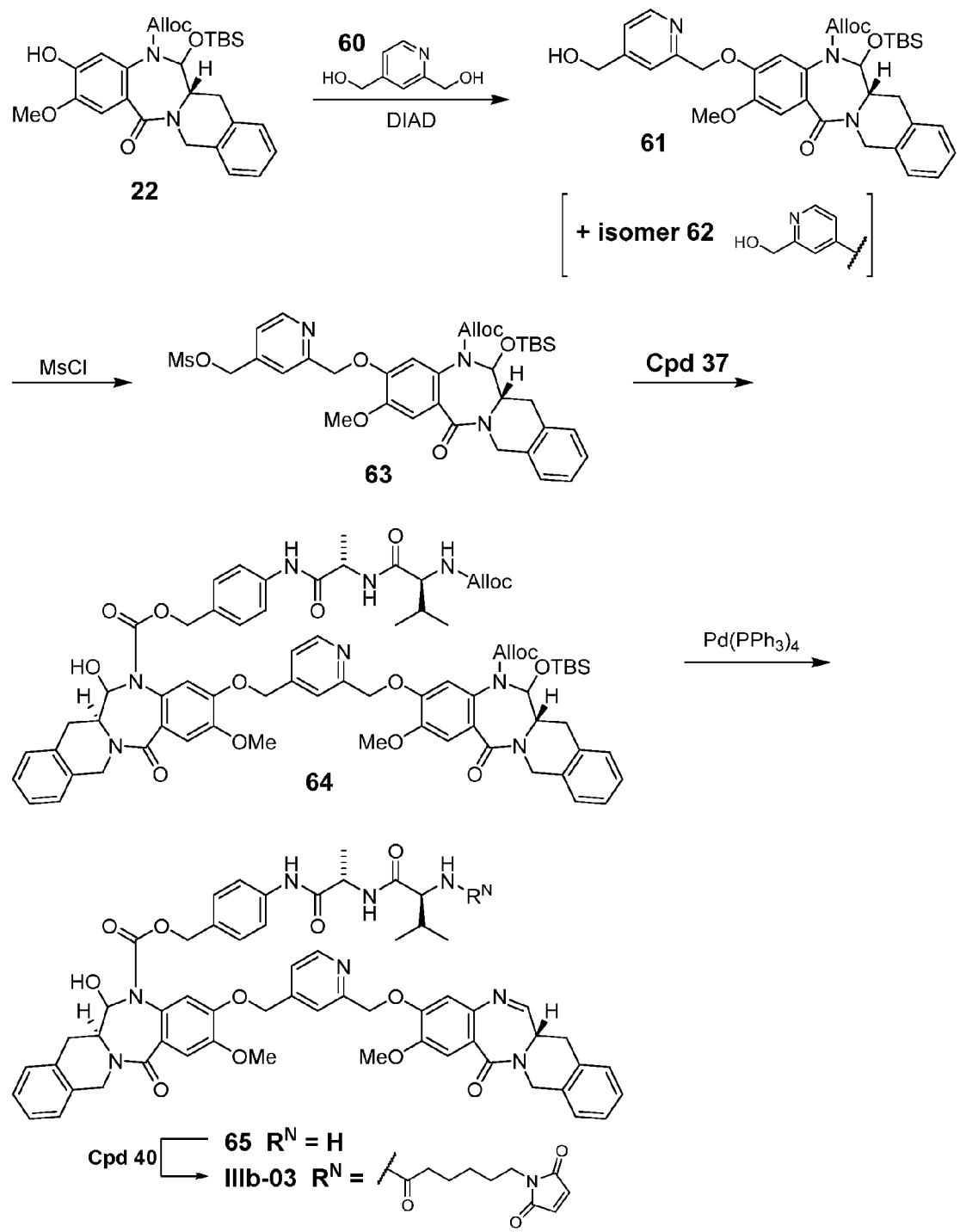

This example and FIG. 13 relate to the synthesis of dimer-linker IIIb-03.

To pyridine-2,4-diyldimethanol (80 mg, 0.572 mmol) in THF (2 mL) was added phenol 22 (100 mg, 0.191 mmol), polymer-bound triphenylphosphine (200 mg, 0.629 mmol) and diisopropyl azodicarboxylate (DIAD, 0.122 mL, 0.629 mmol). The reaction stirred 12 h at 25° C. and the mixture was filtered. The solvent was removed and the material purified by silica gel chromatography, eluting with a gradient from 20-100% acetone in DCM to afford compounds 61 (70 mg, 56.9% yield) LCMS M+H=646.45 and 62 (50 mg, 40.6% yield) LCMS M+H=646.40.

To compound 61 (67 mg, 0.104 mmol) and TEA (0.036 mL, 0.259 mmol) in DCM (2 mL) was added methanesulfonyl chloride (MsCl, 0.019 mL, 0.239 mmol) at 0° C. The reaction was stirred at 0° C. for 1 h and quenched with water. The mixture was extracted with DCM, washed with cold aq. HCl (0.05 N), brine, dried over $Na_2SO_4$, and concentrated to give compound 63 as an orange oil. The material was purified on silica gel chromatography, eluting with a gradient from 20-100% ethyl acetate in hexane to afford purified compound 63 (40 mg, 30% yield) LCMS M+H=724.10.

To compound 63 (40 mg, 0.055 mmol) in DMF (0.1 mL) was added $Cs_2CO_3$ (40 mg, 0.123 mmol) and compound 37 (40.3 mg, 0.055 mmol). The reaction was stirred 4 h at 25° C., and the material was purified by HPLC Procedure A. The sample was divided into two equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and water was removed by lyophilization to afford compound 64 as a white powder (16.0 mg, 65% yield). LCMS M+H=1357.65.

Compound 64 (15 mg, 0.011 mmol) was dissolved in a solution of pyrrolidine in DCM (0.042 M, 0.658 mL, 0.028 mmol) and $Pd(PPh_3)_4$ (0.766 mg, 0.663 μmol) was added. The mixture was stirred for 2.5 h at RT and the reaction solvent was removed under $N_2$. The remaining material was diluted with 1.5 mL DMF and purified by HPLC Procedure A. The sample was divided into 2 equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and the water was removed by lyophilization to afford amine 65 as a white powder (11.5 mg, 98% yield). LCMS M+Na=1080.

Amine 65 (11.5 mg, 10.88 μmol) was dissolved in a solution of DIPEA in DMF (0.261 ml, 0.013 mmol) and compound 40 (6.71 mg, 0.022 mmol) was added. The mixture was stirred for 20 h, diluted with DMF, and purified by preparative HPLC as described in the preceding paragraph. The sample was divided into 2 equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and the water was removed by lyophilization to afford dimer-linker IIIb-03 as a white powder (3 mg, 2.231 μmol, 20.51% yield). LCMS M+H=1250.60.

Dimer-llinker IIIb-03' can be prepared analogously from compound 62.

Example 13

Dimer IIa-06

Figure 14:
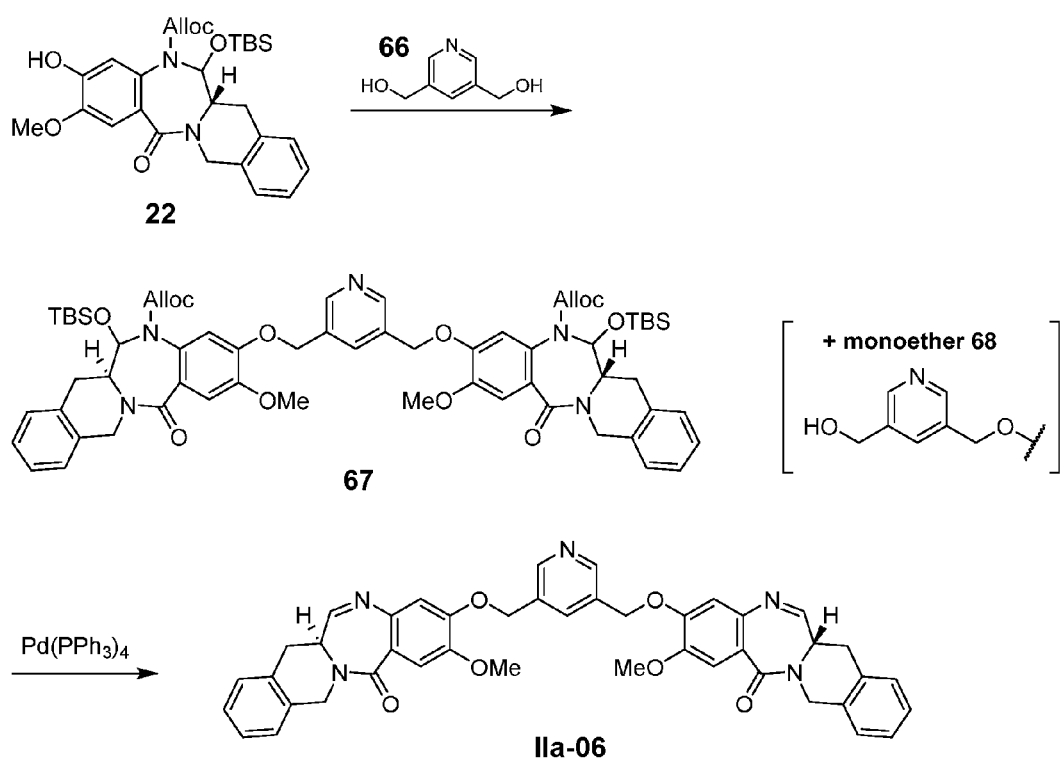

This example and FIG. 14 relate to the preparation of dimer IIa-06.

To pyridine-3,5-diyldimethanol 66 (26.5 mg, 0.191 mmol) in THF (2 mL) was added phenol 22 (100 mg, 0.191 mmol), polymer-bound triphenylphosphine (200 mg, 0.629 mmol) and DIAD (0.122 mL, 0.629 mmol). The reaction stirred 12 hr at 25° C. and the mixture was filtered. The solvent was removed and the material purified by silica gel chromatography, eluting with a gradient from 20-100% acetone in DCM to afford dimer 67 (55 mg, 15.02% yield) LCMS M+Na=1174.65 and compound 68 (38 mg, 31% yield) LCMS M+H=646.30.

Dimer 67 (15 mg, 0.013 mmol) was dissolved in a solution of pyrrolidine in DCM (0.775 mL, 0.033 mmol) and $Pd(PPh_3)_4$ (1 mg, 0.865 μmol) was added. The mixture was stirred for 30 min and partitioned between DCM and saturated $NH_4Cl$. The phases were separated and the aqueous fraction was extracted twice more with DCM. The combined organic phases were dried over $Na_2SO_4$, filtered and evaporated to a residue, which was purified by HPLC Procedure A. The sample was divided into two equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and water was removed by lyophilization to afford dimer IIa-06 as a white powder (2 mg, 20.28% yield). LCMS M+H=721.30.

Example 14

Dimer-Linker IIIb-04

Figure 15:
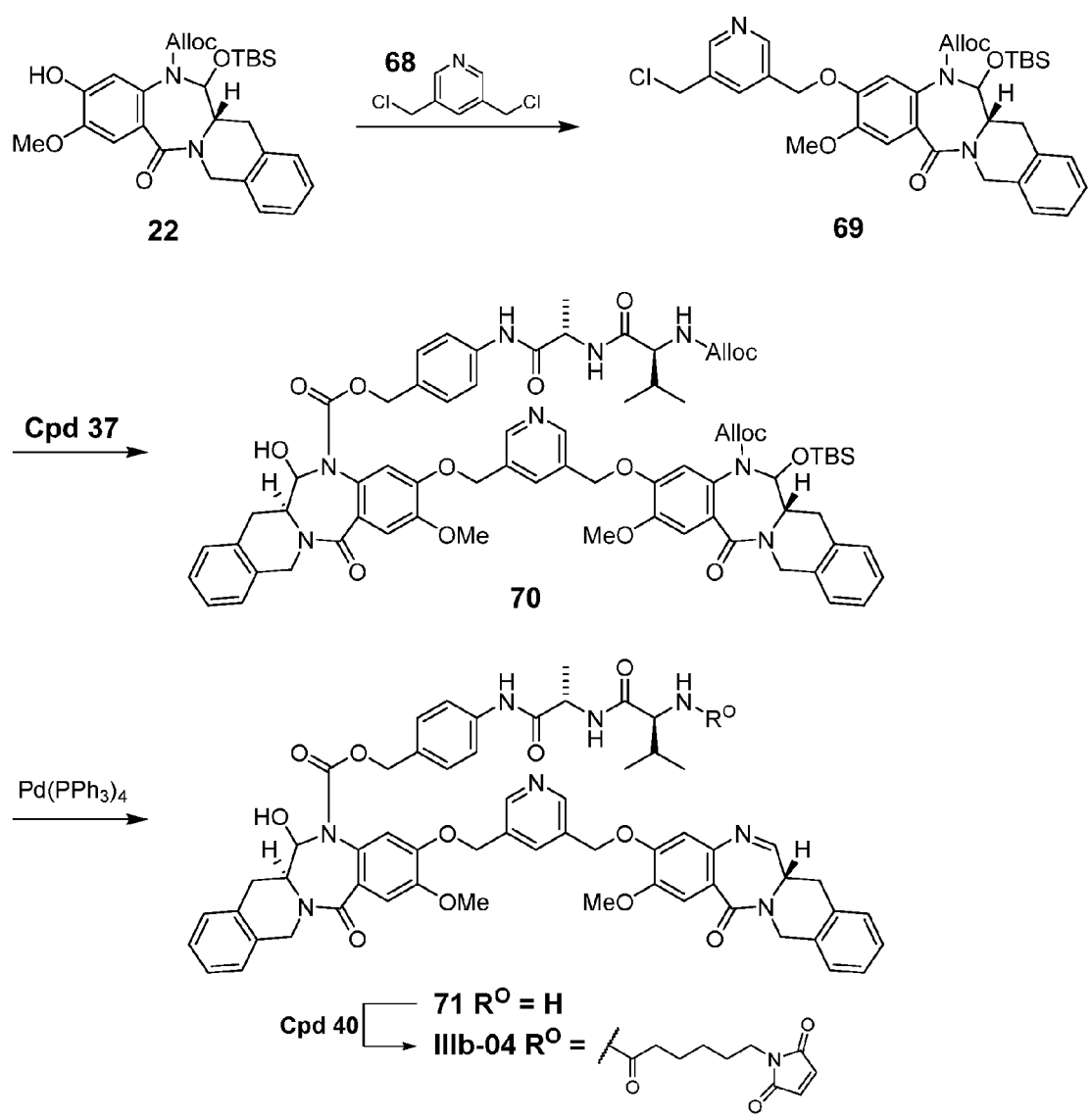

This example and FIG. 15 relate to the synthesis of dimer-linker IIIb-04.

A suspension of phenol 22 (200 mg, 0.381 mmol), 3,5-bis(chloromethyl)pyridine hydrochloride (250 mg, 1.176 mmol) and $Cs_2CO_3$ (800 mg, 2.455 mmol) in DIIIF (1.0 mL) was stirred at 25° C. for 16 h. The solvent was removed under nitrogen. The residue was dry loaded on to CELITE™ and purified by silica gel chromatography, eluting with a gradient of 2-10% MeOH in DCM to afford dimer 69 (120 mg, 47% yield). LCMS M+Na=687.05.

To compound 37 (150 mg, 0.206 mmol) in DMF (1.0 mL) was added $Cs_2CO_3$ (100 mg, 0.307 mmol) and dimer 69 (150 mg, 0.206 mmol). The reaction was stirred 12 h at 25° C., and the material was purified by HPLC Procedure A. The sample was divided into two equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and the water was removed by lyophilization to afford compound 70 as a white powder (42 mg, 15.65% yield). LCMS M+H=1357.65.

Compound 70 (40 mg, 0.029 mmol) was dissolved in a solution of pyrrolidine in DCM (0.042 M, 1.8 mL, 0.074 mmol) and Pd(PPh$_3$)$_4$ (2.0 mg, 1.768 μmol) was added. The mixture was stirred for 2.5 h at RT and the reaction solvent was removed under N$_2$. The material was diluted with 1.5 ml DMF and purified by HPLC Procedure A. The sample was divided into 2 equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and the water was removed by lyophilization to afford amine 71 as a white powder (15 mg, 43% yield). LCMS M+Na=1080.

Amine 71 (15 mg, 10.88 μmol) was dissolved in a solution of DIPEA in DMF (0.615 mL, 0.031 mmol) and compound 40 (25 mg, 0.024 mmol) was added. The mixture was stirred for 20 h, diluted with DMF and purified by HPLC Procedure A. The sample was divided into 2 equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and the water was removed by lyophilization to afford dimer-linker IIIb-04 as a white powder (10 mg, 30% yield). LCMS M+H=1250.60.

Example 15

Dimer IIa-08

Figure 16:
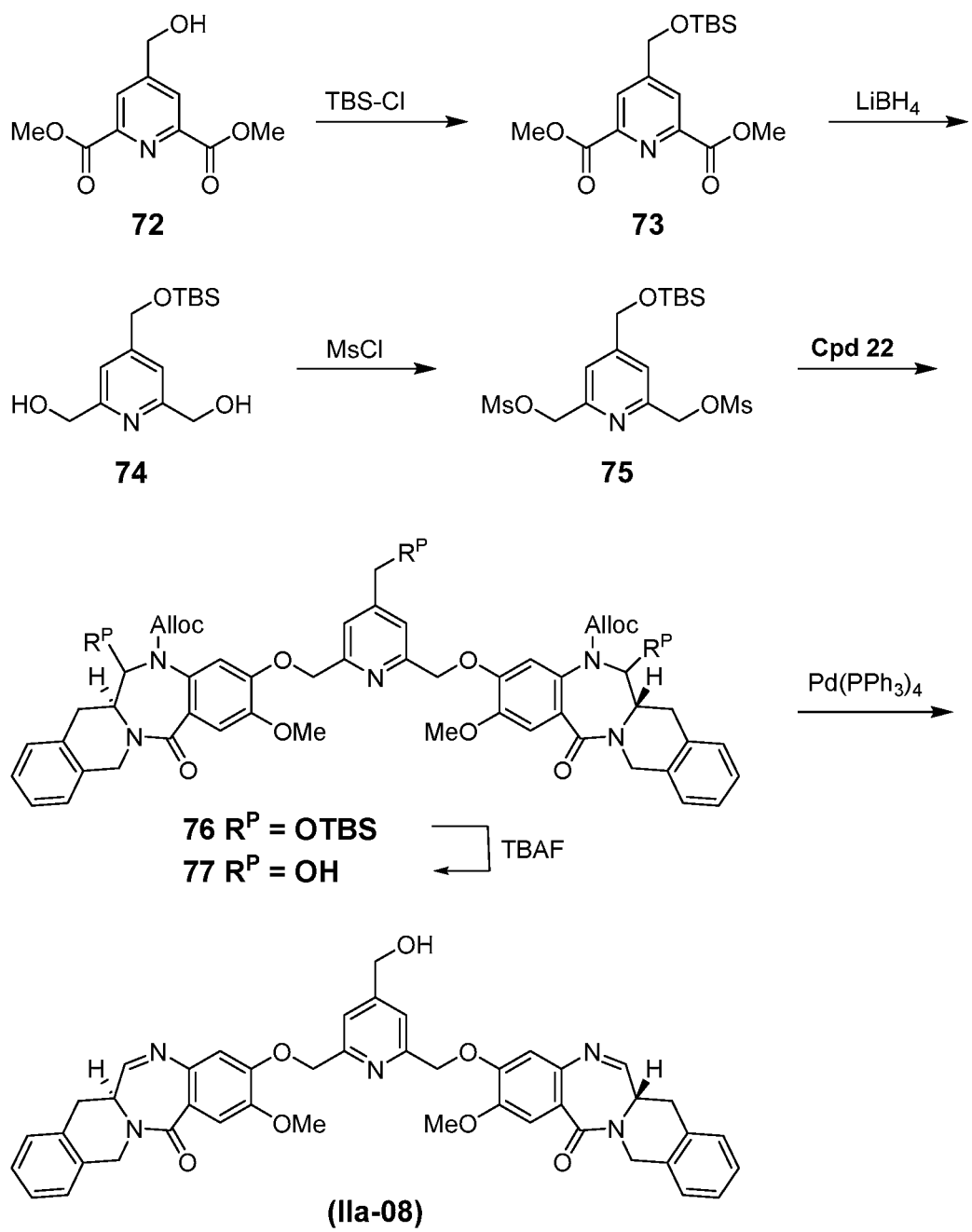

This example and FIG. 16 relate to the preparation of dimer IIa-08.

To dimethyl 4-(hydroxymethyl)pyridine-2,6-dicarboxylate 72 (200 mg, 0.888 mmol) in DMF (0.888 ml) was added imidazole (100 mg, 1.469 mmol) and t-butyldimethyl-silyl chloride (TBS-Cl, 4 ml, 1.149 mmol). The reaction was stirred at 25° C. overnight. The solvent was removed under nitrogen and the material was purified on silica gel chromatography, eluting with a gradient from 0-50% ethyl acetate in hexane to afford compound 73 (290mg, 91% yield). LCMS M+H=340.50.

To compound 73 (14 g, 0.412 mmol) in ethanol (2 mL) was added LiBH$_4$ (0.054 g, 2.475 mmol). The reaction was stirred for 5 h at 25° C. The reaction was quenched with acetic (0.189 mL, 3.30 mmol) and stirred 10 min. The solvent was removed and the material was dry loaded onto CELITE™. The material was purified BY silica gel chromatography, eluting with a gradient from 2-10% methanol in DCM to afford compound 74 (120 mg, 98% yield). LCMS M+H=284.50.

To a suspension of compound 74 (100 mg, 0.353 mmol), TEA (0.123 mL, 0.882 mmol) in DCM (2 mL) was added MsCl (0.063 mL, 0.811 mmol) at 0° C. The reaction was stirred at 0° C. for 1 h. The reaction was then quenched with water, extracted with DCM, washed with cold aq. HCl (0.05 N), brine, and dried over Na$_2$SO$_4$. The solvent was removed to give the mesylate 75 as an orange oil. The material was purified on silica gel chromatography, eluting with a gradient from 20-100% ethyl acetate in hexane to afford mesylate 75 (155 mg, 98% yield). LCMS M+H=440.30.

To mesylate 75 (25 mg, 0.057 mmol) in DMF (0.3 mL) was added Cs$_2$CO$_3$ (85 mg, 0.261 mmol) and phenol 22 (90 mg, 0.171 mmol). The reaction was stirred at 25° C. for 1 h. The material was purified on silica gel chromatography, eluting with a gradient from 30-100% acetone in DCM to afford dimer 76 (70 mg, 93% yield). LCMS M+H=1296.65.

To dimer 76 (40 mg, 0.031 mmol) in THF (0.3 mL) was added tetrabutyl ammonium fluoride (TBAF, 0.037 mL, 0.037 mmol). The reaction was complete in 30 min and quenched with saturated (NH$_4$)$_2$SO$_4$. The mixture was extracted with ethyl acetate and dried over Na$_2$SO$_4$. The solvent was removed, diluted with DMF, and purified by HPLC Procedure A. The fractions containing the product were combined and passed through a PL-HCO3- MP SPE 500 mg/6 mL cartridge, eluting with acetonitrile to afford a solution of the product as a free base. The bulk of the organic solvent was removed by rotary evaporation and water was removed by lyophilization to afford dimer 77 as a white powder (14 mg, 47% yield). LCMS M+H=954.35.

Dimer 77 (14 mg, 0.012 mmol) was dissolved in a solution of pyrrolidine in DCM (0.042 M, 0.705 ml, 0.030 mmol) and Pd(PPh$_3$)$_4$ (1.0 mg, 0.9 μmol) was added. The mixture was stirred for 1 h and partitioned between DCM and saturated NH$_4$Cl. The phases were separated and the aqueous fraction extracted twice more with DCM. The combined organic phases were dried over Na$_2$SO$_4$, filtered and evaporated to a residue, which was purified by HPLC Procedure A. The sample was divided into two equal injections. The fractions containing the product peak were combined and passed through a PL-HCO3- MP SPE 500 mg/6 mL cartridge, eluting with acetonitrile to afford a solution of the product as a free base.

The bulk of the organic solvent was removed by rotary evaporation and water was removed by lyophilization to afford dimer IIa-08 as a white powder (5.0 mg, 54% yield). LCMS M+H=750.30.

Example 16

Dimer-Linker IIIb-05

Figure 17:
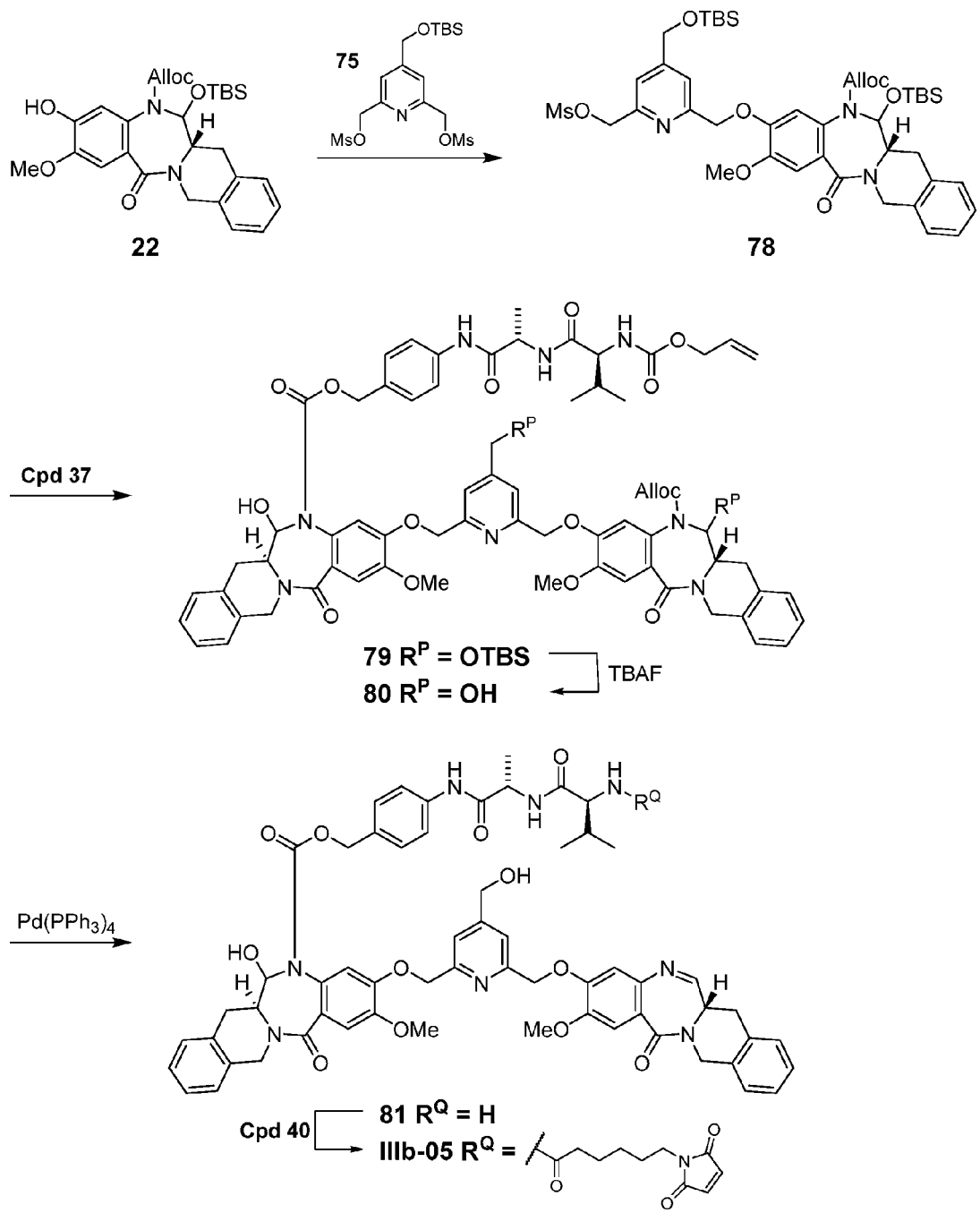

This example and FIG. 17 relate to the preparation of dimer-linker IIIb-05.

To compound 75 (113 mg, 0.257 mmol) in DMF (0.2 mL) was added phenol 22 (45 mg, 0.086 mmol) and Cs$_2$CO$_3$ (60 mg, 0.184 mmol). The reaction was stirred at 25° C. for 1 h. The material was purified by silica gel chromatography, eluting with a gradient from 30-100% ethyl acetate in DCM to afford dimer 78 (40 mg, 30.6% yield). LCMS M+H=868.60.

To dimer 78 (39 mg, 0.045 mmol) in DMF (0.2 mL) was added Cs$_2$CO$_3$ (40 mg, 0.123 mmol) and compound 37 (40 mg, 0.055 mmol). The reaction was stirred 4 h at 25° C., and the material was purified by HPLC Procedure A. The sample was divided into two equal injections. The fractions containing the product were combined and passed through a PL-HCO3- MP SPE 500 mg/6 mL cartridge, eluting with acetonitrile to afford a solution of the product as a free base. The bulk of the organic solvent was removed by rotary evaporation and water was removed by lyophilization to afford compound 79 as a white powder (60.0 mg, 89% yield). LCMS M+H=1501.85.

To dimer 79 (60 mg, 0.040 mmol) in THF (0.4 mL) was added TBAF (0.04 mL, 0.040 mmol). The reaction was complete in 30 min and quenched with saturated NH$_4$Cl. The mixture was extracted with ethyl acetate and dried over Na$_2$SO$_4$. The solvent was removed, diluted with DMF, and purified by HPLC Procedure A. The fractions containing the product were combined and passed through a PL-HCO3- MP SPE 500 mg/6 mL cartridge, eluting with acetonitrile to afford a solution of the product as a free base. The bulk of the organic solvent was removed by rotary evaporation and water was removed by lyophilization to afford dimer 80 as a white powder (13 mg, 20% yield). LCMS M+H=1273.55.

Compound 80 (13 mg, 10.21 µmol) was dissolved in a solution of pyrrolidine in DCM (0.042 M, 0.608 mL, 0.026 mmol) and Pd(PPh$_3$)$_4$ (0.708 mg, 0.613 µmol) was added. The mixture was stirred for 2.5 h at RT. The reaction solvent was removed under N$_2$. The material was diluted with 1.5 ml DMF and purified by HPLC Procedure A. The sample was divided into 2 equal injections. The fractions containing the product were combined and passed through a PL-HCO3- MP SPE 500 mg/6 mL cartridge, eluting with acetonitrile to afford a solution of the product as a free base. The bulk of the organic solvent was removed by rotary evaporation and water was removed by lyophilization to afford amine 81 as a white powder (11 mg, 90% yield). LCMS M+H=1087.50.

Amine 81 (11 mg, 10.12 µmol) was dissolved in a solution of DIPEA in DMF (0.243 mL, 0.012 mmol) and compound 40 (6.24 mg, 0.020 mmol) was added. The mixture was stirred for 20 h and was diluted with DMF and purified by HPLC Procedure A. The sample was divided into 2 equal injections. The fractions containing product were combined and passed through a PL-HCO3- MP SPE 500 mg/6 mL cartridge, eluting with acetonitrile to afford a solution of the product as a free base. The bulk of the organic solvent was removed by rotary evaporation and water was removed by lyophilization to afford dimer-linker IIIb-04 as a white powder (6 mg, 42% yield). LCMS M+H=1281.60.

Example 17

Dimers IIa-07 and IIa-09

Figure 18:
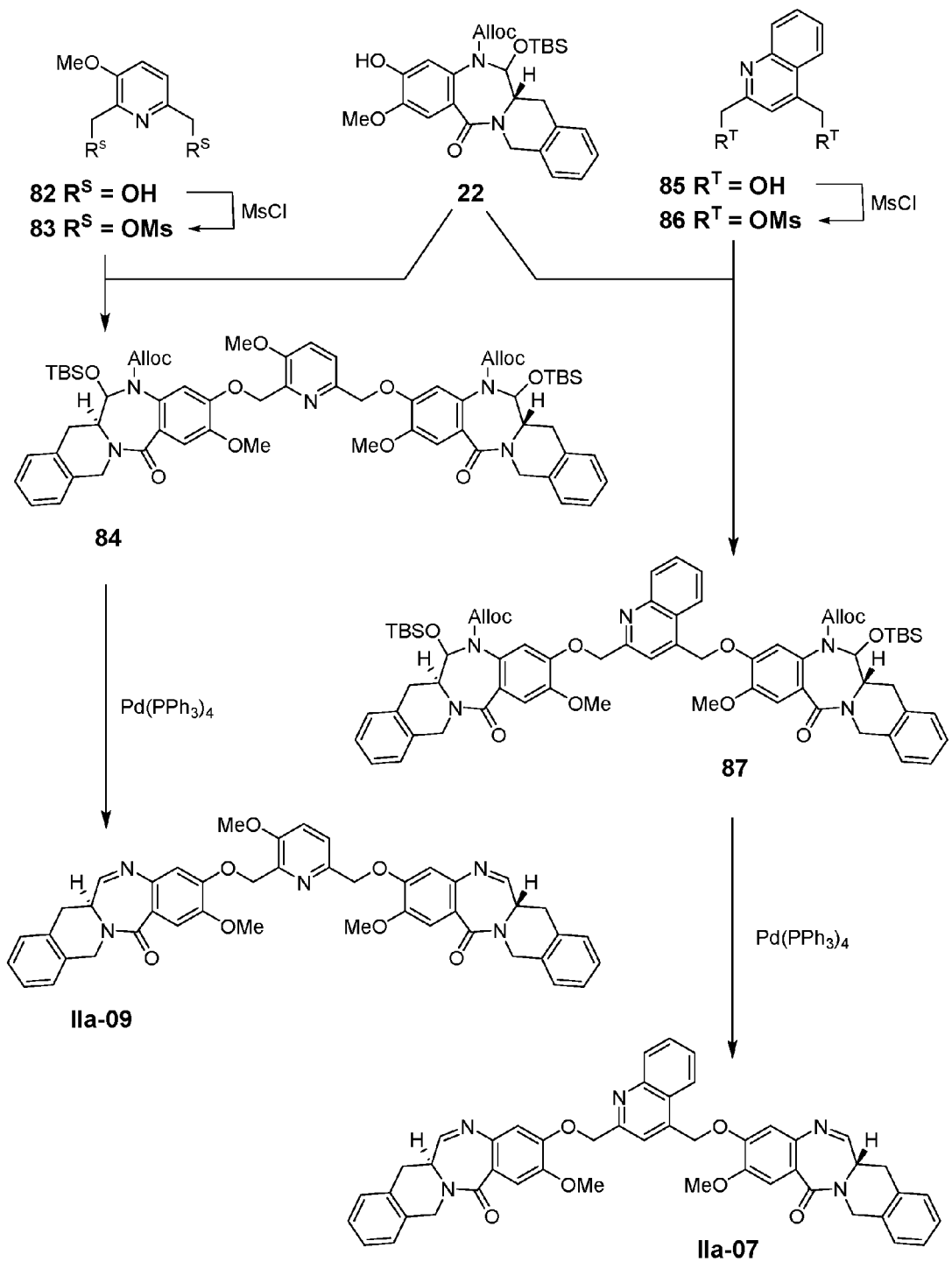

This example and FIG. 18 relates to the preparation of dimers IIa-07 and IIa-09.

To a suspension of (3-methoxypyridine-2,6-diyl)dimethanol 82 (90 mg, 0.532 mmol), NEt$_3$ (0.185 mL, 1.330 mmol) in DCM (3 mL) was added MsCl (0.095 mL, 1.224 mmol) at 0° C. The reaction was stirred at 0° C. for 1 h. The reaction was quenched with water, extracted with DCM, washed with cold aq. HCl (0.05 N), brine, dried over Na$_2$SO$_4$, and concentrated to give the crude mesylate as an orange oil. The material was purified by chromatography, eluting with a gradient from 20-100% ethyl acetate in hexane to afford compound 83 (87 mg, 45% yield). LCMS M+Na=347.75.

A suspension of phenol 22 (97 mg, 0.184 mmol), compound 83 (20 mg, 0.061 mmol) and Cs$_2$CO$_3$ (60 mg, 0.184 mmol) in DMF (0.3 ml) was stirred at 25° C. for 3 h. The solvent was removed under nitrogen. The material was purified by silica gel chromatography, eluting with a gradient from 2-10% methanol in DCM to afford dimer 84 (67 mg, 77% yield). LCMS M+H=1183.02.

Dimer 84 (20 mg, 0.017 mmol) was dissolved in a solution of pyrrolidine in DCM (0.042 M, 1.0 ml, 0.042 mmol) and Pd(PPh$_3$)$_4$ (1.0 mg, 1.0 µmol) was added. The mixture was stirred for 30 min and partitioned between DCM and saturated NH$_4$Cl. The phases were separated and the aqueous fraction was extracted twice more with DCM. The combined organic phases were dried over Na$_2$SO$_4$, filtered and evaporated to a residue which was purified by HPLC Procedure A. The sample was divided into two equal injections. The fractions containing product were combined and passed through a PL-HCO3- MP SPE 500 mg/6 mL cartridge, eluting with acetonitrile to afford a solution of the product as a free base. The bulk of the organic solvent was removed by rotary evaporation and water was removed by lyophilization to afford dimer IIa-09 as a white powder (3.0 mg, 22% yield). LCMS M+H=750.30.

To a suspension of quinoline-2,4-diyldimethanol 85 (100 mg, 0.529 mmol), NEt$_3$ (0.185 mL, 1.330 mmol) in DCM (3 mL) was added MsCl (0.095 mL, 1.224 mmol) at 0° C. The reaction was stirred at 0° C. for 1 h. The reaction was quenched with water, extracted with DCM, washed with cold aq. HCl (0.05 N), brine, dried over Na$_2$SO$_4$, and concentrated to give the crude mesylate as an orange oil. The material was purified by chromatography, eluting with a gradient from 20-100% ethyl acetate in hexane to afford compound 86 (80 mg, 44% yield). LCMS M+Na=345.80.

A suspension of phenol 22 (182 mg, 0.347 mmol), compound 86 (40 mg, 0.116 mmol) and Cs$_2$CO$_3$ (113 mg, 0.347 mmol) in DMF (0.3 ml) was stirred at 25° C. for 3 h. The solvent was removed under nitrogen. The material was purified by silica gel chromatography, eluting with a gradient from 30-100% acetone in DCM to afford dimer 87 (95 mg, 68% yield). LCMS M+H=1202.60.

Dimer 87 (20 mg, 0.017 mmol) was dissolved in a solution of pyrrolidine in DCM (0.042 M, 0.4 ml, 0.017 mmol) and Pd(PPh$_3$)$_4$ (1.0 mg, 1.0 µmol) was added. The mixture was stirred for 30 min and partitioned between DCM and saturated NH$_4$Cl. The phases were separated and the aqueous fraction extracted twice more with DCM. The combined organic phases were dried over Na$_2$SO$_4$, filtered and evaporated to a residue, which was purified by HPLC Procedure A. The sample was divided into two equal injections. The fractions containing the product peak were combined and passed through a PL-HCO3- MP SPE 500 mg/6 mL cartridge, eluting with acetonitrile to afford a solution of the product as a free base. The bulk of the organic solvent was removed by rotary evaporation and water was removed by lyophilization to afford dimer IIa-07 as a white powder (8.0 mg, 59% yield). LCMS M+H=770.30.

Example 18

Additional Intermediates

Figure 19A:
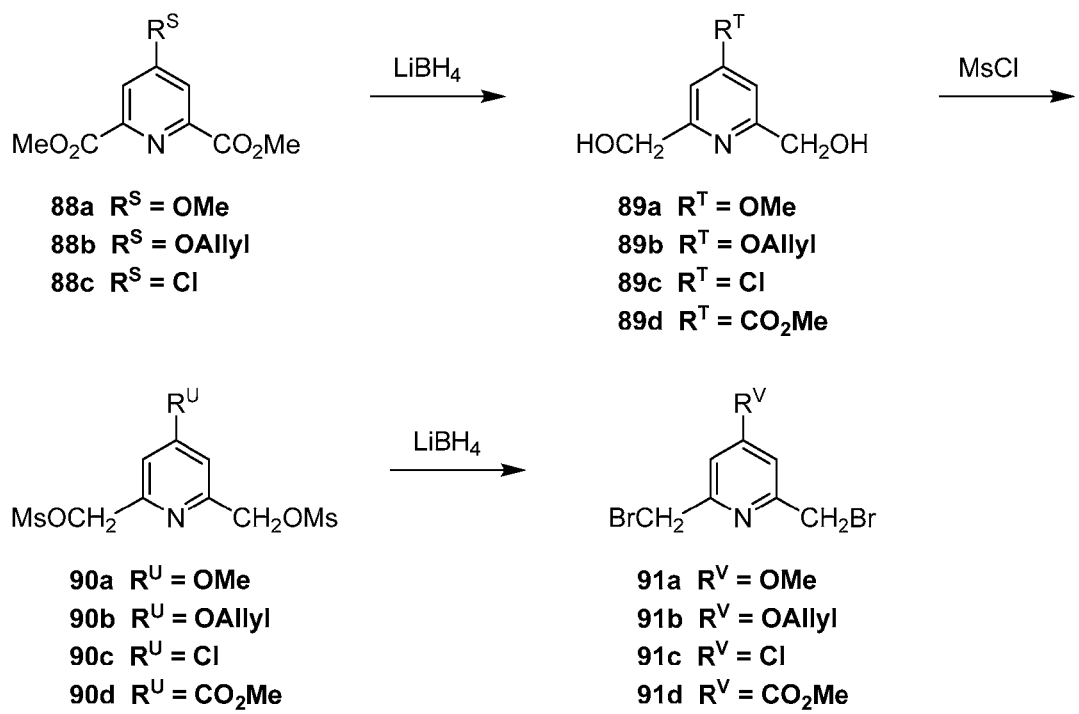

Dibromides 91a-d, useful for the synthesis of dimers of this invention, were synthesized according to the scheme of FIG. 19A. Starting materials 88a and 88b were prepared as described in Synth. Commun. 1999, 3719. Starting material 88c was obtained from Arkpharma. Starting material 89d was prepared as described in WO 2012/153253.

The following procedure for the preparation of intermediate 88a is representative.

Methyl ether 88a (0.45 g, 2.0 mmol) was suspended in ethanol (20 mL) and lithium borohydride was added. The mixture was stirred at ambient temperature for 5 h and then quenched by the addition of acetic acid. The mixture was evaporated and purified by silica gel chromatography with a gradient from 0-20% methanol in DCM to afford diol 89a (210 mg, 62% yield). $^1$H NMR (400 MHz, DMSO-d$_6$) δ 6.87 (s, 2H), 5.33 (br t, J=5.5 Hz, 2H), 4.47 (br d, J=4.9 Hz, 4H), 3.84 (s, 3H).

Diol 89a (0.21 g, 1.24 mmol and triethylamine (0.52 mL, 3.72 mmol) were suspended in DCM (6.2 mL) and cooled on an ice/water bath. To this mixture was added MsCl (0.22 mL, 2.85 mmol). The reaction mixture was allowed to procede for 2 h at the same temperature, then was quenched by the addition of water and extracted with DCM. The organic phases were washed with 0.1N HCl, followed by brine and then dried over sodium sulfate. After filtration, the solvent was evaporated under reduced pressure to afford the crude mesylate 90a (0.4 g, 100% yield assumed)which was used in the subsequent step without further purification. LCMS M+H=325.85.

Mesylate 90a (0.44 g, 1.35 mmol) was dissolved in DMF (2.7 mL) and sodium bromide (696 mg, 6.76 mmol) was added. The mixture was stirred for 3h at which point it was diluted with water and the resultant solids were collected by filtration and dried under vaccuum to afford dibromide 91a (0.155g, 39% yield). $^1$H NMR (400 MHz, CHLOROFORM-d) δ 6.92 (s, 2H), 4.51 (s, 4H), 3.91 (s, 3H). LCMS M+H=293.70.

Dibromides 91b-d were synthesized analogously:
91b: LCMS M+H=319.70.
91c: $^1$H NMR (400 MHz, CHLOROFORM-d) δ 7.42 (s, 2H), 4.51 (s, 4H).
91d: $^1$H NMR (400 MHz, CHLOROFORM-d) δ 7.95 (s, 2H), 4.61 (s, 4H), 4.06-3.94 (m, 3H).

Example 19

Dimers IIa-10, IIa-11, IIa-12, IIa-13, and IIa-14.

Figure 19B:
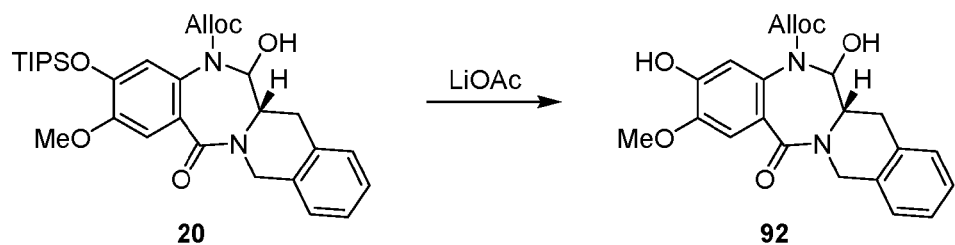

Compound 20 was converted to compound 92 by treatment with LiOAc as shown in FIG. 19B. Compound 92 was coupled with dibromides 91a-d to provide protected dimers, which were then deprotected with Pd(PPh$_3$)$_4$ to yield dimers IIa-10 through IIa-14, analogously following the procedures of Example 5 and the scheme of FIG. 6.

(IIa-10): LCMS M+H=750.05.
(IIa-11): LCMS M+H=736 (obtained by loss of the allyl group in the deprotection step leading to dimer IIa-12).
(IIa-12): LCMS M+H=776.05.
(IIa-13): LCMS M+H=754.00.
(IIa-14): LCMS M+H=778.05.

Dimers (IIa-10) through (IIa-14) differ in the nature of the bridging moiety, as summarized below:

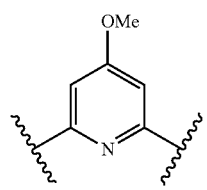
IIa-10

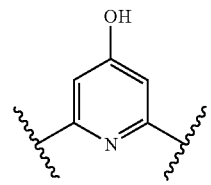
IIa-11

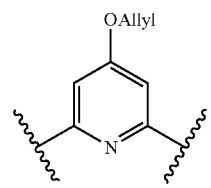
IIa-12

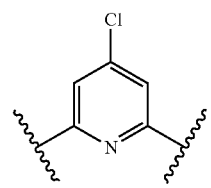
IIa-13

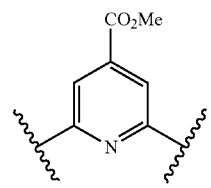
IIa-14

Example 20

Dimer-Linkers IIIb-06 and IIIb-07

Dimer-linkers IIIb-06 and IIIb-07 were prepared from compound 22 and dibromides 91a and 91b, respectively, analogously following the procedures of Example 14 and the scheme of FIG. 15.

(IIIb-06): LCMS M+Na=1302.05.
(IIIb-07): LCMS M+H=1267.

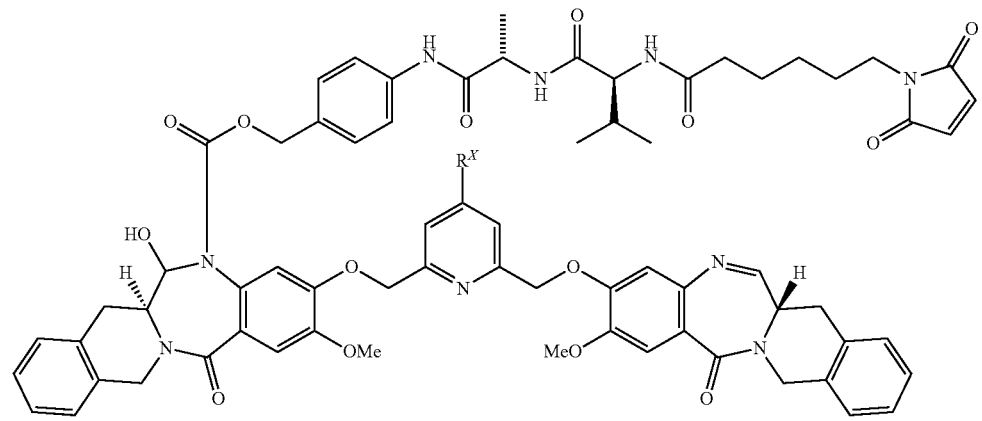

(IIIb-06) R$^X$ = OMe
(IIIb-07) R$^X$ = OH

Example 21

Dimer-Linkers IIIb-08, IIIb-08a, IIIb-08b, and IIIb-08c

This example relates to the preparation of dimer-linkers having a poly(ethylene glycol) (PEG) moiety in the linker. The presence of the PEG moiety can improve the solubility of the dimer-linker during conjugation in an aqueous medium.

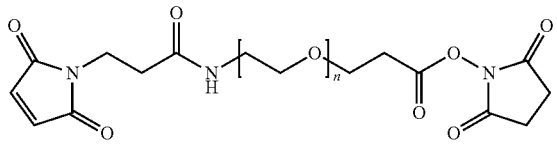

32 n = 8
32a n = 6
32b n = 4
32c n = 2

Maleimide compounds 32 and 32a-b (all available from Quanta Biodesign) were coupled to amine 39 (Example 6 and FIG. 7B) to prepare dimer-linkers IIIb-08, IIIb-08a, IIIb-08b, and IIIb-08c, respectively:

IIIb-08: LCMS (M+2H)/2=816.55.
IIIb-08a: LCMS (M+2H)/2=772.50.
IIIb-08b: LCMS (M+2H)/2=728.40.
IIIb-08c: LCMS M+Na=1390.05.

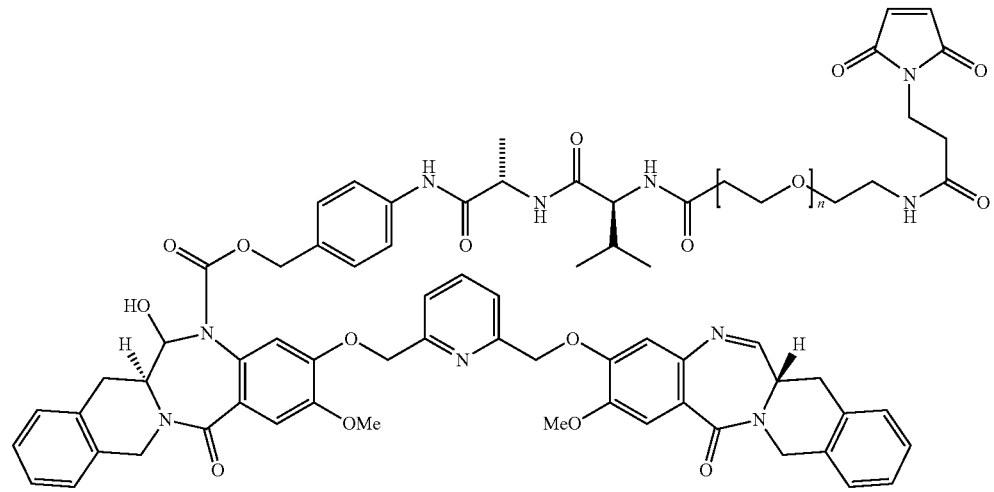

IIIb-08 n = 8
IIIb-08a n = 6
IIIb-08b n = 4
IIIb-08c n = 2

Example 22

Dimer IIa-15

This example relates to the preparation of dimer IIa-15, in which both imine groups in the diazepine rings have been reduced.

Analogously following the procedures in Example 5 and the scheme in FIG. 5, dibromide 34 coupled to compound 44 to yield a bis-alloc compound. Deprotection of the latter with Pd(PPh$_3$)$_4$ yielded dimer IIa-15. LCMS M+H=724.45.

(IIa-15)

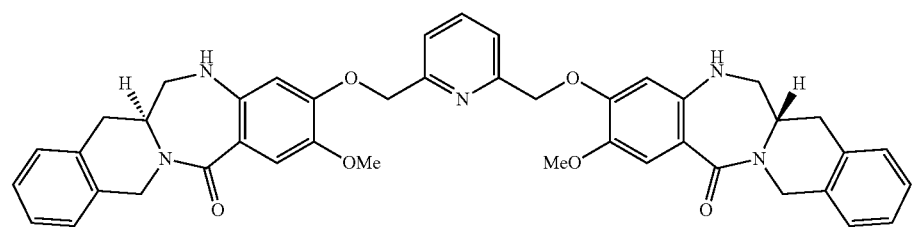

Example 23

Dimer-Linker IIIb-09

Figure 20:
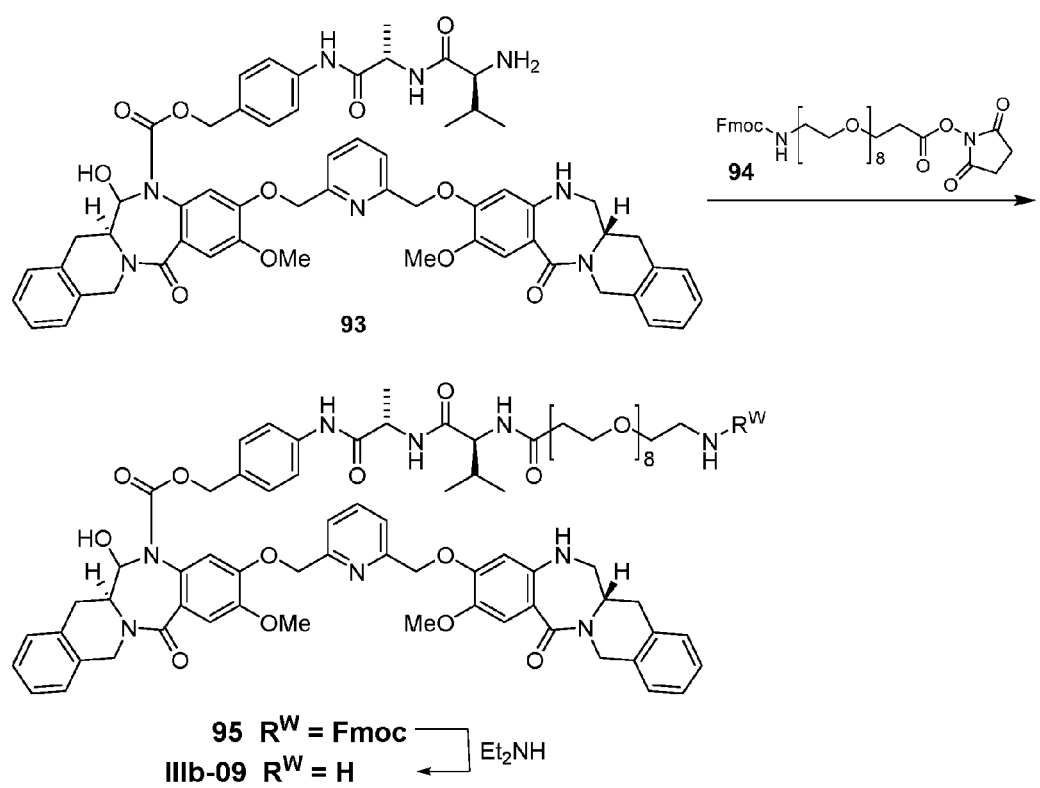

This example and FIG. 20 relate to the preparation of dimer-linker IIIb-09, wherein the linker has an amino group as reactive functional group. The amino group can participate in conjugation by acting as an amine donor in transglutaminase-mediated conjugation, as discussed hereinabove.

Alloc compound 44, dibromide 34, and compound 37 were used to prepare compound 93, generally following the procedures of Examples 6 and 14 and the schemes of respectively associated FIGS. 7A-7B and 15.

Compound 94 (0.079 g, 0.086 mmol, Quanta Biodesign) was coupled with compound 93 (0.091 g, 0.095 mmol) analogously following the procedures of Example 6 and FIG. 7B to yield compound 95 (40 mg, 27% yield). LCMS (M+2H)/2=853.45. Compound 95 (40 mg, 0.023 mmol) was dissolved in DMF (1.0 mL) and diethylamine (0.1 mL, 0.957 mmol) was added. The mixture was aged for 1 h, diluted with DMF and purified by Biotage C18 column, Solvent A=95% water, 5% Acetonitrile +0.05% formic acid; Solvent B=5% water, 95% Acetonitrile+0.05% formic acid.; gradient of 20-100%. The fractions containing product were combined and passed through a PL-HCO3- MP SPE 500 mg/6 mL cartridge, eluting with acetonitrile to afford a solution of the product as a free base. The bulk of the organic solvent was removed by rotary evaporation and water was removed by lyophilization to afford dimer-linker IIIb-09 as a white powder (18.5 mg, 51% yield). LCMS (M+2H)/2=742.35.

Example 24

Additional Intermediates

Figure 21:
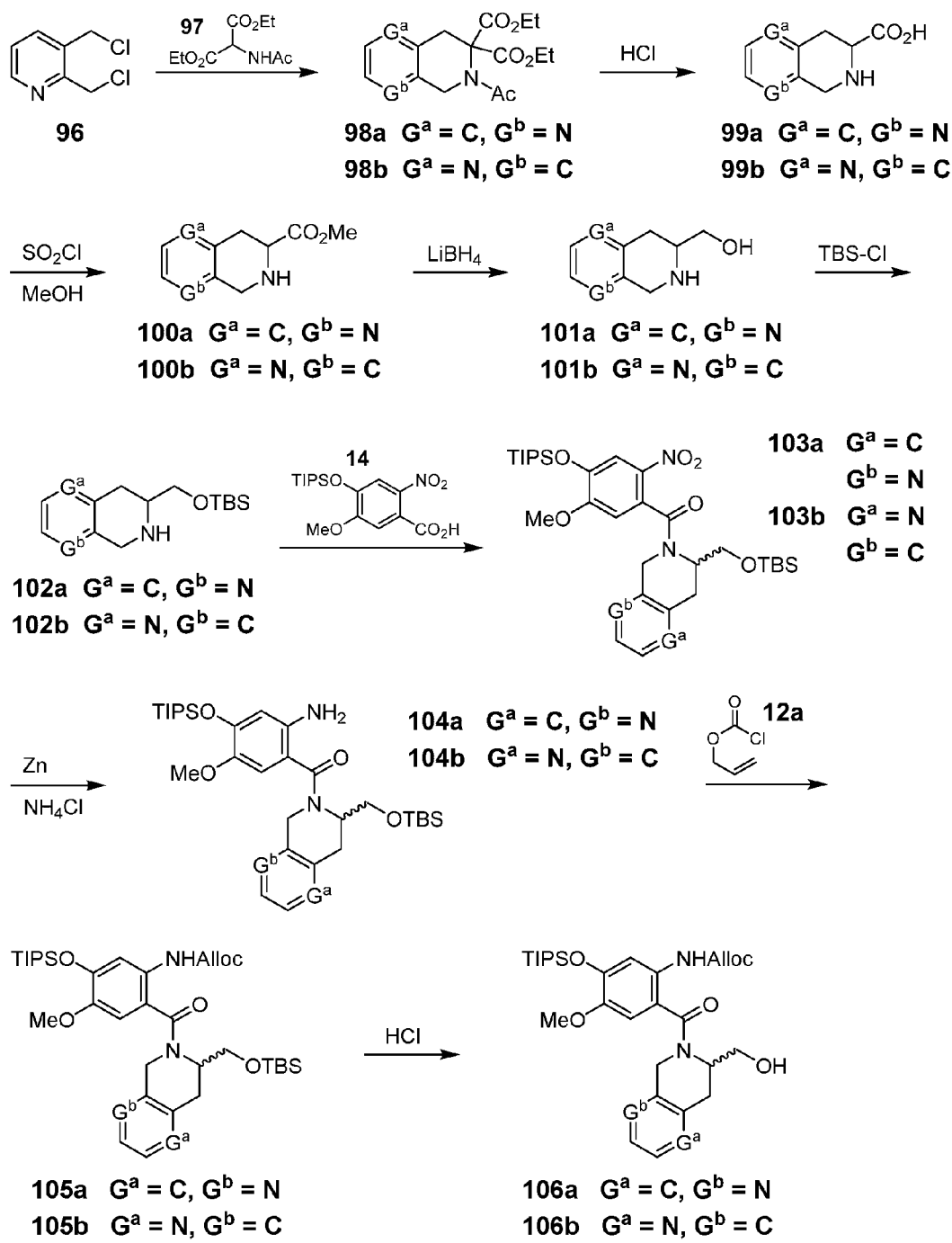

This example and FIG. 21 relate to the synthesis of intermediates suitable for the synthesis of THIQ-THIQ dimers having a further nitrogen on an aromatic ring.

Sodium hydride (60%, 2.72g, 56.8 mmol) was dissolved in DMF (50 mL) and cooled in an ice bath. Diethyl acetamidomalonate 97 (6.17 g, 28.4 mmol) was added portionwise over approximately 3 min and reacted 10 min further until bubbling had subsided. Pyridine 96 (5 g, 28.4 mmol, prepared per WO 2002/036555) was added over the course of approximately 1 min. The reaction mixture was diluted with water, and extracted with ethyl acetate. The organic layer was washed with a saturated aqueous NaCl, dried over $Na_2SO_4$, and concentrated in vacuum. Two regioisomers 98a/b were formed and taken as a mixture without further purification in the next step (7.2 g, 79% yield). LCMS M+H=321.10 (2 peaks with same mass).

A mixture of compounds 98a/b (7.2 g, 22.48 mmol) was treated with 6N HCl (50 ml, 1646 mmol). The resulting mixture was refluxed for 3 h. After having been cooled to RT, the reaction mixture was concentrated in vacuum. The brown solid that formed was concentrated along with dioxane and triturated with methanol. Two crops of a mixture of compounds 99a/b were collected, the first was 2.4 g of a tan solid and a second crop of 1.0g of a dark brown solid. These were used without further purification.

MeOH (20 mL) and thionyl chloride (1.578 mL, 21.62 mmol) were successively added at room temperature to a mixture of compounds 99a/b (1810 mg, 7.21 mmol) and then the resulting mixture was refluxed for 20 h. Reaction mixture was concentrated completely solid formed was re-concentrated with dioxane to remove excess of thionyl chloride to get brown solid. The mixture was triturated with MeOH to afford a solid which was partitioned between $Na_2CO_3$ and DCM and extracted 2× more. The combined organic phases were dried over $Na_2SO_4$ and the solvent evaporated to afford a mixture of compounds 100a/b (1.2g, 6.24 mmol, 87% yield).

A mixture of compounds 100a/b (1.2 g, 6.24 mmol) was dissolved in MeOH (50 mL) and treated with LiBH4 (0.136 g, 6.24 mmol). The mixture was refluxed for 2 h, evaporated and azeotroped with ethanol and toluene to afford a mixture of compounds 101a/b (1 g, 98% yield).

A mixture compounds 101a/b (1.0 g, 6.09 mmol) was dissolved in DMF (1 mL) and acetonitrile (5.8 mL) and treated with TBS-Cl (3.15 mL, 2.9M, 9.13 mmol) and imidazole (0.62 g, 9.13 mmol). The mixture was allowed to sit for 20 min and the bulk of the solvent was evaporated. The residue was partitioned between water and EtOAc. The aqueous phase was extracted 3× with EtOAc. The combined organic phases were washed with water and dried over $Na_2SO_4$. The mixture was filtered to remove the solids and the solvent evaporated. The residue was flashed chromatographed with 0-10% MeOH/DCM on a 24 g silica gel column. Under these conditions the 2 components were mostly resolved, but were recombined as a mixture of compounds 102a/b for further transformations (967 mg, 57% yield).

A mixture of compounds 102a/b (917 mg, 3.29 mmol) was taken on to a mixture of compounds 106a/b following the procedures of Example 3, mutatis mutandis:

103a/b: (1.39 g, 67% yield). LCMS M+H=630.20 (2 peaks with same mass).
104a/b: (0.52 g, 62% yield). LCMS M+H=600.20 (2 peaks with same mass).
105a/b: (0.50 g, 84% yield). LCMS M+H=684.75 (2 peaks with same mass).
106a: (158 mg, 38% yield) LCMS M+H=570.25 (after separation from 106b by silica gel chromatography, 50-100% EtOAc/hexanes gradient).
106b: (179 mg, 43% yield) LCMS M+H=570.30 (after separation).

Example 25

Dimer IIa-16

Figure 22:
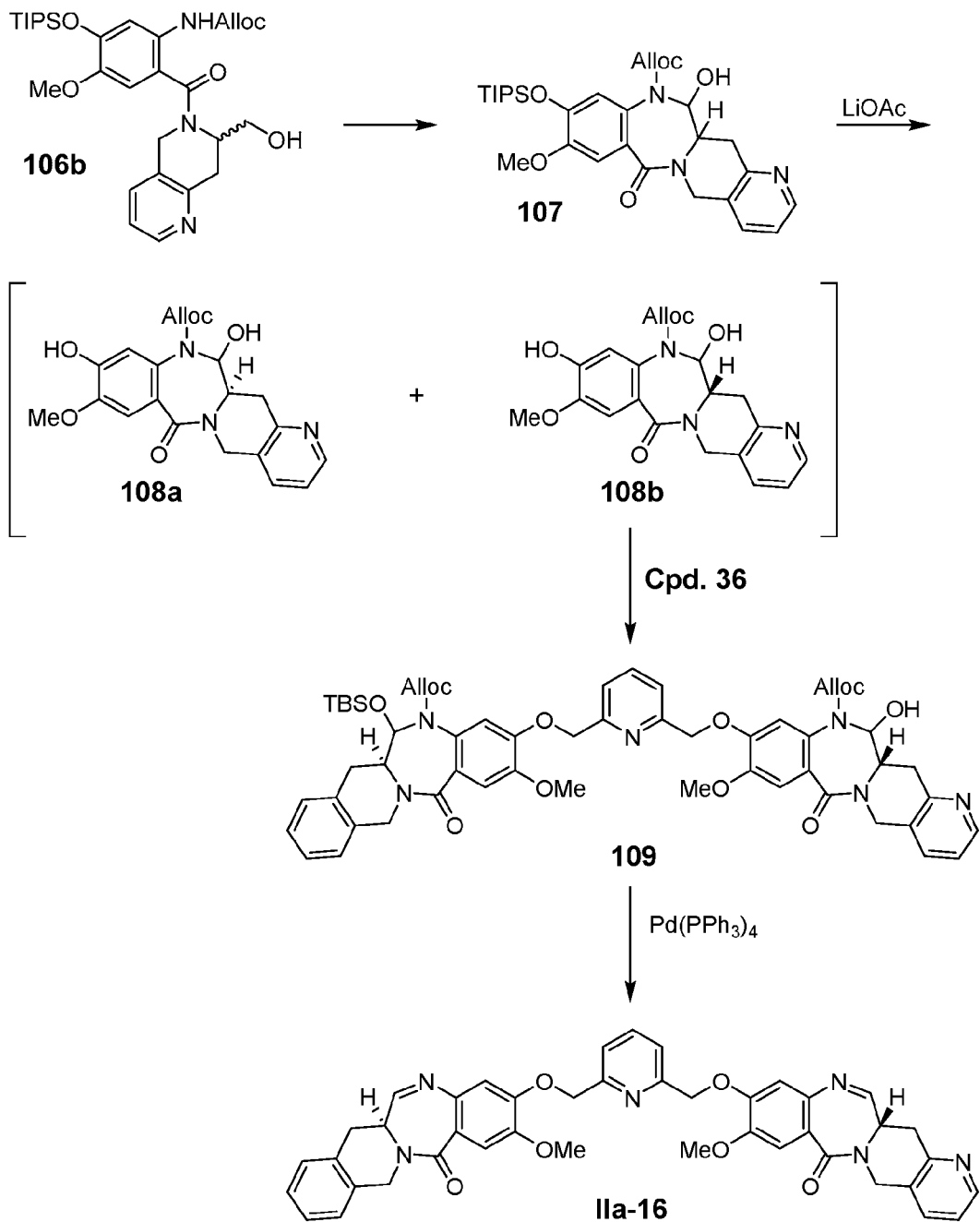

This example and FIG. 22 relate to the preparation of dimer IIa-16, which has a nitrogen in one of the outside benzene rings, i.e., one G or G' in formula (I) is N.

Compound 106b was converted to a mixture of enantiomers 108a and 108b following the procedures of Example 3, mutattis mutandis, which were separated by chiral SEC chromatography on a CHIRALPAK® IE column eluting with 20% MeOH in $CO_2$. 108a: LCMS M+H=411.95; 25 mg, 23% yield). 108b: LCMS M+H=411.95; 22 mg, 20% yield.

Enantiomer 108b was coupled with compound 36 analogously following the procedure Example 6 to afford bis-Alloc compound 109, which was then treated with Pd(PPh$_3$)$_4$ to yield dimer IIa-16 (4.3 mg, 45% yield). LCMS M+H=721.30.

Analogously, enantiomer 108a was converted to dimer 110, which has the unnatural stereochemistry in one of the dimer units:

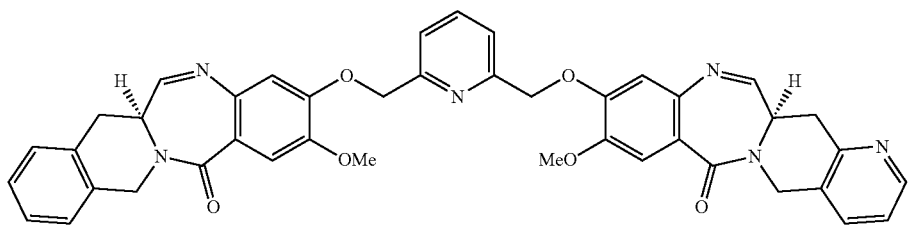

110

Also analogously, compound 106a was converted to enantiomers 111a (LCMS M+H=411.95; 18.6 mg, 18% yield) and 111b (LCMS M+H=411.95; 19 mg, 18% yield).

These enantiomers can be used to make dimers per the above procedures, mutatis mutandis.

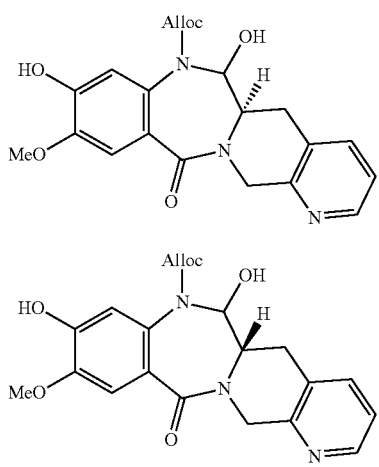

111a

111b

Example 26

Biological Activity of Dimers

The cytotoxic activity of dimers of this invention can be tested against various cancer cell lines, such as H226 lung cancer, DMS 79 lung cancer, H187 lung cancer, N87 gastric cancer, 786-O renal cancer, and/or OVCAR3 ovarian cancer cell lines. The ability of dimers to inhibit cell proliferation can be measured by either an ATP luminescence assay or an MTS cell proliferation assay. Generally, these two methods yield comparable results.

This is a general procedure for an ATP luminescence assay: Cells are seeded at 1×103 cells/well in 96-well plates for 3 h for ATP CellTiterGlo™ assays, respectively. Serial dilutions (1:3) of compounds are added to the wells. Plates are allowed to incubate for 72 h. A CellTiterGlo™ cell viability kit from Promega is used to measure ATP content of cells treated with test compounds following manufacturer's instruction. A decrease in the ATP content is a measure of decrease in cellular viability. The $EC_{50}$ value—the concentration at which an agent reduces cell viability by 50% of the maximum effect—can be calculated using PRISM™ software, version 5.0 (GraphPad Software, La Jolla, Calif., USA).

The MTS cell proliferation assay was performed as follows: CellTiter 96 Aqueous Non-Radioactive Cell Proliferation Kit from Promega (Madison, Wis.) is used to determine the number of viable cells in cell proliferation assay. Tumor cells are plated at certain seeding densities in sterile 384-well black clear bottom Matrix plates at 40 μL per well and incubated overnight at 37 □C in 5% $CO_2$ before assaying. On the next day, one set of cell plates (10 plates) is used to determine time zero cell density, and 3-(4,5-dimethylthiazol-2-yl)-5-(3-carboxymethoxyphenyl)-2-(4-sulfophenyl)-2H-tetrazolium is added at 4 μL/well into 10 plates followed by incubation at 37□C in 5% $CO_2$ for three hours. This tetrazolium reagent is bioreduced by liver cells to form a formazan product which is soluble in aqueous solution. Absorbance at 490 nm is measured on an Envision reader (Perkin Elmer, Boston, Mass.). On the same day, compounds are added into remaining cell plates (T72 plates) and incubated at 37 □C in 5% $CO_2$. After 72 hours, 4 μL MTS reagents are then added into those cell plates.

The plates are further incubated at 37□C in 5% $CO_2$ for three hours and the absorbance values at A490 were measured on an Envision reader.

Results are presented in Table I:

TABLE I

Biologic Activity of Dimers

| Dimer | Cancer Cell Line: $IC_{50}$ (nM) | | |
|---|---|---|---|
| | DMS 79 | H187 | N87 |
| IIa-01 | 0.001 | 0.001 | 0.02 |
| IIa-02 | — | — | 0.03 |
| IIa-03 | 0.002 | 0.002 | 0.03 |
| IIa-04 | — | — | 0.04 |
| IIa-05 | — | — | 0.1 |
| IIa-06 | — | — | 0.14 |
| IIa-07 | — | — | 0.25 |
| IIa-08 | — | — | 2.71 |
| IIa-09 | — | — | 4.7 |
| IIa-10 | — | — | 0.07 |
| IIa-11 | — | — | 4.92 |
| IIa-12 | — | — | 0.11 |
| IIa-13 | — | — | 0.03 |
| IIa-14 | — | — | 0.05 |
| IIa-15 | — | — | 2.88 |
| IIa-16 | — | — | 0.08 |
| 100 | — | — | 0.1 |

Example 27

Biological Activity of Conjugates

Dimer-linker compounds were conjugated to an anti-fucosyl GM1 antibody following the general procedure described hereinabove. Tests were conducted against N87 gastric cancer, DMS 79 and/or H187 small-cell lung cancer cell lines, the first expressing mesothelin and the latter two expressing fucos87yl GM1 on their cell surfaces. Activity was measured using a $^3$H thymidine assay (Cong et al. 2014). Results are presented in Table II.

TABLE II

Biologic Activity of Conjugates

| Conjugate | | | Cancer Cell Line - IC$_{50}$ (nM) | | |
|---|---|---|---|---|---|
| Antibody | Dimer-linker | DAR | DM 79 | H187 | N87 |
| Anti-fucosyl GM1 | IIIb-01 | ~2 | 0.3 | 0.5 | |
| Anti-fucosyl GM1 | IIIb-02 | ~2 | 2.1 | 1.8 | |
| Anti-fucosyl GM1 | IIIc-01 | ~2 | 0.4 | 0.4 | |
| Anti-mesothelin | IIIb-01 | — | — | — | 0.01 |
| Anti-mesothelin | IIIb-02 | — | — | — | 0.12 |
| Anti-mesothelin | IIIc-01 | — | — | — | 0.01 |
| Atni-mesothellin | IIIc-02 | — | — | — | 0.03 |

In a preferred embodiment, in a conjugate of this invention the antibody is an anti-fucosyl GM1 or an anti-mesothelin antibody.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Antonow et al., *J. Med. Chem.* 2010, 53, 2927.
Beau-Larvor et al., WO 2014/174111 A1 (2014).
Bose et al., *J. Am. Chem. Soc.* 1992, 114(12), 4939.
Bouchard et al., U.S. Pat. No. 8,404,678 B2 (2013).
Chari et al., WO 2013/177481 A1 (2013).
Commercon et al., U.S. Pat. No. 8,481,042 B2 (2013) [2013a].
Commercon et al., US 2013/0137659 A1 (2013) [2013b].
Fishkin et al., U.S. Pat. No. 8,765,740 B2 (2014).
Flygare et al., US 2013/0266595 A1 (2013).
Gauzy et al., U.S. Pat. No. 8,163,736 B2 (2012).
Gregson et al., *Chem. Comm.* 1999 (9), 797.
Gregson et al., *Bioorg. Med. Chem. Lett.* 2001, 11, 2859 [2001a].
Gregson et al., *J. Med. Chem.* 2001, 44, 737 [2001b].
Gregson et al., *J. Med. Chem.* 2004, 47, 1161.
Gregson et al., U.S. Pat. No. 7,612,062 B2 (2009).
Hartley, *Exp. Opinion Investigational Drugs* 2011, 20(6), 733.
Hartley et al., *Investigational New Drugs* 2012, 30, 950.
Howard, US 2014/0120118 A1 (2014) [2014a].
Howard, US 2014/0127239 A1 (2014) [2014b].
Howard, WO 2014/096365 A1 (2014) [2014c].
Howard, WO 2014/096368 A1 (2014) [2014d].
Howard, WO 2014/140174 A1 (2014) [2014e].
Howard et al., US 2007/0191349 A1 (2007).
Howard et al., U.S. Pat. No. 7,528,126 B2 (2009) [2009a].
Howard et al., U.S. Pat. No. 7,557,099 B2 (2009) [2009b].
Howard et al., U.S. Pat. No. 7,741,319 B2 (2010).
Howard et al., US 2011/0256157 A1 (2011).
Howard et al., U.S. Pat. No. 8,501,934 B2 (2013) [2013a].
Howard et al., U.S. Pat. No. 8,592,576 B2 (2013) [2013b].
Howard et al., US 2013/0028919 A1 (2013) [2013c].
Howard et al., WO 2013/041606 A1 (2013) [2013e].
Howard et al., U.S. Pat. No. 8,697,688 B2 (2014) [2014a].
Howard et al., US 2014/0120118 A1 (2014).
Howard et al. US 2014/0234346 A1 (2014) [2014b].
Howard et al., US 2014/0274907 A1 (2014) [2014c].
Howard et al., US 2014/0294868 A1 (2014).
Howard et al., WO 2014/096368 A1 (2014).
Howard et al., WO 2014/140174 A1 (2014).
Howard et al., WO 2014/140862 A2 (2014) [2014d].
Jeffrey et al., *Bioconj. Chem.* 2013, 24, 1256.
Jeffrey et al., US 2014/0286970 A1 (2014) [2014a].
Jeffrey et al., US 2014/0302066 A1 (2014) [2014b].
Kothakonda et al., *Bioorg. Med. Chem. Lett.* 2004, 14, 4371.
Li et al., U.S. Pat. No. 8,426,402 B2 (2013).
Li et al., WO 2014/031566 A1 (2014).
Liu et al., U.S. Pat. No. 7,244,724 B2 (2007).
Schrama et al., *Nature Rev. Drug Disc.* 2006, 5, 147.
Senter et al., U.S. Pat. No. 7,659,241 B2 (2010).
Thurston et al., *J. Org. Chem.* 1996, 61(23), 8141.
Thurston et al., *J. Med. Chem.* 1999, 42, 1951.
Thurston et al., U.S. Pat. No. 7,049,311 B1 (2006).
Thurston et al., U.S. Pat. No. 7,407,951 B1 (2008).
Zhao et al., WO 2014/080251 A1 (2014).

What is claimed is:
1. A compound having a structure represented by formula (IIa-03):

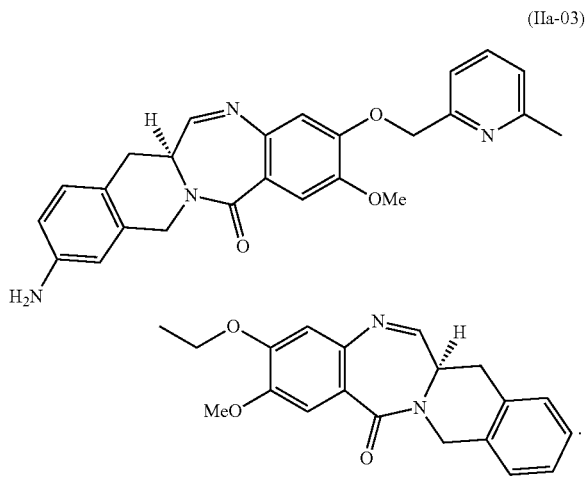

(IIa-03)

* * * * *